US010963671B2

United States Patent
Pi et al.

(10) Patent No.: US 10,963,671 B2
(45) Date of Patent: Mar. 30, 2021

(54) MULTIFUNCTION FINGERPRINT SENSOR HAVING OPTICAL SENSING CAPABILITY

(71) Applicant: Shenzhen Goodix Technology Co., Ltd., Shenzhen (CN)

(72) Inventors: Bo Pi, San Diego, CA (US); Yi He, San Diego, CA (US)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 15/846,134

(22) Filed: Dec. 18, 2017

(65) Prior Publication Data

US 2018/0173343 A1 Jun. 21, 2018

Related U.S. Application Data

(63) Continuation of application No. PCT/US2016/038445, filed on Jun. 20, 2016.
(Continued)

(51) Int. Cl.
*G06K 9/00* (2006.01)
*G06F 3/041* (2006.01)
(Continued)

(52) U.S. Cl.
CPC ...... *G06K 9/00114* (2013.01); *A61B 5/02416* (2013.01); *A61B 5/1172* (2013.01);
(Continued)

(58) Field of Classification Search
CPC .. G06K 9/00114; G06K 9/0012; G06K 9/004; G06F 3/042; G06F 3/0421;
(Continued)

(56) References Cited

U.S. PATENT DOCUMENTS 5,420,936 A   5/1995 Fitzpatrick et al.
5,726,443 A   3/1998 Immega et al.
(Continued)

FOREIGN PATENT DOCUMENTS

CN  1235318 A  11/1999
CN  1320847 A  11/2001
(Continued)

OTHER PUBLICATIONS

International Search Report from PCT/CN2017/095908 dated Nov. 7, 2017 (6 pages).
(Continued)

*Primary Examiner* — Liliana Cerullo
(74) *Attorney, Agent, or Firm* — Perkins Coie LLP

(57) ABSTRACT

In one aspect, a fingerprint sensor device includes a touch panel with an integrated touch sensor module. The integrated touch sensor module includes sensing circuitry to generate a sensor signal responsive to detecting a contact input associated with a fingerprint. The sensing circuitry includes a fingerprint sensor to detect the contact input and generate a signal indicative of an image of the fingerprint, and a biometric sensor to generate a signal indicative of a biometric marker different form the fingerprint. The generated sensor signal includes the signal indicative of the image of the fingerprint and the signal indicative of the biometric marker different from the fingerprint. The sensing circuitry includes processing circuitry communicatively coupled to the sensing circuitry to process the generated sensor signal to determine whether the contact input associated with the fingerprint belongs to a live finger. In another aspect, a device includes a touch screen and an optical sensor module located below the touch screen to provide optical fingerprint sensing.

53 Claims, 26 Drawing Sheets

Related U.S. Application Data

(60) Provisional application No. 62/181,718, filed on Jun. 18, 2015.

(51) Int. Cl.
  *G06F 3/042* (2006.01)
  *A61B 5/1172* (2016.01)
  *A61B 5/024* (2006.01)
  *A61B 5/00* (2006.01)
  *A61B 5/145* (2006.01)

(52) U.S. Cl.
  CPC ............ *G06F 3/041* (2013.01); *G06F 3/042* (2013.01); *G06F 3/0421* (2013.01); *G06K 9/0004* (2013.01); *G06K 9/0012* (2013.01); *A61B 5/0077* (2013.01); *A61B 5/145* (2013.01); *A61B 5/14532* (2013.01); *A61B 5/14542* (2013.01); *A61B 5/7203* (2013.01)

(58) Field of Classification Search
  CPC ... A61B 5/02416; A61B 5/1172; A61B 5/145; A61B 5/14542; A61B 5/0077; A61B 5/7203; A61B 5/14532
  See application file for complete search history.

(56) References Cited

U.S. PATENT DOCUMENTS

| | | | |
|---|---|---|---|
| 5,953,441 A | 9/1999 | Setlak | |
| 6,292,576 B1 | 9/2001 | Brownlee | |
| 6,327,376 B1 | 12/2001 | Harkin | |
| 7,535,468 B2 | 5/2009 | Uy | |
| 7,728,959 B2 | 6/2010 | Waldman et al. | |
| 7,751,595 B2 | 7/2010 | Russo | |
| 7,936,907 B2 | 5/2011 | Maurer et al. | |
| 9,829,614 B2 | 11/2017 | Smith et al. | |
| 9,946,375 B2 | 4/2018 | Akhavan et al. | |
| 9,990,533 B2 | 6/2018 | Pi et al. | |
| 2003/0044051 A1 | 3/2003 | Fujieda | |
| 2003/0090650 A1 | 5/2003 | Fujieda | |
| 2003/0190062 A1 | 10/2003 | Noro | |
| 2004/0252867 A1* | 12/2004 | Lan | G06K 9/0004 382/124 |
| 2006/0115128 A1 | 6/2006 | Mainguet | |
| 2007/0035843 A1 | 2/2007 | Cassarly | |
| 2007/0109438 A1 | 5/2007 | Duparre et al. | |
| 2007/0147667 A1 | 6/2007 | Sumita et al. | |
| 2007/0211926 A1 | 9/2007 | Shinzaki et al. | |
| 2008/0121442 A1 | 5/2008 | Boer et al. | |
| 2008/0122803 A1 | 5/2008 | Izadi et al. | |
| 2008/0237766 A1 | 10/2008 | Kim | |
| 2009/0021487 A1 | 1/2009 | Tien | |
| 2009/0116030 A1 | 5/2009 | Bahuguna | |
| 2009/0232367 A1 | 9/2009 | Shinzaki | |
| 2010/0008552 A1 | 1/2010 | Shin et al. | |
| 2010/0113952 A1 | 5/2010 | Raguin et al. | |
| 2010/0240415 A1* | 9/2010 | Kim | G06F 3/03547 455/565 |
| 2010/0321152 A1 | 12/2010 | Argudyaev et al. | |
| 2011/0148819 A1 | 6/2011 | Yu | |
| 2011/0233383 A1 | 9/2011 | Oku | |
| 2012/0019744 A1 | 1/2012 | Lee | |
| 2012/0069042 A1 | 3/2012 | Ogita et al. | |
| 2012/0105614 A1 | 5/2012 | Wu et al. | |
| 2012/0182266 A1 | 7/2012 | Han | |
| 2013/0051635 A1 | 2/2013 | Wu et al. | |
| 2013/0120760 A1 | 5/2013 | Raguin et al. | |
| 2013/0127790 A1* | 5/2013 | Wassvik | G06F 3/042 345/175 |
| 2013/0222282 A1 | 8/2013 | Huang et al. | |
| 2013/0258086 A1* | 10/2013 | Erhart | H04N 5/23219 348/77 |
| 2013/0287272 A1 | 10/2013 | Lu et al. | |
| 2013/0314377 A1 | 11/2013 | Los | |
| 2014/0016047 A1 | 1/2014 | Hwang et al. | |
| 2014/0036168 A1 | 2/2014 | Ludwig | |
| 2014/0098058 A1* | 4/2014 | Baharav | G06F 3/0421 345/174 |
| 2014/0125788 A1 | 5/2014 | Wu | |
| 2014/0133715 A1 | 5/2014 | Ballard | |
| 2014/0168167 A1 | 6/2014 | Chou | |
| 2014/0218327 A1 | 8/2014 | Shi et al. | |
| 2014/0354905 A1 | 12/2014 | Kitchens et al. | |
| 2014/0368764 A1 | 12/2014 | Lee et al. | |
| 2015/0078633 A1 | 3/2015 | Hung | |
| 2015/0146944 A1 | 5/2015 | Pi et al. | |
| 2015/0220767 A1 | 8/2015 | Yoon et al. | |
| 2015/0227773 A1 | 8/2015 | Miesak et al. | |
| 2016/0004899 A1 | 1/2016 | Pi et al. | |
| 2016/0026844 A1 | 1/2016 | Kim et al. | |
| 2016/0042216 A1 | 2/2016 | Yang et al. | |
| 2016/0092718 A1 | 3/2016 | Jensen et al. | |
| 2016/0104025 A1 | 4/2016 | Thompson et al. | |
| 2016/0132712 A1 | 5/2016 | Yang et al. | |
| 2016/0180146 A1 | 6/2016 | Setterberg et al. | |
| 2016/0224816 A1 | 8/2016 | Smith et al. | |
| 2016/0247010 A1 | 8/2016 | Huang et al. | |
| 2016/0254312 A1 | 9/2016 | Lee | |
| 2016/0266695 A1 | 9/2016 | Bae et al. | |
| 2016/0364036 A1 | 12/2016 | Deng et al. | |
| 2017/0017824 A1 | 1/2017 | Smith et al. | |
| 2017/0083745 A1 | 3/2017 | Goodelle et al. | |
| 2017/0124370 A1 | 5/2017 | He et al. | |
| 2017/0220182 A1 | 8/2017 | Schwartz et al. | |
| 2017/0220838 A1 | 8/2017 | He et al. | |
| 2017/0220842 A1 | 8/2017 | Thompson | |
| 2017/0220844 A1 | 8/2017 | Jones et al. | |
| 2017/0270340 A1 | 9/2017 | Gao et al. | |
| 2017/0270342 A1 | 9/2017 | He et al. | |
| 2017/0337412 A1 | 11/2017 | Bhat et al. | |
| 2017/0337413 A1 | 11/2017 | Bhat et al. | |
| 2018/0000500 A1 | 1/2018 | He et al. | |
| 2018/0075283 A1 | 3/2018 | You et al. | |
| 2018/0113512 A1 | 4/2018 | Kang et al. | |
| 2018/0114047 A1 | 4/2018 | Kim et al. | |
| 2018/0017334 A1 | 6/2018 | Pi et al. | |
| 2018/0165494 A1 | 6/2018 | Kim et al. | |
| 2018/0188422 A1 | 7/2018 | Fujii et al. | |

FOREIGN PATENT DOCUMENTS

| | | |
|---|---|---|
| CN | 1417751 A | 5/2003 |
| CN | 101276406 A | 10/2008 |
| CN | 101416202 A | 4/2009 |
| CN | 101950360 A | 1/2011 |
| CN | 202120281 U | 1/2012 |
| CN | 102411878 A | 4/2012 |
| CN | 103902955 A | 12/2012 |
| CN | 202758369 U | 2/2013 |
| CN | 103049138 A | 4/2013 |
| CN | 203535653 U | 10/2013 |
| CN | 103458073 A | 12/2013 |
| CN | 103699884 A | 4/2014 |
| CN | 103942537 A | 7/2014 |
| CN | 104155785 A | 11/2014 |
| CN | 104318204 A | 12/2014 |
| CN | 203982399 U | 12/2014 |
| CN | 204069106 U | 12/2014 |
| CN | 104239869 A | 1/2015 |
| CN | 104318205 A | 1/2015 |
| CN | 204480268 U | 7/2015 |
| CN | 204595873 U | 8/2015 |
| CN | 105094443 A | 11/2015 |
| CN | 105094600 A | 11/2015 |
| CN | 105138171 A | 12/2015 |
| CN | 105184282 A | 12/2015 |
| CN | 105205464 A | 12/2015 |
| CN | 205003632 U | 1/2016 |
| CN | 105372256 A | 3/2016 |
| CN | 107004130 A | 8/2017 |
| EP | 2074946 A1 | 7/2009 |
| EP | 2562683 A1 | 2/2013 |
| EP | 3273329 A1 | 1/2018 |

(56) References Cited

FOREIGN PATENT DOCUMENTS

| | | | |
|---|---|---|---|
| JP | 11-120324 A | 4/1999 | |
| JP | 2003144420 A | 5/2003 | |
| JP | 2014209379 A | 11/2014 | |
| KR | 20030095726 A | 12/2003 | |
| KR | 20110095565 A | 8/2011 | |
| KR | 20150092964 A | 8/2015 | |
| KR | 1020150120043 A | 10/2015 | |
| KR | 20150131944 A | 11/2015 | |
| TW | 200905578 A | 2/2009 | |
| TW | 201426563 A | 7/2014 | |
| WO | 01/69520 A2 | 9/2001 | |
| WO | 2001/069520 A3 | 9/2001 | |
| WO | 2011110821 A1 | 9/2011 | |
| WO | 2015061304 A1 | 4/2015 | |
| WO | 2016205832 A1 | 12/2016 | |
| WO | 2017/076292 A1 | 5/2017 | |
| WO | 2018/049944 A1 | 3/2018 | |

OTHER PUBLICATIONS

International Search Report from PCT/CN2018/078360 dated May 31, 2018 (4 pages).
International Search Report from PCT/CN2017/072575 dated Apr. 1, 2017 (4 pages).
International Search Report from PCT/CN2017/083117 dated Aug. 10, 2017 (4 pages).
International Search Report from PCT/CN2018/071400 dated Mar. 29, 2018 (5 pages).
Korean Office Action from related Korean Patent Application No. 10-2017-7023032 dated Jan. 12, 2018 (9 pages). (English translation currently unavailable).
Supplementary Partial European Search Report from related European Patent Application No. 17743741 dated Nov. 8, 2018 (13 pages).
Chinese Office Action from related Chinese Patent Application No. 201780000132.6 dated Dec. 15, 2017 (6 pages). (English translation currently unavailable).
Chinese Office Action from related Chinese Patent Application No. 201780000132.6 dated Apr. 11, 2018 (10 pages). (English translation currently unavailable).
International Search Report from PCT/CN2016/104354 dated Feb. 8, 2017 (5 pages).
Korean Office Action from related Korean Patent Application No. 10-2017-7022868 dated Jan. 12, 2018 (9 pages). (English translation currently unavailable).
Supplementary European Search Report from related European Patent Application No. 16861560 dated Nov. 22, 2017 (8 pages).
Korean Office Action from related Korean Patent Application No. 10-2017-7031287 dated Feb. 14, 2018 (7 pages). (English translation currently unavailable).
Supplementary European Search Report from related European Patent Application No. 16812652 dated Mar. 19, 2018 (7 pages).
International Search Report and Written Opinion dated Sep. 29, 2018 for International Application No. PCT/CN2018/094865, filed on Jul. 6, 2018 (4 pages).
International Search Report and Written Opinion dated Sep. 30, 2016 for International Application No. PCT/US2016/038445, filed on Jun. 20, 2016 (16 pages).
Extended European Search Report dated Apr. 1, 2019 for EP Application No. 17743741.5 (13 pages).
Extended European Search Report dated Jun. 3, 2019 for EP Application No. 17809591.5 (8 pages).
Partial/Supplementary European Search Report dated May 20, 2019 for EP1875868.4 (14 Pages).
Partial/Supplemental European Search Report dated Jun. 5, 2019 for EP17850146.6 (14 pages).
Partial/Supplemental European Search Report dated Jun. 11, 2019.
Office Action dated Feb. 6, 2019 for EP16812652.2.
"Counterclockwise: OLED screens challenge old-fashioned LCDs", GSM Arena, Dec. 2017, available at address: https://www.gsmarena.com/counterclockwise_oled_screens-news-28552.php.
Chinese Application No. 201680003673.X Office Action dated Oct. 9, 2019.
Extended European Search Report dated Aug. 27, 2019 for EP18735868.4 (12 pages).
Extended European Search Report dated Sep. 25, 2019 for EP18763421.7 (12 pages).
Office Action dated Jul. 8, 2019 for EP16812652.2 (6 pages).
Office Action for Chinese Patent Application No. 201780000132.6 dated Nov. 12, 2019 (3 pages).
Extended European Search Report dated Nov. 4, 2019 for European Patent Application No. 17850146.6 (16 pages).
Office Action dated Jun. 16, 2020 for European Application 18763421.7 (5 pages).
Office Action dated Mar. 30, 2020 for Chinese Patent Application No. 201680023923.6 (9 pages).
Office Action dated May 28, 2020 for Chinese Patent Application No. 201780027146.7 (8 pages).
Examination Report dated Jul. 3, 2020 for Indian Patent Application No. 201717038864 (6 pages).
Examination Report dated Jul. 13, for Indian Patent Application No. 201717031286 (7 pages).
Examination Report dated Jul. 31, 2020 for Chinese Application No. 201911236353.0.
Office Action dated Aug. 27, 2020 for Chinese Patent Application No. 201680023923.6 (7 pages).
Office Action dated Aug. 28, 2020 for Chinese Patent Application No. 201780027146.7 (12 pages).
Office Action dated Oct. 16, 2020 for Chinese Patent Application No. 201911236353.0 (5 pages).

\* cited by examiner

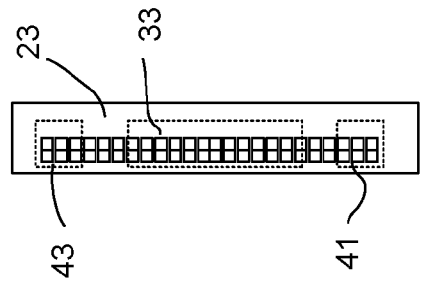
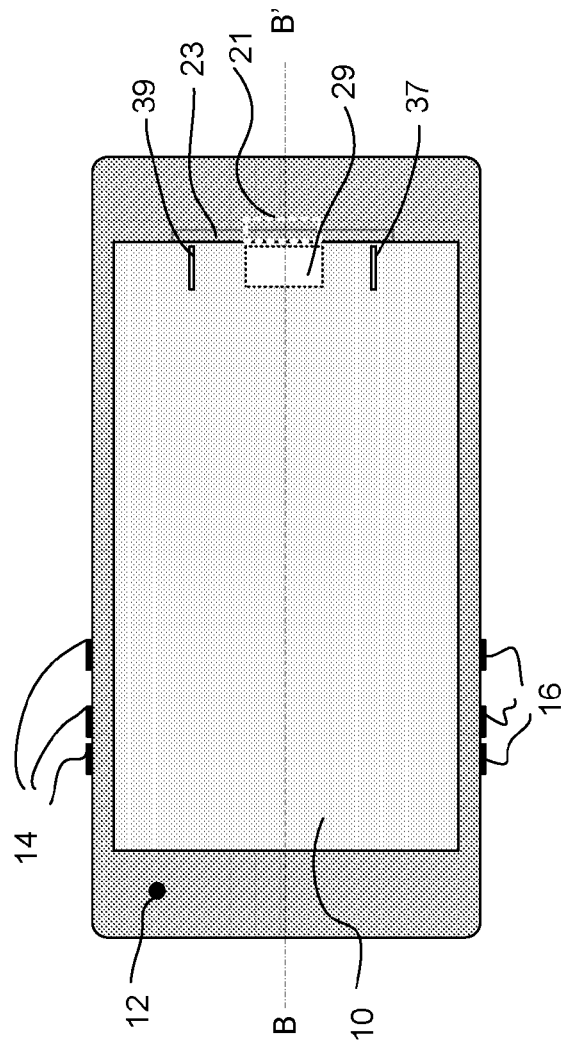
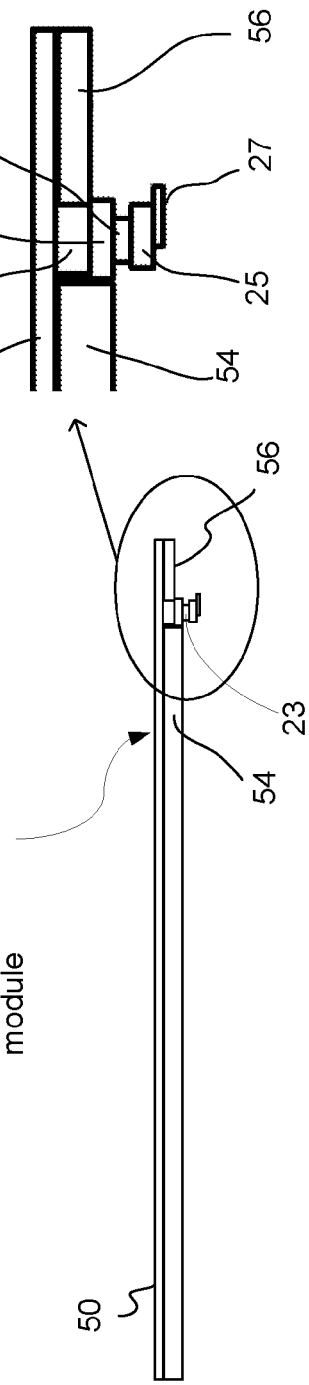

Contiguous and uniform top cover surface above both the display screen and the fingerprint sensor module

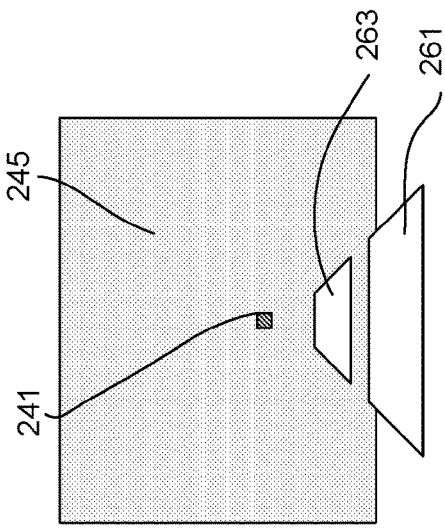
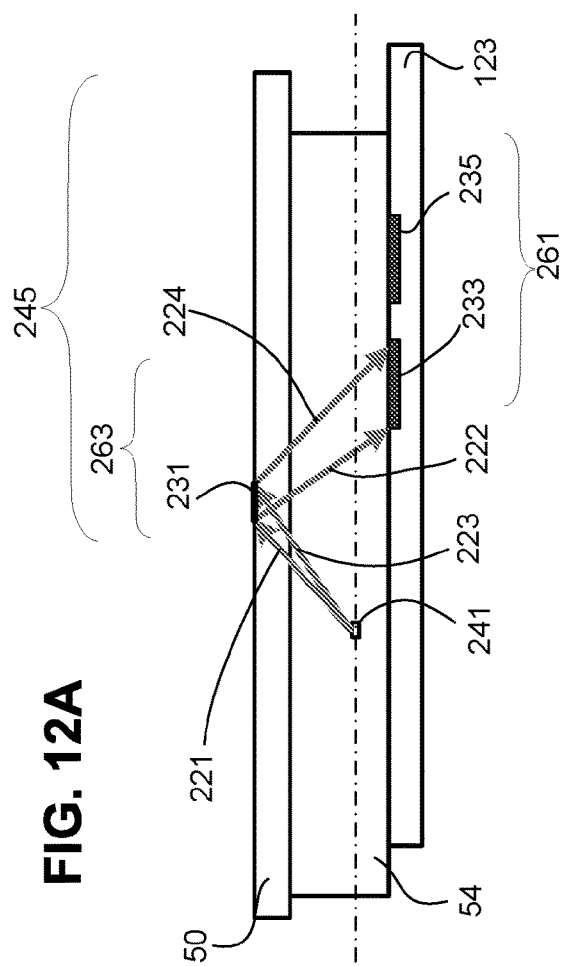
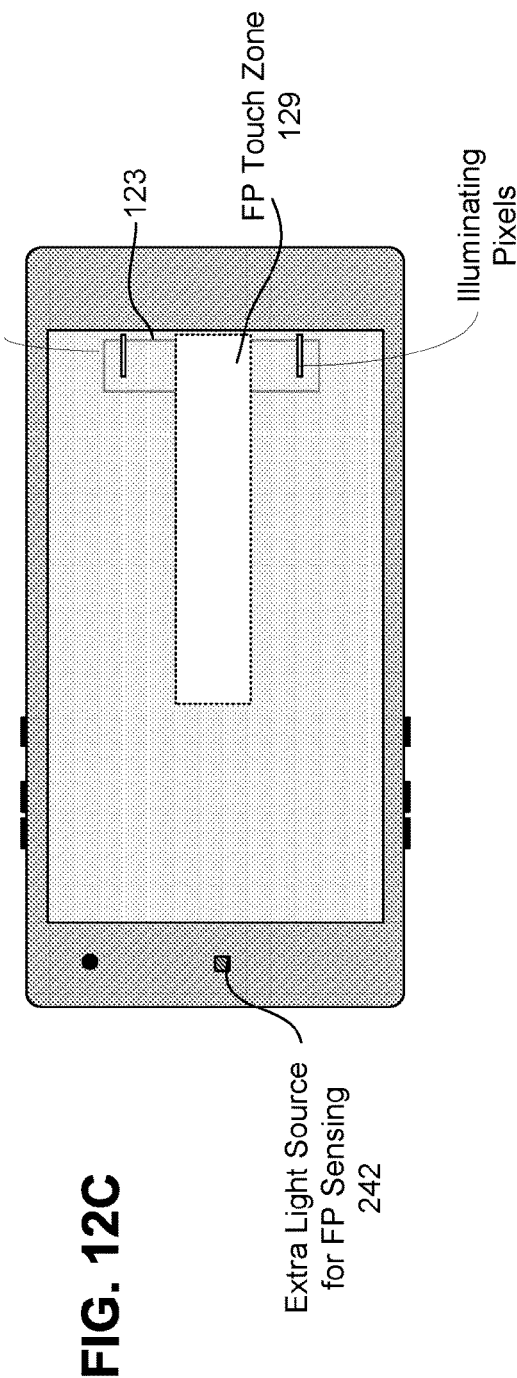

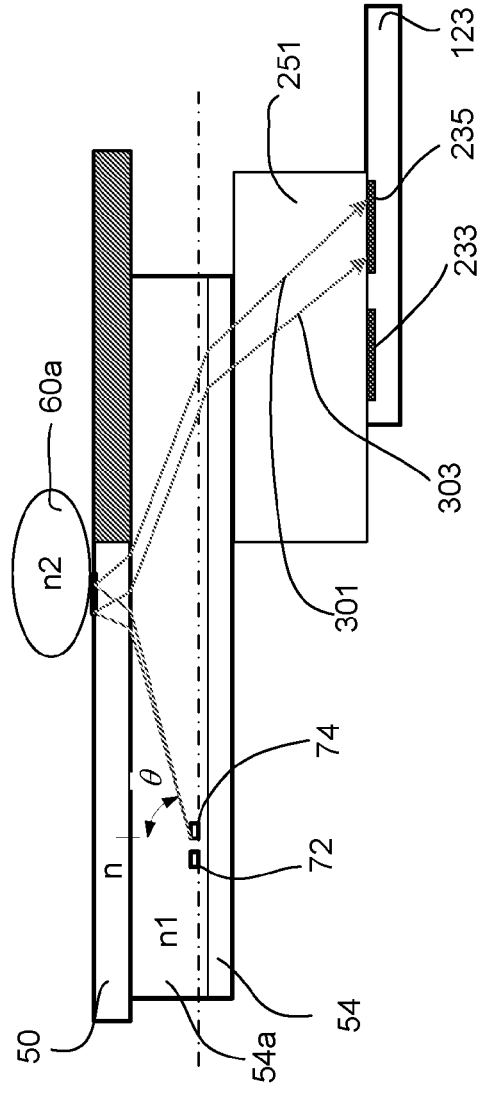
FIG. 17
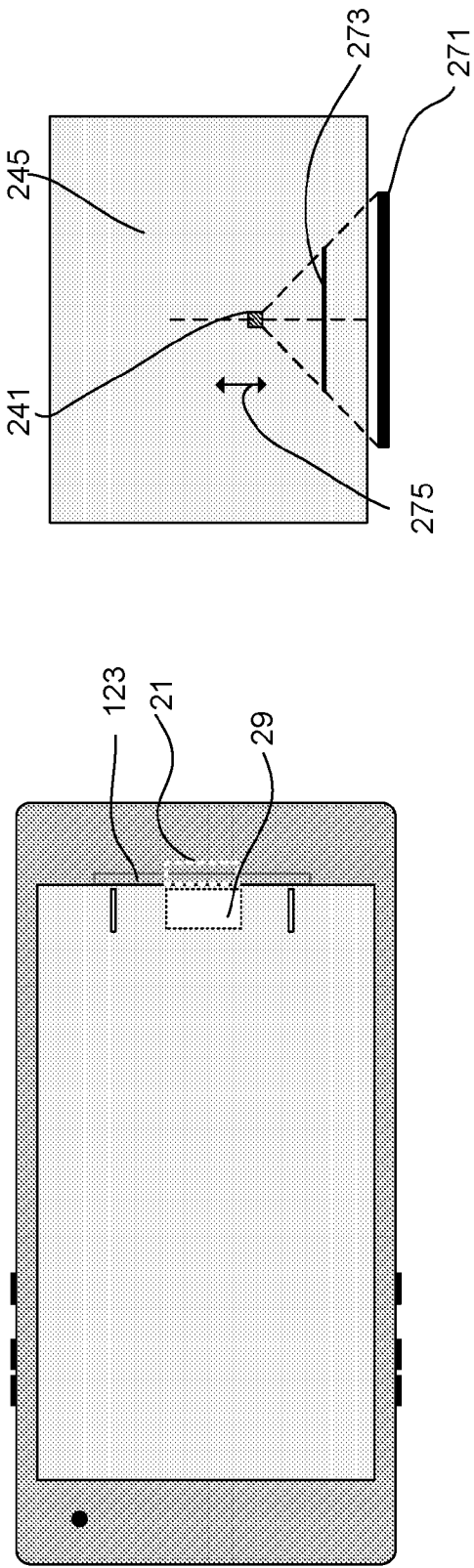
FIG. 18B
FIG. 18A

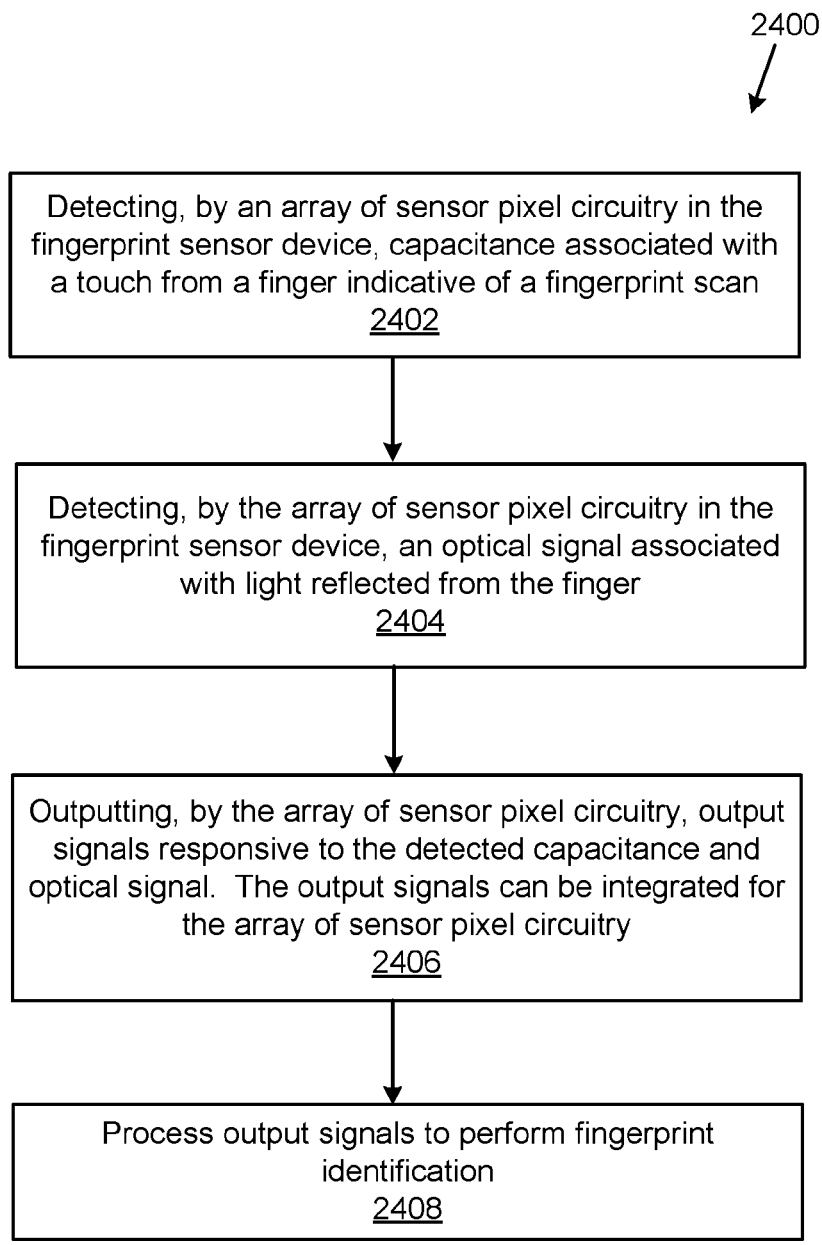

MULTIFUNCTION FINGERPRINT SENSOR HAVING OPTICAL SENSING CAPABILITY

CROSS REFERENCE TO RELATED APPLICATIONS

This patent document claims the benefit of priority of U.S. Provisional Patent Application No. 62/181,718, filed on Jun. 18, 2015, and entitled "MULTIFUNCTION FINGERPRINT SENSOR AND PACKAGING," which is incorporated by reference in its entirety as part of the disclosure of this patent document.

TECHNICAL FIELD

This patent document generally relates to fingerprint recognition for securely accessing an electronic device that includes mobile and wearable devices.

BACKGROUND

Electronic devices including portable or mobile computing devices, such as laptops, tablets, smartphones, and gaming systems can employ user authentication mechanisms to protect personal data and prevent unauthorized access. User authentication on an electronic device can be carried out through one or multiple forms of biometric identifiers, which can be used alone or in addition to conventional password authentication methods. A popular form of biometric identifiers is a person's fingerprint pattern. A fingerprint sensor can be built into the electronic device to read a user's fingerprint pattern so that the device can only be unlocked by an authorized user of the device through authentication of the authorized user's fingerprint pattern.

SUMMARY

The examples of implementations described in this patent document provide fingerprint sensor designs that use optical sensors for sensing fingerprints or a combination of optical sensors and another type of fingerprint sensors such as capacitive sensors to sense fingerprints. The described fingerprint sensor designs can be used in various devices, systems or applications, and can be configured to be particularly suitable for mobile applications, and various wearable or portable devices.

In one aspect, an electronic device with touching sensing and fingerprint sensing capabilities is provided to include a touch screen that provides touch sensing operations; a top transparent layer formed over the touch screen as an interface for being touched by a user for the touch sensing operations; and an optical sensor module located below the touch screen to receive light that is returned from the top transparent layer and transmits through the touch screen. The optical sensor module includes an optical detector array of photodetectors positioned to receive at least a portion of the returned light to detect a fingerprint. In one implementation, the optical sensor module includes an array of optical collimators located between the touch screen and the optical detector array to direct the received portion of the returned light to the photodetectors through the optical collimators. In another implementation, the touch screen includes a fingerprint sensing zone for a user to touch for fingerprint sensing to generate the returned light received by the optical detector array for detecting a fingerprint; a first optical sensing zone and a second optical sensing zone; and the optical module includes (1) a first additional optical detector located on a first side of the optical detector array to receive a portion of the returned light from the first optical sensing zone, and (2) a second additional optical detector located on a second opposite side of the optical detector array to receive a portion of the returned light from the second optical sensing zone. The first and second additional optical detectors produce detector signals indicating whether the returned light is reflected from a finger of a live person. In yet another implementation, the touch screen includes display pixels that produce light for displaying images and for illuminating a user's finger in touch with the top transparent layer to produce the returned light; and the touch screen includes a fingerprint sensing zone for a user to touch for fingerprint sensing to receive illumination light from one or more display pixels that are located to generate illumination light to the fingerprint sensing zone in a way that the illumination light undergoes total optical reflection at a top surface of the top transparent layer to direct the totally reflected light to the optical detector array for detecting a fingerprint.

In another aspect, a fingerprint sensor device includes a touch panel with an integrated touch sensor module. The integrated touch sensor module includes sensing circuitry to generate a sensor signal responsive to detecting a contact input associated with a fingerprint. The sensing circuitry includes a fingerprint sensor to detect the contact input and generate a signal indicative of an image of the fingerprint, and a biometric sensor to generate a signal indicative of a biometric marker different form the fingerprint. The generated sensor signal includes the signal indicative of the image of the fingerprint and the signal indicative of the biometric marker different from the fingerprint. The sensing circuitry includes processing circuitry communicatively coupled to the sensing circuitry to process the generated sensor signal to determine whether the contact input associated with the fingerprint belongs to a live finger. In implementations, the fingerprint sensor or the biometric sensor of the sensing circuitry includes an optical sensor.

In another aspect, an electronic device is provided to include a central processor; a touch panel in communication with the central processor; and a fingerprint sensor device integrated into the touch panel and in communication with the central processor. The fingerprint sensor device includes a sensing circuitry to generate a sensor signal responsive to detecting a contact input associated with a fingerprint. The sensing circuitry includes a fingerprint sensor to detect the contact input and generate a signal indicative of an image of the fingerprint, and a biometric sensor to generate a signal indicative of an identification of a biometric marker different from the fingerprint. The generated sensor signal includes the signal indicative of the image of the fingerprint and the signal indicative of the biometric marker different from the fingerprint. Processing circuitry is communicatively coupled to the sensing circuitry to process the generated sensor signal to determine whether the contact input associated with the fingerprint belongs to a live finger. In implementations, the fingerprint sensor or the biometric sensor of the sensing circuitry includes an optical sensor.

In another aspect, a method is provided for detecting a live finger during a fingerprint scan and includes detecting, by a fingerprint sensor, a contact input associated with a source of a fingerprint; generating an image signal from the fingerprint sensor responsive to the detected contact input, wherein the generated image signal from the fingerprint sensor is indicative of one or more images of the fingerprint; generating, by a biometric sensor, a biometric marker detection signal indicative of a biometric marker different from the fingerprint; and processing, by processing circuitry, the generated image signal and the biometric marker detection signal to determine whether the detected contact and the associated one or more fingerprint images are from a live finger. In implementations, the fingerprint sensor or the biometric sensor of the sensing circuitry includes an optical sensor.

In yet another aspect, a method is provided of finger scanning and includes initiating sensor detection to activate a sensor module including a light source and a light detector; controlling the light source to modulate light beams emitted by the light source to carry modulated signal information including amplitude, phase shift, frequency change, or a combination; acquiring an optical signal in response to the emitted modulated light beams; demodulating the acquired optical signal; and processing the demodulated signal to generate a fingerprint image and obtain a biometric marker different from the fingerprint.

The above and other aspects, their implementations and applications are described in greater detail in the drawings, the description and the claims.

BRIEF DESCRIPTION OF THE DRAWINGS

FIG. 1 shows an example of a visible optical fingerprint sensor package in a mobile device and includes FIGS. 1A, 1B and 1C showing three different views of features in connection with the visible optical fingerprint sensor package.

FIGS. 12A, 12B, and 12C represent an exemplary fingerprint sensor module installed in a mobile device and implementing total reflection fingerprint detection scanning.

FIGS. 17, 18A and 18 B are diagrams showing an example of total reflection touch sensing-refractive index matching technique.

FIGS. 24A, 24B, 24C and 24D show process flow diagrams of an exemplary process for performing fingerprint sensing by a hybrid fingerprint sensor that incorporates optical and capacitive sensors.

DETAILED DESCRIPTION

Figure 2A:
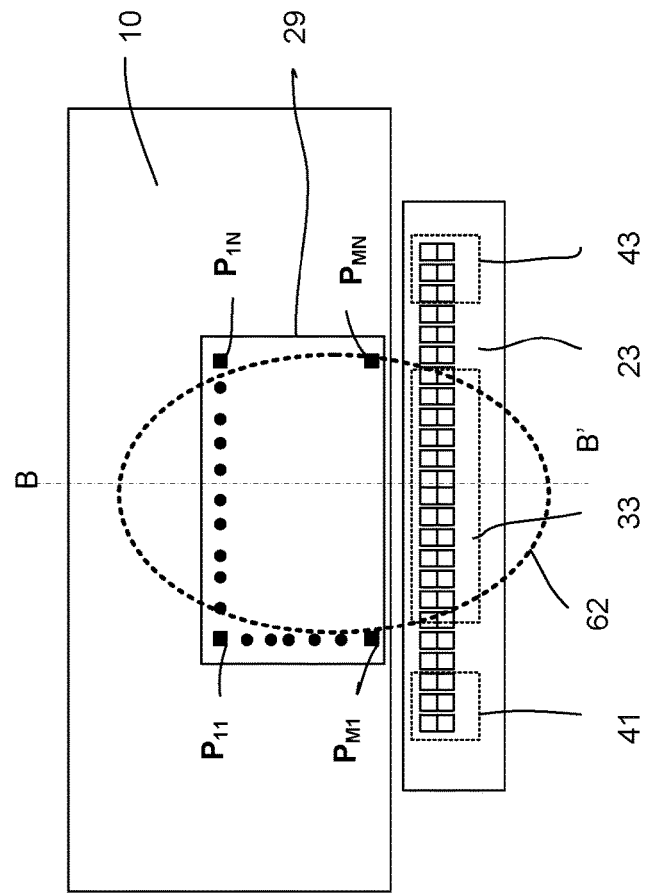
FIGS. 2A and 2B are block diagrams of an exemplary fingerprint sensing module in a visible package for installing in a mobile device, such as the mobile device of FIG. 1.

Fingerprint sensing is a useful use authentication tool in mobile applications and other applications that use, provide or require secure access. For example, fingerprint sensing can be used to provide secure access to a mobile device, an electronic device or system, or an electronic portal to one or more systems or databases, and can be used to secure financial transactions including online purchases and other digital information. It is desirable to include robust and reliable fingerprint sensors features suitable for mobile devices or portable devices while providing a small footprint for such fingerprint sensors with a thin structure to fit into the highly limited space in mobile or portable devices and other compact devices. In some applications, it is also desirable to include a protective cover to protect such a fingerprint sensor from various contaminants and to provide a user interface for touch sensing and certain user operations.

The technology disclosed in this patent document can be used to implement different types of fingerprint sensors either individually or in combinations, including capacitive fingerprint sensors and optical fingerprint sensors. In capacitive fingerprint sensors, the sensing is based on measuring the capacitance between the sensing electrode and a finger surface due to their capacitive coupling and variation in the capacitive coupling strength due to the surface topology of the fingerprint pattern including locations and shapes of fingerprint ridges and valleys. A protective cover can be placed over the capacitive sensor pixels to protect the capacitive fingerprint sensor. As this protective cover becomes thicker, the electrical field sensed by each capacitive sensor pixel disperses quickly in space, and the sensor signal strength received at each sensor pixel also reduces significantly with the increase in thickness of the protective cover. In addition, the increased protective cover thickness can lead to a undesirable steep reduction in the spatial resolution of the sensor. In some devices, when the protective cover thickness exceeds a certain threshold (e.g., 300 μm), it can become difficult for such capacitive sensors to provide a desired high spatial resolution in sensing fingerprint patterns and to reliably resolve a sensed fingerprint pattern with an acceptable fidelity.

As part of the disclosed technology in this patent document, a fingerprint sensor can also be implemented for optically capturing fingerprints. The thickness of an optical fingerprint module for optical fingerprint sensing tends to cause the optical fingerprint sensor to be too thick for certain applications or under certain technical or engineering constraints and the thickness of the optical fingerprint sensor tends to make integrating to a mobile phone device or a compact device difficult due to limitations or requirements in technology and engineering.

In one aspect, the disclosed technology provides a fingerprint sensor design for an ultrathin optical fingerprint sensor for integration into a mobile or compact device. In another aspect of the disclosed technology, a hybrid fingerprint sensor is provided to include both optical and capacitive sensors in each sensing pixel of a pixelated sensor array. The optical sensors can be packaged as photodiode arrays at a suitable location, including a detector location underneath of the display (e.g., or edges or a peripheral region of the display) or a location outside of but adjacent to the display. A window or a partially transparent coating can be used with or in the detectors. Examples of implementations of the disclosed technology can be used to introduce an optical technology for sensing finger properties including fingerprint detection. The optical fingerprint sensing technology can be used for a wide range of devices that have a display structure. The optical fingerprint sensing technology can be packaged in a discrete device in some designs.

Visible Optical Fingerprint Sensor Package

A visible optical fingerprint sensor package can be used to dispose one or more photodiode arrays of an optical fingerprint sensor on at one or more display side or edge positions outside the display screen area to make the presence of the optical fingerprint sensor "visible" on the device in the context that the optical fingerprint sensor module is partially or entirely outside the display screen area. A window or a partially transparent coating or cover can be used for the detector arrays in such a visual optical fingerprint sensor package.

FIG. 1 shows an example of a visible optical fingerprint sensor package in a mobile device with three different views of features in connection with the visible optical fingerprint sensor package. FIG. 1 includes three different views in FIGS. 1A (top view from the display side of the mobile device), 1B (side view along the line B-B' in FIG. 1A to show different layers in the fingerprint sensor) and 1C (showing some details of example of optical detector arrangement of the fingerprint sensor). Referring to FIG. 1A, this example of a mobile device includes a display assembly 10 with an integrated finger property sensor component. The display assembly 10 includes a display screen that can be implemented by a LCD screen, an OLED screen or other display screen designs. The display screen in the display assembly 10 an be a touch sensitive screen to provide a touch sensing user interface in operating the mobile device. Referring to FIG. 1B, the display assembly 10 includes an enhanced cover glass 50 on the top and other display layers 54 for the display screen disposed below the enhanced cover glass 50. As shown in FIG. 1A, reference number 12 indicates one example of a position of another sensor and two or more other sensors can be placed on the mobile device beyond the fingerprint sensor. The mobile device can also include optional user input mechanisms such as side buttons 14, 16 prepared for the smart terminals. Reference number 21 represents the fingerprint sensor zone, where the fingerprint sensor is located. Reference number 23 represents a detector array associated with the fingerprint sensor in some fingerprint sensor implementations (FIG. 1C). The fingerprint sensor zone 21 is located outside the display screen of the display assembly 10 at a selected location to allow the optical detectors within fingerprint sensor zone 21 for capturing fingerprints to be able to receive reflected or scattered light from a user's finger for the fingerprint sensing operations. As shown by the insert drawing in FIG. 1B, disposed above the optical detector array 23 are receiving optics 24 (e.g., optical lenses or optical collimators), which are the optical detectors for detecting light reflected off of a target, such as a finger. The receiving optics 24 above the photodetector array 23 can be in various configurations, e.g., it may include one or more lenses in some designs, optical collimators without lenses, or combining lenses and collimators. A back board 25 with integrated circuitry is disposed below the detector array 23 as shown in FIG. 1B. In some implementations, the detector array 23 can be integrated into the backboard 25. The backboard 25 can be disposed over a flexible printed circuit (FPC) 27. For the specific design shown in FIGS. 1A and 1B where the optical detector array 23 for the optical fingerprint sensing is placed next to one end of the display screen structure 54, a support glass 56 may be disposed at the other side of the optical fingerprint sensor module under the cover glass 50 to strengthen the mechanical strength of the overall assembly at the optical fingerprint sensor module area and to improve the structural integrity of the overall packaging. For devices that use the cover glass 50 with a high strength material or with a sufficient thick glass, this support glass 56 may be eliminated.

Referring back to FIG. 1A, located near the fingerprint sensor zone 21 within the display screen of the display assembly 10 is a specified display zone 29 for fingerprint detection on which a user places a user finger for the fingerprint detection based on optical fingerprint sensing by the underneath fingerprint sensor. This specified display zone 29 for fingerprint detection is part of the display screen and thus is used for both displaying images and for receiving fingerprint patterns from a user's finger. The specified display zone 29 for fingerprint detection as part of the display screen is located adjacent to the fingerprint sensor zone 21 located outside the display screen of the display assembly 10 so that the reflected or scattered light from the illuminated portion of the finger pressed against the display zone 29 can enter the fingerprint sensor zone 21 to reach the optical detector array 23 for optical sensing operations. As shown in FIG. 1B, a light path window 31 is disposed above the receiving optics and near the specified display zone 29 within the device display for fingerprint detection. The detector array 23 includes multiple detector elements arranged in different detector zones including a fingerprint detector zone 33 located in the central area of the detector array 23 for fingerprint and fingerprint property detection and one or more additional detector zones 41 and 43 for other optical sensing functions, where the additional detector zones 41 and 43, as illustrated in FIG. 1C, may be environment and blood flow detector zones 41 and 43 for environment and blood flow speed detection. In addition, reference numbers 37 and 39 represent additional specified zones that may be placed over an enhanced cover glass 50 for other optical sensing operations in some implementations, such as blood flow speed detection. In some implementations, each of the additional sensing zones 37 and 39 may include a patch of display pixels in the display screen structure 54 that can operate to produce desired illumination for the additional optical sensing, e.g., emitting red light or light of a desired spectral range to illuminate a user's finger for sensing blood flow speed or glucose level. This design represents an example where the light-emitting touch screen (e.g., an OLED touch screen) includes a fingerprint sensing zone 29 for a user to touch for fingerprint sensing to generate the returned light received by the optical detector array for detecting a fingerprint, a first optical sensing zone 37 and a second optical sensing zone 39 on two opposite sides of the zone 29 to provide for additional optical sensing beyond the fingerprint sensing.

As shown in FIG. 1B, this particular optical fingerprint sensor design is different from some other fingerprint sensor designs using a separate fingerprint sensor structure from the display screen with a physical demarcation between the display screen and the fingerprint sensor (e.g., a button like structure in an opening of the top glass cover in some mobile phone designs) on the surface of the mobile device. Under the illustrated design in FIG. 1B the fingerprint sensor zone 21 and the associated optical detector sensor module 23 for detecting fingerprint sensing and other optical signals are located under the top cover glass or layer 50 so that the top surface of the cover glass or layer 50 serves as the top surface of the mobile device as a contiguous and uniform glass surface across both the display screen of the display assembly 10 (containing the specified display zone 29 for fingerprint detection near the edge of the display screen) and the fingerprint sensor zone 21 and the associated optical detector sensor module 23. This design for integrating optical fingerprint sensing and the touch sensitive display screen under a common and uniform surface provides benefits, including improved device integration, enhanced device packaging, enhanced device resistance to failure and wear and tear, and enhanced user experience. This feature is also present in other implementations of the disclosed technology in this document. However, in some implementations of the optical sensing of fingerprints and other sensing operations, the optical sensor module may be packaged in a discrete device configuration in which the optical sensor module is a distinct structure that has a structural border or demarcation with the display screen, e.g., a button like fingerprint sensor structure in an opening of the top glass cover in some mobile phone designs based on all optical sensing or a hybrid sensing with both capacitive sensing and optical sensing.

A visible package of a fingerprint sensor can be used in any devices with display or similar light sources. The optical sensing in FIG. 1 is based on illumination of a user's finger. Different illumination mechanisms may be used. For example, in some implementations, the display elements of the display screen that are located within the several zones 29, 37, 39 in FIG. 1A within the display screen for optical sensing can be used to illuminate the user's finger. The light from such display elements of the display screen is used to form part of the displayed images on the display screen as part of the mobile device operation and the light, after transmitting through the top layer of the screen, will illuminate the user's finger to cause reflected or scattered light from the illuminated finger to allow optical sensing by the detector array 23 and other detectors 41, 43, 37 and 39. A suitable display screen for implementing the disclosed optical sensor technology can be based on various display technologies or configurations, including, a display screen having light emitting display pixels without using backlight where each individual pixel generates light for forming a display image on the screen such as an organic light emitting diode (OLED) display screens or electroluminescent display screens. The disclosed optical sensor technology may also be adapted for use with other display screens, such as LCD display screens which use one or more illumination light sources (e.g., LEDs) to produce illumination light in a backlighting or edge lighting configuration to illuminate the LCD display pixels which filter and modulate the illumination light at each LCD pixel to display the images.

When the display illumination light is used to illuminate the user's finger for optical sensing of the user's fingerprint or other biometric parameters, the light from the display, which can be directly emitted by display pixels (e.g., OLED display pixels) or can be optically filtered by the display pixels (e.g., LED display pixels based on backlighting or edge lighting designs), contains different colors, e.g., red (575 nm-660 nm), green (490 nm-575 nm) and blue (410 nm-490 nm) light. For optical sensing other than fingerprints, such as the blood flow speed or heartbeat rate, the optical wavelength for the light that illuminates the user's finger may be selected at certain optical wavelengths, e.g., in the red spectra for sensing a user's blood to obtain the heartbeat rate, the oxygen level, the glucose level and others. In an OLED display screen, each display color pixel includes at least OLED pixels at three different colors and the red light from red color OLED pixels can be to measure the blood information of a user.

Several integrated detector arrays 23, 33, 41, 43 (e.g. photo diodes) can be used to detect the light scattered from the finger tissues and detect the light in the environment. The detector arrays 23, 33, 41, 43 can be placed and packaged close to the specified display zones 29, 37, 39 to enhance the light detection efficiency. Depending on the applications and specific device designs, the positions of the specified display zones shown in FIG. 1 may be modified from the exemplary locations as shown in FIG. 1A and be placed at other suitable locations on the display assembly 10.

In various implementations, one or more other light sources may be used to produce light to illuminate a user's finger for optically sensing the fingerprints or other biometric parameters of the user. Such light for optical sensing is different and separate from the display illumination light that is either emitted by display pixels (e.g., OLED display pixels) or is directed from illumination light sources to the display pixels (e.g., LED display pixels based on backlighting or edge lighting designs). The one or more light sources for optical sensing may be integrated into the display or the mobile device in FIG. 1 to provide special illumination to the user's finger for optical sensing. The optical wavelength of such light sources for optical sensing can be selected to meet the optical sensing requirements. For example, one or more red light sources may be used to illuminate red light onto the user's finger for optical sensing of blood information of the user. The illumination light from such other light sources can be modulated to improve the optical sensing detection. For example, the display light sources can be modulated with a proper pattern so as to reject background light during detection. The sensor module can detect fingerprint, heartbeat, and blood flow speed etc. If specified wavelengths light sources are integrated into the display, the sensor module can monitor other bio-parameters, such as glucose and degree of blood oxygen saturation.

Figure 2B:
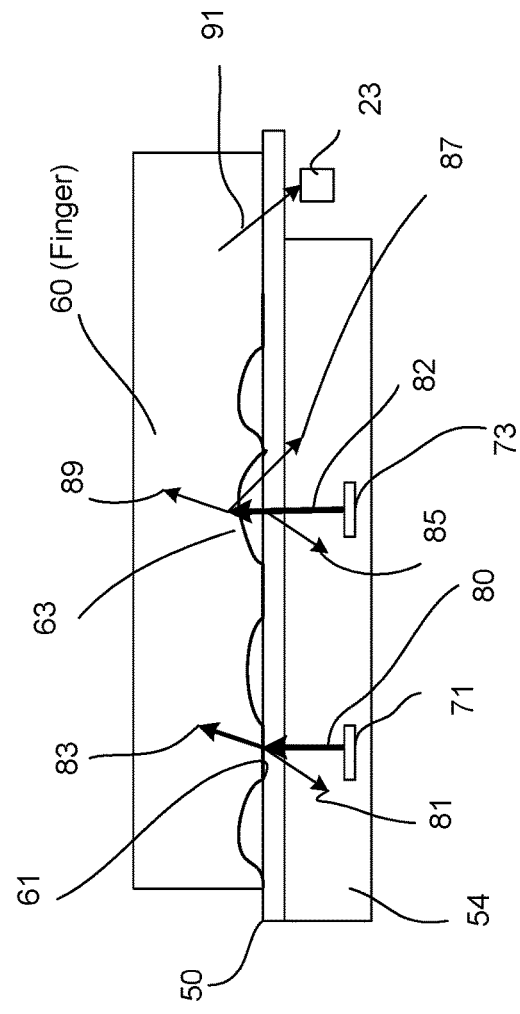

FIGS. 2A and 2B are block diagrams of an example of a fingerprint sensing module in a visible fingerprint sensor package for installing in a mobile device, such as the mobile device of FIG. 1. FIG. 2A is a top-down view of the fingerprint sensing module in the visible package. FIG. 2B is a side view along a direction that is parallel to the display screen surface showing an exemplary fingerprint sensing operation based on detecting returned light by the optical detector array 23. As shown in FIG. 2A, the display assembly 10 with the integrated finger property sensor includes a specified display zone 29 for fingerprint detection. Reference number 62 represents a finger pressing on the sensor. Similar to FIG. 1, the detector array 23 disposed near the specified display zone 29 includes multiple detector elements including detector elements in the fingerprint detector zone 33 for fingerprint sensing and fingerprint property detection responsive to the finger 62 pressing on the sensor. The detector array 23 also includes detector elements in the environment and blood flow zones 41 and 43 for environment and blood flow speed detection. Examples of the detector elements of the detector array 23 include optical devices such as photodiodes.

As shown in FIG. 2B, the display assembly 10 with an integrated finger property sensor component includes a cover glass 50 and other display layers 54. Display elements 71 and 73 of the display screen within the display assembly 10 can be disposed in the display layers 54 and are operated to emit modulated light to display images on the display. In addition to their functions for displaying images, the light from the display elements 71 and 73 exiting the top surface of the display screen in the specified display zone 29 for fingerprint detection near the edge of the display screen is also used to illuminate a user's finger pressed in the zone 29 to create reflected or scattered light from the finger towards the optical detector array 23 for fingerprint sending and other optical sensing operations. Examples of display elements 71 and 73 include various types of light emitting devices such as light emitting diodes (LEDs) and organic LEDs (OLEDs). Also, the detector array 23 is disposed below the cover glass 50. Light beams 80 and 82 emitted from the display elements 71 and 73 interface with the cover glass 50, some of which pass through the top glass 10 and interface with different parts of the finger 60. For example, at least some of the light beam 80 emitted from display element 71 can pass through the cover glass 50 and interface with finger skin ridge 61. A portion of the light beam 80 that interface with the finger skin ridge 61 is light 83 that is coupled or absorbed into the finger tissues 60. Another portion of the light beam 80 is a reflected light 81 that reflects off of the cover glass 50.

A portion of the light beam 82 emitted from the display element 73 passes through the cover glass 50 and interfaces with finger skin valley 63. The portion of the light beam 82 that interfaces with the finger skin valley 63 is shown as light 89 that is coupled or absorbed into finger tissues 60. Another portion of the light beam 82 is shown as a reflected light 85 that reflects off of the cover glass 50. Yet another portion of the light beam 82 is shown as a finger skin reflected light 87 that reflects off of the finger skin valley 63. Yet another portion of the light beam 82 ends up as scattered light 91 that scatters into the detector array 23, such as photodiodes.

The display elements 71 and 73 in the specified zone 29 and the detector elements in zone 33 are used to measure the fingerprint. The detector elements in zone 41 or 43, or both 41 and 43 are used to monitor the environment light illumination. The display elements in the specified zone 29 are formed in one or more patterns appropriate for fingerprint, environment, and blood flow detection. For example, display elements in zone 29 can be divided into small groups, each group having an appropriate number of detector elements. The small groups of detector elements can be turned on in turn to illuminate the finger placed on or close to the sensor zones. The detector elements in the detector array 23 detect the scattered light 91 scattered from the finger. The detector signals from the detector array 23 elements in zone 33 carry the fingerprint information. The detector signals from the detector element sin zone 41, 43, or both are used to calibrate the fingerprint signal from zone 33 so as to eliminate the influence of the environment light including the influence from other display zones.

As illustrated in FIGS. 2A and 2B, responsive to a finger placed on the display screen and the photodiode area, display elements or light sources 71 and 73 can emit light toward the finger to perform fingerprint and fingerprint properties detection. Finger skin's equivalent index of refraction is about 1.43 at 633 nm. Typical bare cover glass index of refraction is about 1.51. When some of the display elements 71 are illuminated at the finger skin ridge locations 61, the finger ridge-cover glass interface reflected light 81 consumes very little power (~0.1%) of the incident light 80. The majority of the light beam 80 is transmitted 83 into the finger tissues 60. A portion of the light 80 is scattered 91 into the photo diode array 23.

When some of the display elements 73 are illuminated at the finger skin valley locations 63, the cover glass surface reflects about 3.5% of the incident light 82 as reflected light 85, and the finger valley surface reflects about 3.3% of the incident light as reflected light beam 87. In total, about 6.8% of the light 82 is lost by the surface reflection. The majority of the light 82 is transmitted 89 into the finger tissues 60. A portion of the light 82 is scattered 91 into the photo diode array 23. The surface reflection ratio difference between the finger valley and finger ridge carries the fingerprint map information.

The display elements 71 and 73 can be turned on in sequence using a modulation pattern, for example, with different codes at different locations. Also, the detector arrays 23 of photodiodes can be synchronized with the display scanning. The modulation pattern of the display elements 71 and 73, the detector array 23 synchronization, or both can be used to acquire a sequence of signals. The sequence of signals can be demodulated to acquire a map of the finger ridges and valleys by comparing the amplitudes of the signals.

When the distance between the illuminated display elements and the detectors (e.g., photodiodes) changes, the light absorption of the finger tissues also changes so that the photodiode detected light power is affected. Adjusting the brightness of the display elements 71 and 73 can calibrate or eliminate the influence of the change in the distance between the illuminated display elements and the detectors. For example, the display elements that are further away from the detector array can be illuminated to be brighter than display elements that are closer to the detector array 23. Due to the divergence of the display element emitted light beam, and to enhance the fingerprint image contrast, the display elements, such as RGB (red green blue) elements are set close to the finger skin or the light beam is collimated.

Figure 3:
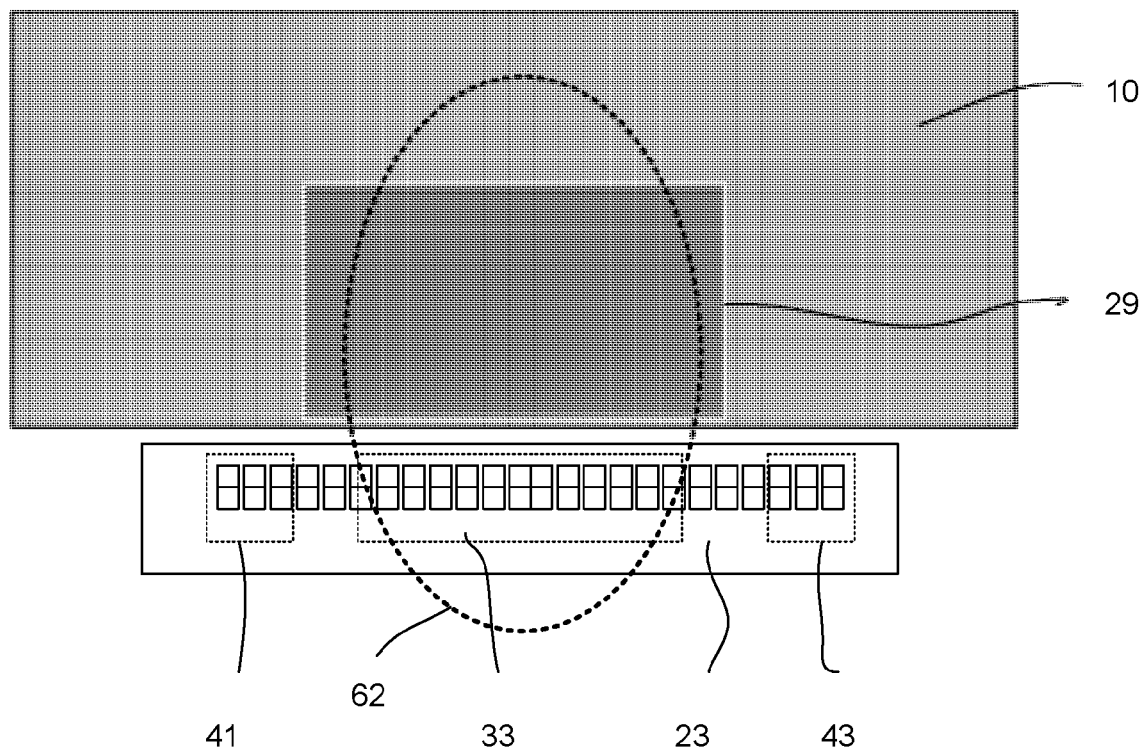
FIG. 3 is a block diagram of an exemplary fingerprint sensing module in a visible package for heartbeat sensing.

FIG. 3 is a block diagram of an exemplary fingerprint sensing module in a visible package for heartbeat sensing. The fingerprint sensing module includes a display assembly 10 with in integrated finger property sensor component. Detector array 23 is disposed near the display assembly and positioned to receive reflected or scatter light caused by a contact to the top cover surface by a finger 62. A specified display zone 29 for fingerprint detection is designated on the display assembly 10 at a location within the display screen near the detector array 23. In response to a touch, the display pixels in the display zone 29 are turned on to project light towards the top cover surface of the display to illuminate the top cover surface area within the display zone 29 to illuminate the user's finger 62. A portion of the reflected or scattered light from the user's finger 62 in touch with the top cover surface in the display zone 29 can reach the nearby detector array 23. The detector array 23 includes detector elements in the fingerprint detector zone 33 for fingerprint and fingerprint property detection. Detector elements in zones 41 and 43 are for environment and blood flow speed detection.

To detect the heartbeat signals, more display elements are turned on simultaneously so as to generate sufficient incident light power for the optical sensing of the heartbeat signals. The finger tissue light absorption ratio varies with the blood flow which is controlled by the heartbeat. The light absorption fluctuation signal reflects the heartbeat rate. In the disclosed technology, the light wavelength of the light emitted by the display elements may be selected to optimize the detection. Also, the light illumination may be modulated at a frequency so as to further reduce the influence of the environment. For example, the specified display zone can be operated at a very high frame rate so as to realize the modulation. In some implementations, the light sources of the display can be modulated. In some implementations, extra modulated light sources can be integrated into the display assembly 10. Performing heartbeat sensing simultaneously with the fingerprint acquiring can greatly improve the secure access of the mobile device by differentiating between a fake fingerprint and a fingerprint from a live finger.

Figure 4:
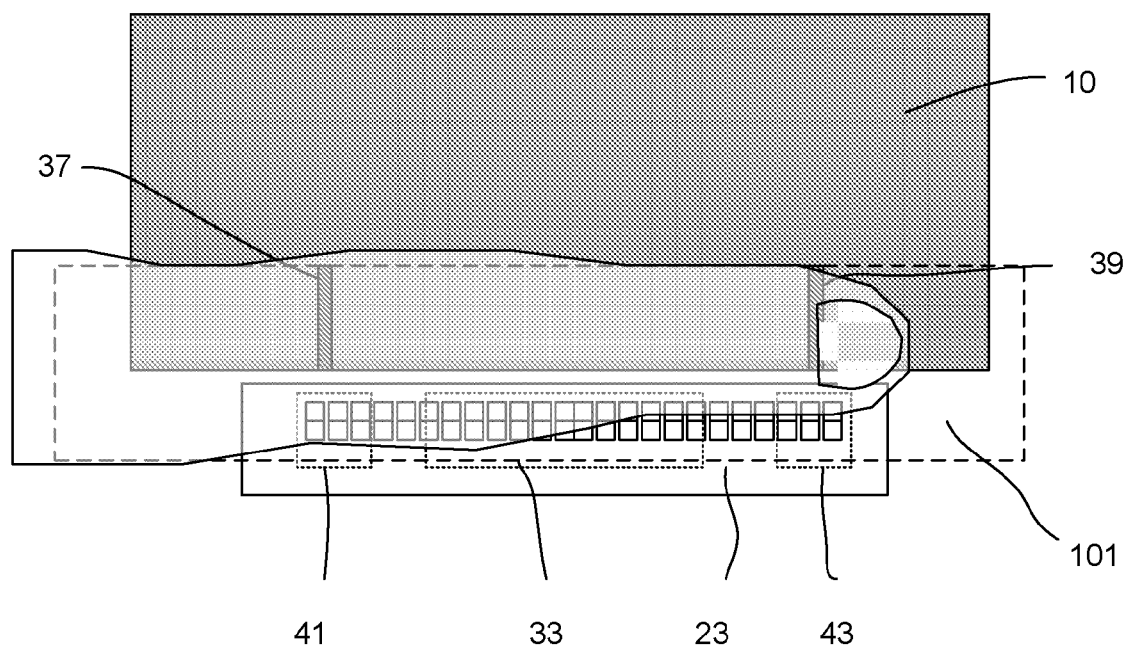
FIG. 4 is a block diagram of an exemplary fingerprint sensing module in a visible package for blood flow speed sensing.

FIG. 4 shows an exemplary fingerprint sensing module in a visible package for blood flow speed sensing. The fingerprint sensing module includes a display assembly 10 with in integrated finger property sensor component. Detector array 23 is disposed near the display assembly and positioned to receive a finger 101 to be monitored. The detector array 23 includes detector elements in the fingerprint detector zone 33 for fingerprint and fingerprint property detection. Detector elements in zones 41 and 43 are for environment and blood flow speed detection. The display assembly 10 also includes specified zones 37 and 39 within the display screen area for blood flow speed detection.

In FIG. 4, the fingerprint sensor assembly is structured to receive the finger on the sensor area 101, with one side overlapping with display elements in zone 37 and 39 and the other side overlapping with the detectors (e.g., photodiodes) in zone 41 and 43 respectively. Display elements in zone 37 and detectors in zone 41 cooperate to measure the pulse signals at one position of the finger. Display elements in zone 39 and detectors in zone 43 cooperate to measure the pulse signals at the other position of the finger. The pulsation signal is generated in the arteries. In FIG. 4, a finger can be placed along the direction of the two zones 37 and 39 as illustrated. The blood flowing in the arteries is detected at the left zone 37 and the right zone 39 representing the blood flowing across the zones from the left zone 37 to right zone 39. When the blood flows back from the right zone 39 to the left zone 37, the blood flows in the veins and no pulsation signal is obvious. By comparing the pulsation delay time between the two locations 37 and 39, the blood flow speed information can be acquired. Because blood pressure is correlated with blood flow speed, the sensor shown in FIG. 4 can also monitor the blood pressure.

In some implementations, the illumination light emitted by the display elements may be modulated to reduce or eliminate background noise. For example, the emitted light can be modulated at a predetermined frequency so as to further reduce the influence of the environmental conditions. Frequency modulating the emitted light can include operating the display elements in the specified display zone at very high frame rate to achieve a desired modulation. Also, the display light sources can be modulated. In some implementations, specified modulated light sources can be integrated into the display assembly 10.

Figure 5:
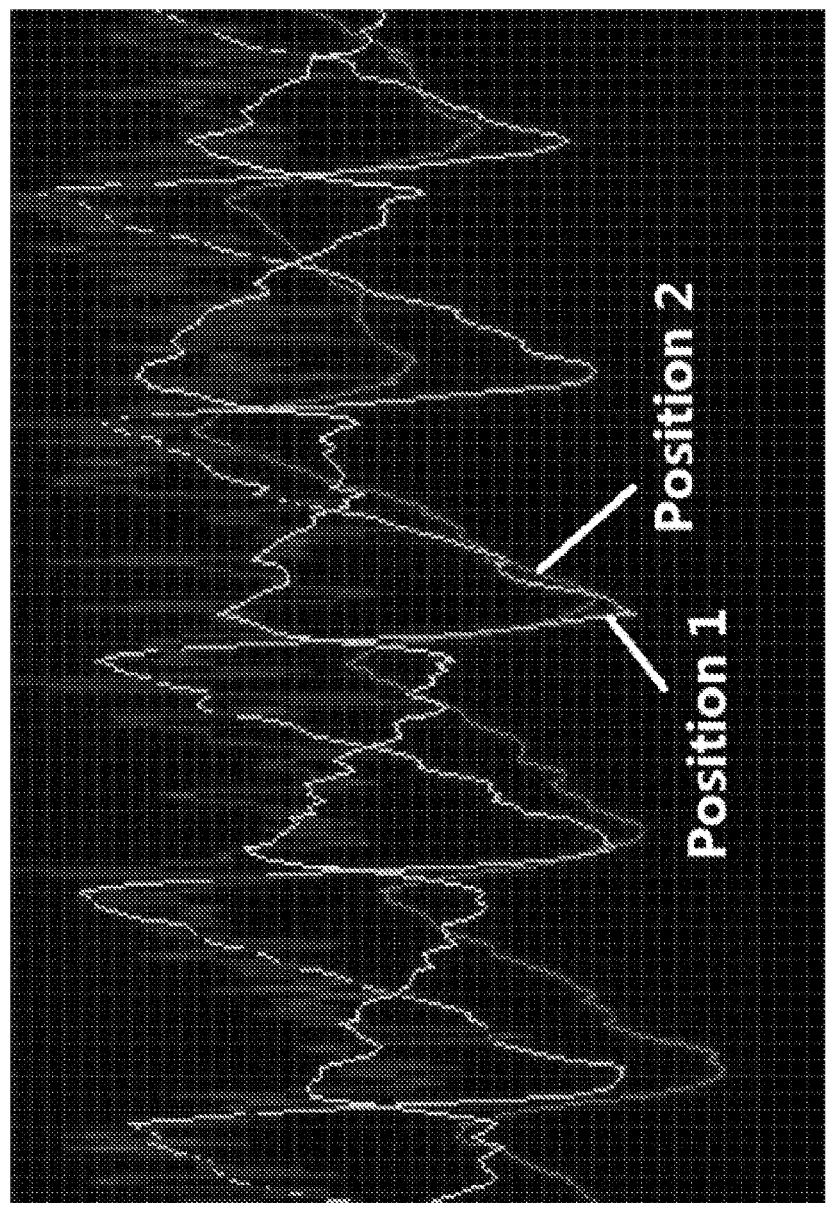
FIG. 5 is a graph showing an exemplary signals from blood flow speed sensing.

FIG. 5 is a graph showing an exemplary signals from blood flow speed sensing performed in FIG. 4. FIG. 5 shows that there is a time delay between two positions (e.g., Position 1 and Position 2) along a finger in the signals measured by the sensor module in FIG. 4. The typical blood flow speed in a person is approximately 20 cm per second in the finger's major arteries. If the distance between the two positions is approximately 20 mm, the time delay is approximately 100 ms. This time delay can be detected using the fingerprint sensor module disclosed in FIG. 4 and other designs in this document.

Invisible Optical Fingerprint Sensor Package

The above disclosed optical sensing functions associated with fingerprint sensing and other biometric marker sensing can be alternatively achieved by using an "invisible" optical fingerprint sensor package to match one or more detector arrays (e.g., an array containing photodiodes) directly under the display so that the optical fingerprint sensor package is underneath the device display screen. Because the optical sensing module are now underneath of the display screen and is hidden from the plain view from the top surface of the mobile phone, this design is an "invisible" optical fingerprint sensor package. Implementations of this under-screen optical fingerprint sensing package may be used to eliminate the need for a window opening or designated area for the fingerprint sensor module so that the entire top surface of the mobile device may be used for enlarging the display screen size while still providing optical sensing of fingerprints and other biometric marker measurements.

Figure 6C:
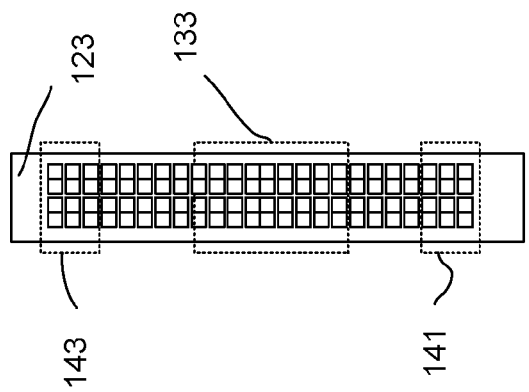
FIG. 6 is a block diagram showing an example of an invisible optical fingerprint sensor package in a mobile device and FIGS. 6A, 6B and 6C showing three different views of features in connection with the invisible optical fingerprint sensor package.
Figure 6A:
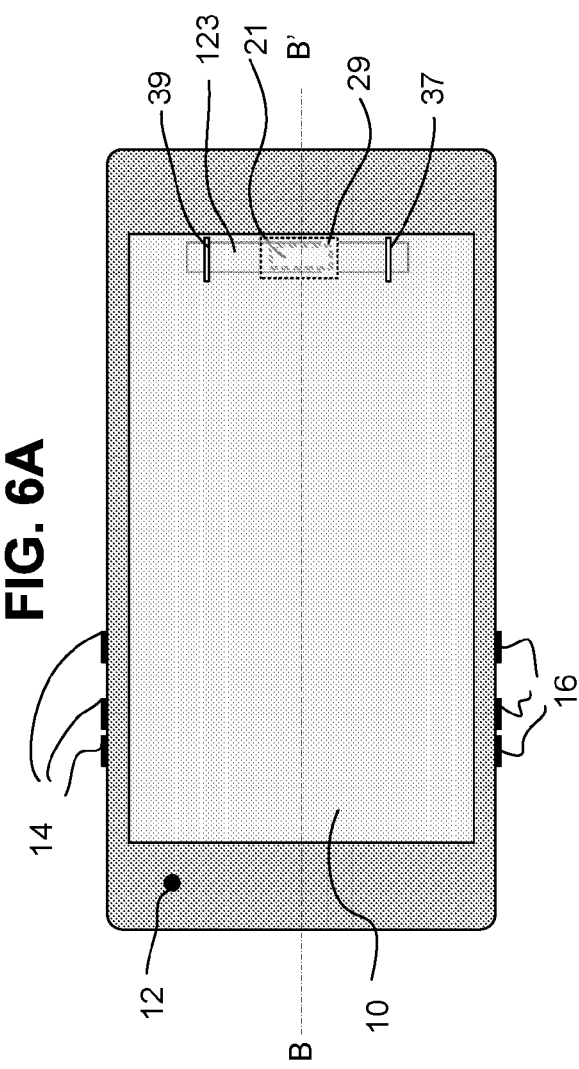
Figure 6B:
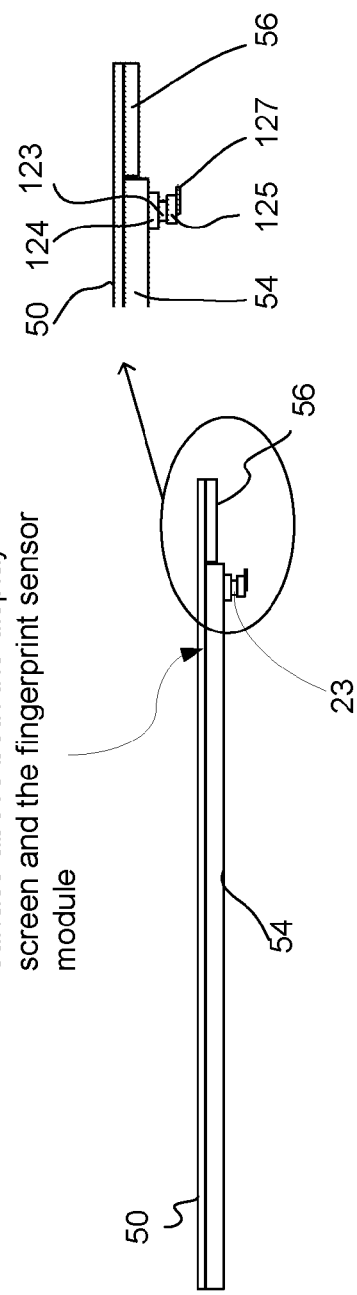

FIG. 6 is a block diagram showing an example of an invisible optical fingerprint sensor package in a mobile device. FIG. 6 includes three different views in FIGS. 6A (top view from the display side of the mobile device), 6B (side view along the line B-B' in FIG. 6A to show different layers in the fingerprint sensor) and 6C (showing some details of example of optical detector arrangement of the fingerprint sensor). Referring to FIG. 1A, the mobile device utilizing the invisible package of the fingerprint sensor includes a display assembly 10 with an integrated finger property sensor component. Reference number 12 indicates one or more other sensors on the mobile device. The mobile device can also include user input mechanisms such as side buttons 14, 16 prepared for the smart terminals. Reference number 21 represents the fingerprint sensor zone, where the fingerprint sensor is located below the display screen. Located near the fingerprint sensor zone 21 is a specified display zone 29 within the display screen for fingerprint detection for receiving and illuminating a user's finger and thus may be referred to as the illumination zone 29. The zone 21 may overlap or partially overlap the illumination zone 29 to receive part of reflected or scattered light from the illuminated finger in touch with the illumination zone 29. As shown in FIG. 6B, reference number 123 represents an optical detector array associated with the fingerprint sensor. Disposed above the detector array 123 are receiving optics 124, which are the optical detectors for detecting light reflected off of a target, such as a finger. A back board with integrated circuitry is disposed below the detector array. In some implementations, the detector array 123 can be integrated into the backboard 125. The backboard 125 can be disposed over a flexible printed circuit (FPC) 127.

The detector array 123 includes multiple detector elements arranged in different detector zones including fingerprint detector zone 133 for fingerprint and fingerprint property detection and environment and blood flow detector zones 141 and 143 for environment and blood flow speed detection. Referring to FIG. 6C, reference numbers 37 and 39 represent specified zones over an enhanced cover glass 50 for blood flow speed detection. The display assembly 10 includes the enhanced cover glass 10 and other display layers 54 disposed below the enhanced cover glass 50. A support glass 56 may be disposed under the cover glass 50 in some implementations.

As shown in FIG. 6B, the fingerprint sensor zone 21 and the associated optical detector sensor module 123 for detecting fingerprint sensing and other optical signals are located under the top cover glass or layer 50 so that the top surface of the cover glass or layer 50 serves as the top surface of the mobile device as a contiguous and uniform glass surface across both the display screen of the display assembly 10 (containing the specified display zone 29 for fingerprint detection near the edge of the display screen) and the fingerprint sensor zone 21 and the associated optical detector sensor module 123.

The invisible optical fingerprint sensor package can be used in any devices with display or similar light sources. The display elements of several zones 29, 37, 39 are used to illuminate the user's finger. Several integrated detector (e.g., photodiode) arrays 123, 133, 141, 143 underneath the display screen are used to detect the light scattered from the finger and detect the light in the environment. The photodiode arrays 123, 133, 141, 143 are packaged close to the specified display zones 29, 37, 39 and fixed under the display assembly 10 so as to achieve a high light detection efficiency. The positions of the specified display zones 29, 37, 39 are not limited to the examples shown in FIG. 6, and can be adjusted to be placed at various suitable locations to perform fingerprint detection and other optical sensing operations.

Like the design in FIG. 1, the illumination light for the optical fingerprint sensing and other optical sensing can be provided in different ways. In some implementations, the display pixels may be used to provide the illumination light to the finger. In other implementations, additional light sources can be integrated into the display to provide special illumination. Also, the added light sources can be modulated. For example the display light sources can be modulated using an appropriate pattern so as to reject background light during the detection.

The sensor module as shown in FIG. 6 can detect fingerprints and additional biometric markers, such as heartbeat and blood flow speed. If light sources of certain specified wavelengths are integrated into the display, the sensor module can further monitor additional bio-parameters, such as glucose and degree of blood oxygen saturation.

Figure 7A:
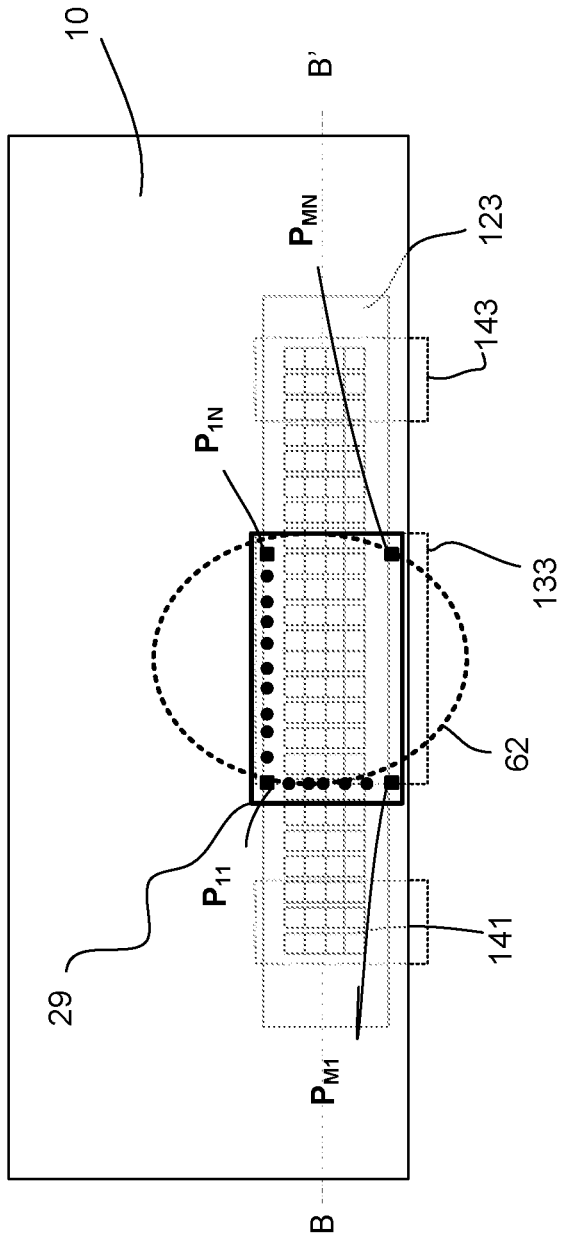
FIGS. 7A and 7B are block diagrams of an exemplary fingerprint sensing module in an invisible package for installing in a mobile device, such as the mobile device of FIG. 6.
Figure 7B:
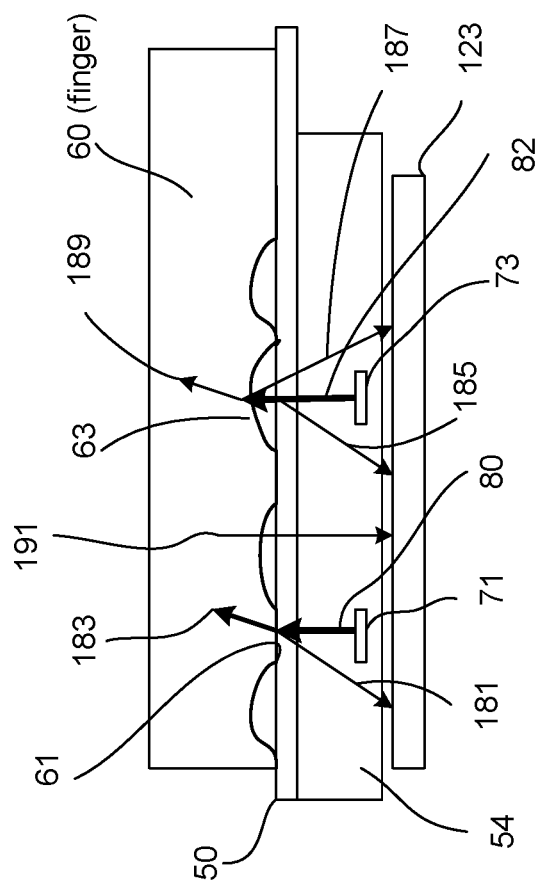

FIGS. 7A and 7B are block diagrams of an exemplary fingerprint sensing module in an invisible package for installing in a mobile device, such as the mobile device of FIG. 6. FIG. 7A is a top-down view of the fingerprint sensing module in the visible package. FIG. 7B is a block diagram showing a cross sectional view of the invisible optical fingerprint sensor package along the line B-B' in FIG. 7A and further illustrates an exemplary fingerprint sensing operation. As shown in FIG. 7A, the display assembly 10 with the integrated finger property sensor includes a specified display zone 29 for fingerprint detection. Reference number 62 represents a finger pressing on the sensor. Similar to FIG. 6, the detector array 123 disposed near the specified display zone 29 includes multiple detector elements including detector elements in the fingerprint detector zone 133 for fingerprint and fingerprint property detection responsive to the finger 62 pressing on the sensor. The detector array 123 also includes detector elements in the environment and blood flow zones 141 and 143 for environment and blood flow speed detection. Examples of the detector elements of the detector array 123 include optical devices such as photodiodes.

As shown in FIG. 7B, the display assembly 10 with an integrated finger property sensor component includes a cover glass 50 and other display layers 54. Display elements 71 and 73 can be disposed in the other display layers 54. Examples of display elements 71 and 73 include various types of light emitting devices such as light emitting diodes (LEDs). Also, the detector array 123 is disposed below the cover glass 50. Light beams 80 and 82 emitted from the display elements 71 and 73 interface with the cover glass 50, some of which pass through the top glass 10 and interface with different parts of the finger 60. For example, at least some of the light beam 80 emitted from display element 71 can pass through the cover glass 50 and interface with finger skin ridge 61. A portion of the light beam 80 that interface with the finger skin ridge 61 is light 183 that is coupled or absorbed into the finger tissues 60. Another portion of the light beam 80 is a reflected light 181 that reflects off of the cover glass 50.

A portion of the light beam 82 emitted from the display element 73 passes through the cover glass 50 and interfaces with finger skin valley 63. The portion of the light beam 82 that interfaces with the finger skin valley 63 is shown as light 189 that is coupled or absorbed into finger tissues 60. Another portion of the light beam 82 is shown as a reflected light 185 that reflects off of the cover glass 50. Yet another portion of the light beam 82 is shown as a finger skin reflected light 187 that reflects off of the finger skin valley 63. Yet another portion of the light beam 82 ends up as scattered light 191 that scatters into the detector array 123, such as photodiodes.

The display elements 71 and 73 in the specified zone 29 and the detector elements in zone 133 are used to measure the fingerprint. The detector elements in zone 141, 143, or both 141 and 143 are used to monitor the environment light illumination. The display elements in the specified zone 29 are formed in one or more patterns appropriate for fingerprint, environment, and blood flow detection. For example, display elements in zone 29 can be divided into small groups, each group having an appropriate number of detector elements. The small groups of detector elements can be turned on in turn to illuminate the finger placed on or close to the sensor zones. The detector elements in the detector array 23 detect the scattered light 91 scattered from the finger. The detector signals from the detector array 23 elements in zone 133 carry the fingerprint information. The detector signals from the detector element sin zone 141, 143, or both are used to calibrate the fingerprint signal from zone 133 so as to eliminate the influence of the environment light including the influence from other display zones.

As illustrated in FIGS. 7A and 7B, responsive to a finger placed on the display screen and the photodiode area, display elements or light sources 71 and 73 can emit light toward the finger to perform fingerprint and fingerprint properties detection. Finger skin's equivalent index of refraction is about 1.43 at 633 nm. Typical bare cover glass index of refraction is about 1.51. When some of the display elements 71 are illuminated at the finger skin ridge locations 61, the finger ridge-cover glass interface reflected light 181 consumes very little power (~0.1%) of the incident light 80. The majority of the light beam 80 is transmitted 83 into the finger tissues 60. A portion of the light 80 is scattered 191 into the photo diode array 123.

When some of the display elements 73 are illuminated at the finger skin valley locations 63, the cover glass surface reflects about 3.5% of the incident light 82 as reflected light 185, and the finger valley surface reflects about 3.3% of the incident light as reflected light beam 187. In total, about 6.8% of the light 82 is lost by the surface reflection. The majority of the light 82 is transmitted 189 into the finger tissues 60. A portion of the light 82 is scattered 191 into the photo diode array 23. The surface reflection ratio difference between the finger valley and finger ridge carries the fingerprint map information.

The display elements 71 and 73 can be turned on in sequence using a modulation pattern, for example, with different code at different locations. Also, the detector arrays 123 of photodiodes can be synchronized with the display scanning. The modulation pattern of the display elements 71 and 73, the detector array 123 synchronization, or both can be used to acquire a sequence of signals. The sequence of signals can be demodulated to acquire a map of the finger ridges and valleys by comparing the amplitudes of the signals.

When the distance between the illuminated display elements and the detectors (e.g., photodiodes) changes, the light absorption of the finger tissues also changes so that the photodiode detected light power is affected. Adjusting the brightness of the display elements 71 and 73 can calibrate or eliminate the influence of the change in the distance between the illuminated display elements and the detectors. For example, the display elements that are further away from the detector array can be illuminated to be brighter than display elements that are closer to the detector array 123. Due to the divergence of the display element emitted light beam, and to enhance the fingerprint image contrast, the display elements, such as RGB (red green blue) elements are set close to the finger skin or the light beam is collimated.

Figure 8:
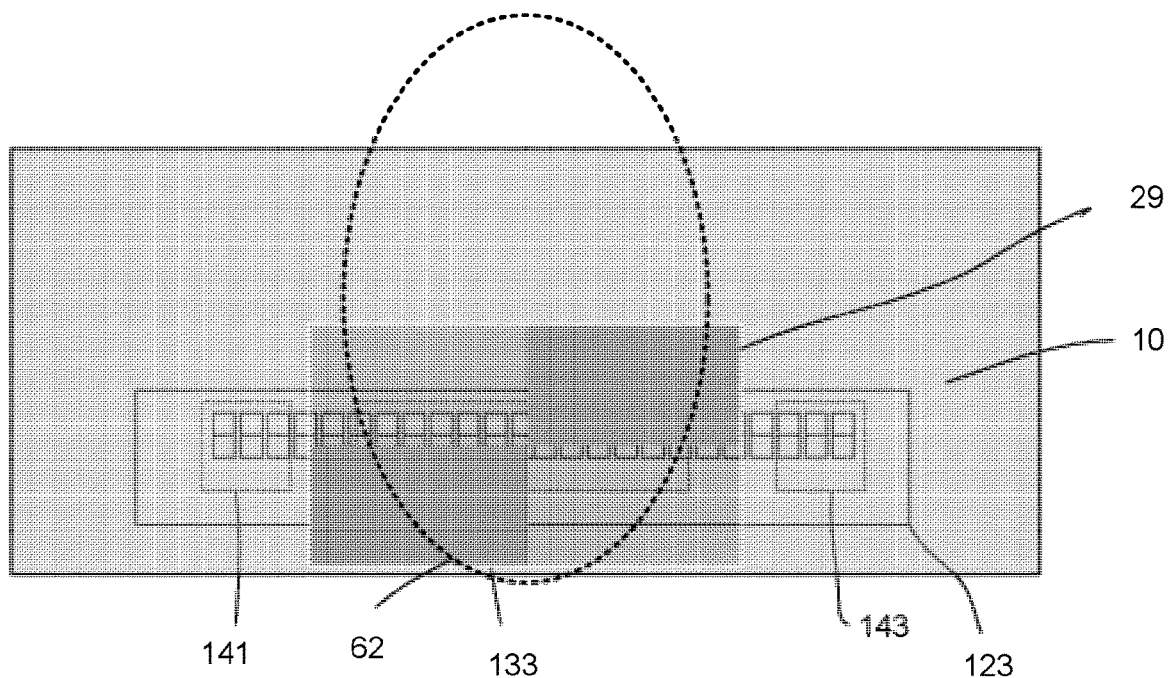
FIG. 8 is a block diagram of an exemplary fingerprint sensing module in an invisible package for heartbeat sensing.

FIG. 8 is a block diagram of an exemplary fingerprint sensing module in an invisible package for heartbeat sensing. The fingerprint sensing module includes a display assembly 10 with in integrated finger property sensor component. Detector array 123 is disposed near the display assembly and positioned to receive a contact by a finger 62. A specified display zone 29 for fingerprint detection is disposed on the display assembly 10 to be arranged near the detector array 123. The detector array 123 includes detector elements in the fingerprint detector zone 133 for fingerprint and fingerprint property detection. Detector elements in zones 141 and 143 are for environment and blood flow speed detection.

To detect the heartbeat signals, more display elements are turned on simultaneously so as to generate enough incident light power. The finger tissue light absorption ratio varies with the blood flow which is controlled by the heartbeat. The light absorption fluctuation signal reflects the heartbeat rate. In the disclosed technology, the light wavelength of the light emitted by the display elements may be selected to optimize the detection. Also, the light illumination may be modulated at a frequency so as to further reduce the influence of the environment. For example, the specified display zone can be operated at a very high frame rate so as to realize the modulation. In some implementations, the light sources of the display can be modulated. In some implementations, extra modulated light sources can be integrated into the display assembly 10. Performing heartbeat sensing simultaneously with the fingerprint acquiring can greatly improve the secure access of the mobile device by differentiating between a fake fingerprint and a fingerprint from a live finger.

Figure 9:
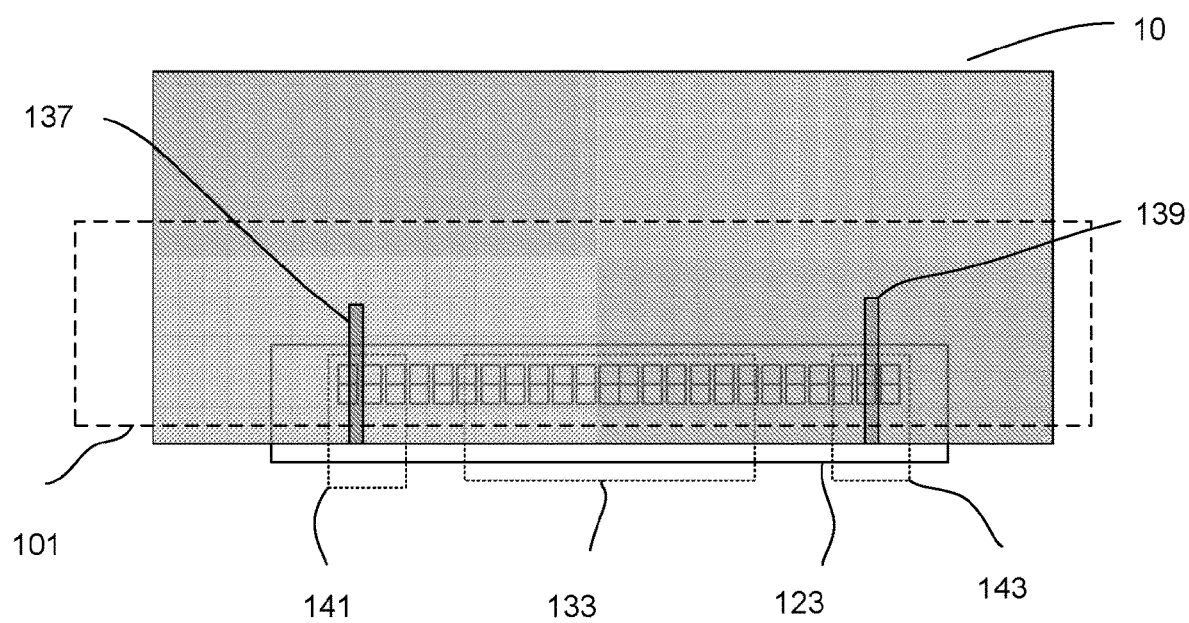
FIG. 9 is a block diagram of an exemplary fingerprint sensing module in an invisible package for blood flow speed sensing.

FIG. 9 is a block diagram of an exemplary fingerprint sensing module in an invisible package for blood flow speed sensing. The fingerprint sensing module includes a display assembly 10 with in integrated finger property sensor component. Detector array 123 is disposed near the display assembly and positioned to receive a finger 101 to be monitored. The detector array 123 includes detector elements in the fingerprint detector zone 133 for fingerprint and fingerprint property detection. Detector elements in zones 141 and 143 are for environment and blood flow speed detection. The display assembly 10 also includes specified zones 137 and 139 for blood flow speed detection.

As illustrated in FIG. 9, the fingerprint sensor assembly is structured to receive the finger on the sensor area 101, with one side overlapping with display elements in zone 137 and 139 and the other side overlapping with the detectors (e.g., photodiodes) in zone 41 and 43 respectively. Display elements in zone 137 and detectors in zone 141 cooperate to measure the pulse signals at one position of the finger. Display elements in zone 139 and detectors in zone 143 cooperate to measure the pulse signals at the other position of the finger. The pulsation signal is generated in the arteries. In FIG. 9, the blood flowing in the arteries is detected at the left zone 137 and the right zone 139 representing the blood flowing across the zones from the left zone 137 to right zone 139. When the blood flows back from the right zone 139 to the left zone 137, the blood flows in the veins and no pulsation signal is obvious. By comparing the pulsation delay time between the two locations 137 and 139, the blood flow speed information can be acquired. Because blood pressure is correlated with blood flow speed, the sensor shown in FIG. 9 can also monitor the blood pressure.

In some implementations, the illumination light emitted by the display elements may be modulated to reduce or eliminate background noise. For example, the emitted light can be modulated at a predetermined frequency so as to further reduce the influence of the environmental conditions. Frequency modulating the emitted light can include operating the display elements in the specified display zone at very high frame rate to achieve a desired modulation. Also, the display light sources can be modulated. In some implementations, specified modulated light sources can be integrated into the display assembly 10.

Total Optical Reflection Fingerprint Sensing

In another aspect, the total optical reflection effect at the cover glass of the mobile device can be used to acquire the fingerprint signals. The detector array can be integrated directly under the display in some situations such as OLED display, or fixed at the display edge positions.

Figure 10A:
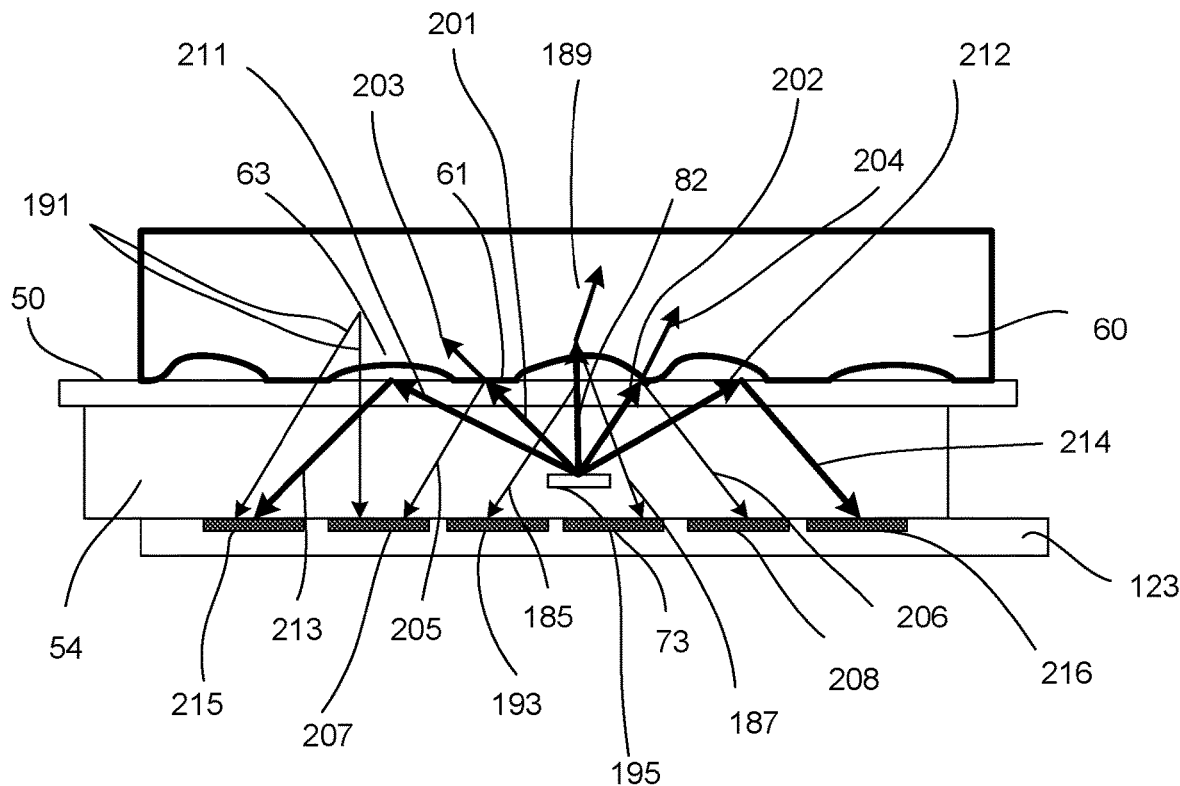
FIGS. 10A and 10B are cross-sectional and top-down views of an exemplary fingerprint sensor module implementing a total reflection fingerprint sensing technique.
Figure 10B:
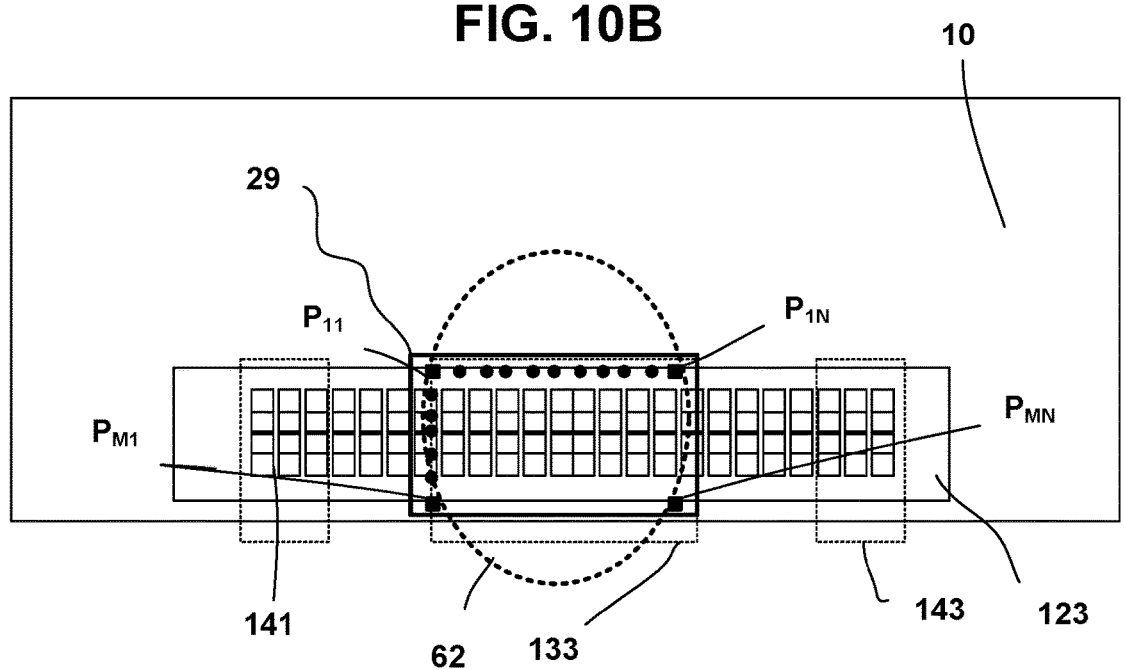

FIGS. 10A and 10B are cross-sectional and top-down views of an exemplary fingerprint sensor module implementing a total reflection fingerprint sensing technique in an invisible optical fingerprint sensor package. As shown in FIG. 10A, the display assembly 10 with the integrated finger property sensor includes a specified display zone 29 for fingerprint detection. Reference number 62 represents a location on the display where the finger 60 can press on the sensor. Similar to FIGS. 1 and 6, the detector array 123 disposed near the specified display zone 29 includes multiple detector elements including detector elements in the fingerprint detector zone 133 for fingerprint and fingerprint property detection responsive to the finger 60 pressing on the sensor at location 62. The detector array 123 also includes detector elements in the environment and blood flow zones 141 and 413 for environment and blood flow speed detection. Examples of the detector elements of the detector array 123 include optical devices such as photodiodes.

As shown in FIG. 10B, the display assembly 10 with an integrated finger property sensor component includes a cover glass 50 and other display layers 54. Display element 73 can be disposed in the other display layers 54. Examples of display element 73 include various types of light emitting devices such as light emitting diodes (LEDs). Also, the detector array 123 is disposed below the cover glass 50 and underneath the display screen layers 54.

As illustrated in FIGS. 10A and 10B, a finger 60 is pressing on the display screen at the photodiode area 62. The finger skin's equivalent index of refraction is about 1.43 at 633 nm. The typical bare cover glass index of refraction is about 1.51. If the cover glass 50 and the display layers 54 are glued together without an air gap, the light emitted by the display element 73 with a large incident angle will be totally reflected at the screen-air interface.

When the display element 73 is turned on, the divergent light beams can be divided into two groups: the central beam 82 that is not totally reflected, and outer beams 201, 202, 211, 212 that are totally reflected when nothing touches the screen surface. For the central light beams 82, the screen surface reflects about 0.1%~3.5% of beam 82 as light beam 185 that is received by photo diodes 193, the finger skin reflects about 0.1%~3.3% of beam 82 as light beam 187 that may be received by some photo diodes 195. The reflection difference is dependent at least on whether the light beams 82 meets with finger skin ridge 61 or valley 63. The rest of the light beam 82 is coupled 189 into the finger tissues.

For outer light beams 201 and 202, the screen surface reflects ~100% as light beams 205 and 206 respectively if nothing touches the screen surface. When the finger skin ridges touch the screen surface near light beams 201 and 202, most of the light power is coupled into the finger tissues 60 as light beams 203 and 204.

For outer light beams 211 and 212, the screen surface reflects at a high reflectivity (e.g., near 100%) as light beams 213 and 214 respectively if nothing touches the screen surface. When the finger touches the screen surface and the finger skin valleys happen to be at light beams 211 and 212 positions, no light power is coupled into finger tissues 60.

All the light beams that are coupled into finger tissues 60 may be randomly scattered to form a low-contrast light 191 and received by multiple photo diodes 207, 215 etc. In the outer light beam illuminated area, the finger skin ridges and valleys cause obvious reflection difference that is detected in the corresponding receiving photo diodes. Because the coordinates of the display emitting elements and the processing photo diodes are known, the fingerprint signals are acquired by comparing the differences based on the known locations of the display elements and detector elements.

The detector array can be disposed under the display, or disposed besides the display, or any locations where the total reflection can be detected. The detector array can be glued onto the display layers, or attached to the display layer with the help of optical wedge, prism, lens etc.

Figure 11A:
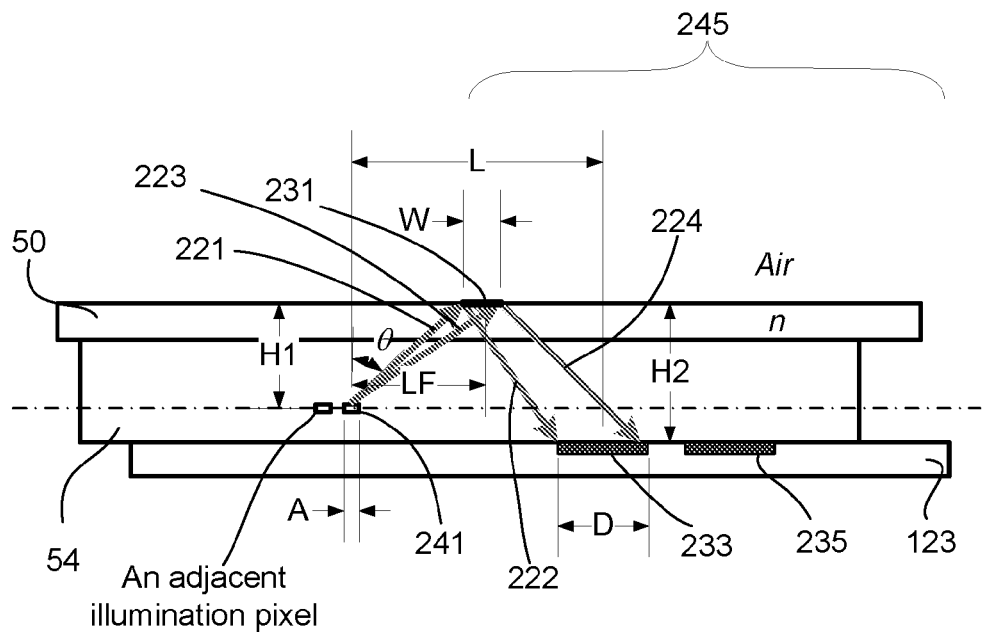
FIGS. 11A and 11B are cross-sectional and top-down views of an exemplary fingerprint sensor module implementing total reflection fingerprint detection scanning.
Figure 11B:
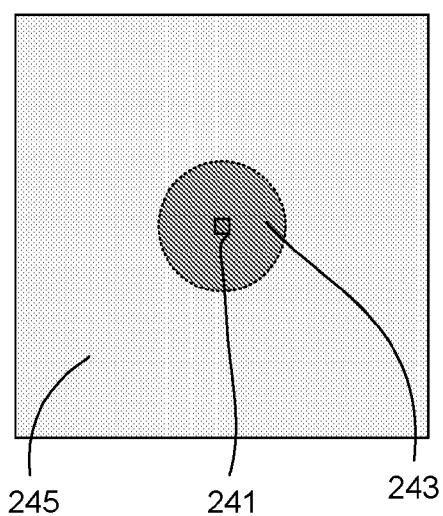

FIGS. 11A and 11B are cross-sectional and top-down views of an exemplary fingerprint sensor module implementing total reflection fingerprint detection scanning in an invisible optical fingerprint sensor package. As shown in FIGS. 11A and 11B, the cover glass 50 and the other display layers 54 are glued together to enable total reflection at the cover glass surface. When the display element (e.g., light emitting element) 241 and the detector element (e.g., processing photodiodes) 233 are defined with respect to the distance between the cover glass 50 surface and the respective display elements and detector elements (e.g. defined as H1, H2, and L respectively), the coordinate LF of the corresponding total reflection zone 231 can be calculated. When the size A of the emitting element 241 and the size D of the processing photo diodes 233 are known, the size W of the corresponding total reflection zone 231 can also be calculated. In various implementations, W can be smaller than D if the emitting elements size is small enough. For an array of illumination pixels 241 in the display screen structure 54, there is a corresponding area 245 which is sufficiently away from the illumination pixels 241 so that the light from the illumination pixels 241 is totally reflected. The optical detectors for fingerprint sensing and other optical sensing can be placed under the display screen structure 54 in the locations within the paths of the totally reflected light beams from the area 245.

Expanding the size A of the emitting element 241 and the size D of the processing photodiodes 233, the size W of the corresponding total reflection zone 231 is also expanded. This implies that the resolution is reduced. Assuming the environment is air with a refraction index of nearly 1, and the cover glass' refraction index is n, the minimum total reflection incident angle θ can be calculated:

$$\theta = \sin^{-1}\left(\frac{1}{n}\right).$$

As a result, the central light beams zone 243 can be calculated. The rest of the positions are located in the total reflection zone 245. For example, if n=1.51, and H1=0.6 mm, for a point light source, the diameter of the central light beams zone is about 1.06 mm. If H2 is given, the closest photo diode distance Lmin can be calculated. For example, when H2=1.2 mm, the minimum Lmin is about 1.59 mm.

When one display element is turned on, multiple point fingerprint signals can be simultaneously acquired with multiple element detector array 123. Or, for a known photo diode, multiple point fingerprint signals can be simultaneously acquired by sequentially lighting on multiple display elements.

FIGS. 12A, 12B, and 12C represent an exemplary fingerprint sensor module installed in a mobile device and implementing total reflection fingerprint detection scanning. As shown, cover glass 50 and other display layers 54 are glued or otherwise engaged together so that total reflection can happen at the cover glass surface. Underneath of the display screen structure 54 is the 2D detector array 261 with multiple photodetectors such as a group of photodetectors 233 and another group of photodetectors 235. One or more light emitting elements 241 are turned on when the device is touched. Each light beam from the light emitting element 241 is totally reflected in a zone 263 within the total reflection zone 245 to a corresponding direction towards the detector array 261 placed underneath the display screen structure 54. For example, light beams 221 and 223 are reflected to light beams 222 and 224 respectively. The reflected light beams 222 and 224 are received by photo diodes 233. Similarly, other light beams from the light emitting element (i.e., light source) 241 are received by photo diodes 235.

The 2D detector array 261 is used to detect the total reflected light from the zone 263 or other zones in the zone 245. The fingerprint in the corresponding detection zone 263 can be detected. Because of the light bending by the reflection and because of the divergence of the probing light beams, there is some distortion in the fingerprint image. This distortion can be corrected based on the coordinates of the light source and the photo diodes. Symmetrically, by using single small-sized photo diodes, and scanning the light sources in 2 dimensions, the fingerprint can also be detected.

In some implementations, the light sources or additional light sources can be packaged at other positions, such as 242 at one end of the display. The added light sources can be partial of the display, or discrete light sources such as LEDs. When the light sources are far away from the detector array, the distortion is reduced.

As described above, the 2D detector array position is also flexible. Any locations where the total reflection can be received may be used to place the detector array.

In some applications, such as in smartphone, tablet etc., the fingerprint distortion can be eliminated with the help of the touch sensor that identifies the touch finger locations.

Figure 13:
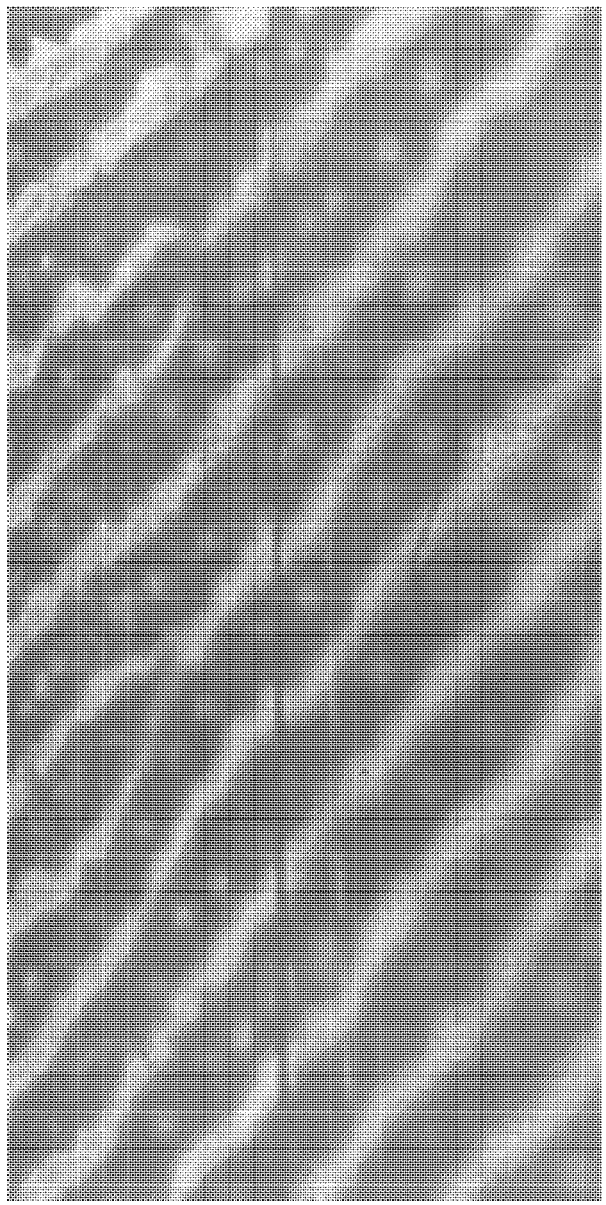
FIG. 13 is an image representing a result of a total reflection fingerprint detection scanning.

FIG. 13 shows an example of an image representing a result of a total reflection fingerprint detection scanning in operating the device shown in FIGS. 11A, 11B, 12A, 12B and 12C. This resultant image of the fingerprint obtained using the total reflection is captured by a 2D optical detector array for the subsequent fingerprint sensing operation. The resultant fingerprint image reveals an enhanced quality of the fingerprint image.

Figure 14A:
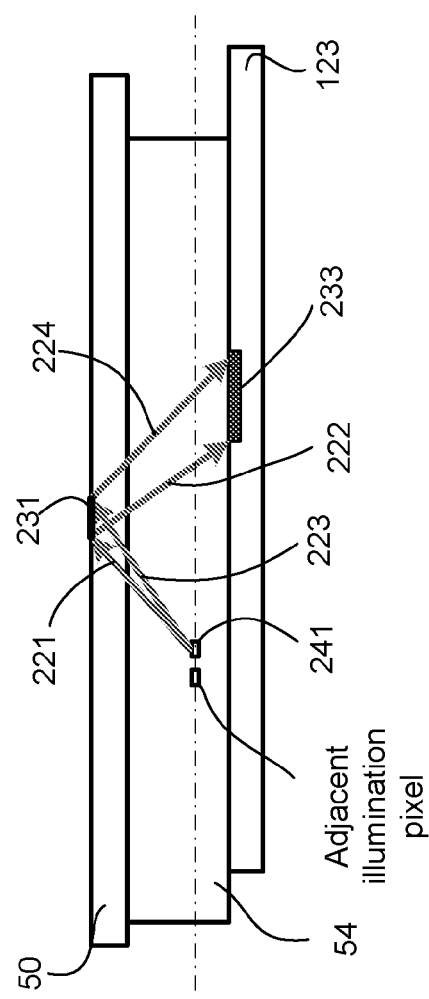
FIGS. 14A, 14B, and 14C represent another exemplary fingerprint sensor module installed in a mobile device and implementing total reflection fingerprint detection.
Figure 14B:
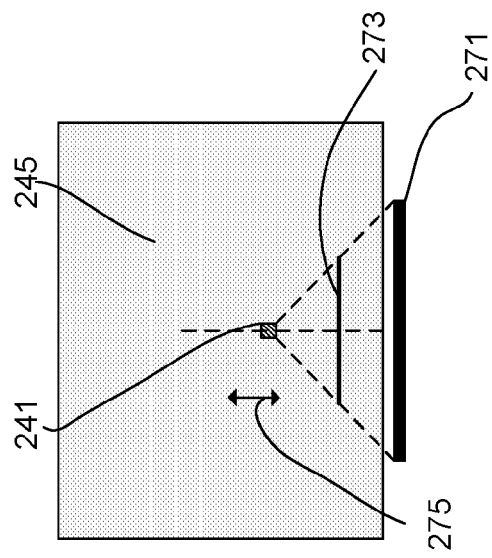
Figure 14C:
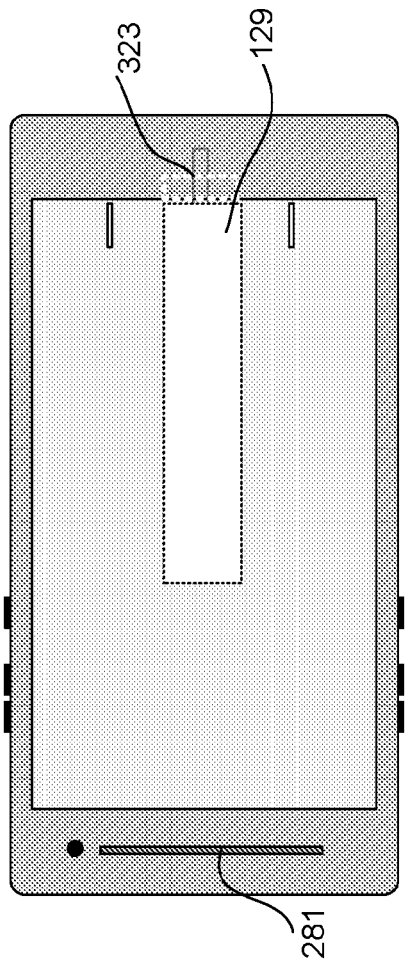

FIGS. 14A, 14B, and 14C represent another exemplary fingerprint sensor module installed in a mobile device and implementing total reflection fingerprint detection. As shown in FIGS. 14A, 14B, and 14C, cover glass 50 and other display layers 54 are glued together to enable total reflection at the cover glass surface. The light emitting element (i.e., light source) 241 is turned on. Each light beam from the source 241 is reflected to a proper direction. For example, light beams 221 and 223 are reflected to light beams 222 and 224 respectively. The reflected light beams 222 and 224 are received by photo diodes 233. Similarly, other light beams from the light source 241 are received by the photo diodes 235.

When a linear detector array 271 is used to detect the total reflected light, the fingerprint in the corresponding detection line 273 can be detected. Because of the light bending by the reflection and because of the divergence of the probing light beams, there is some distortion in the fingerprint image. This distortion can be corrected based on the coordinates of the light source and the photo diodes. When the light source 241 is scanned along linear directions 275, the detection line 273 is also scanned to cover a 2D detection zone.

In some implementations, the light sources or additional light sources can be packaged at other positions, such as 281 at one end of the display. This light sources can be partial of the display, or discrete light sources such as linear LED array. When the light sources are far away from the detector array, the distortion is reduced.

The emitted light from the light source elements can be modulated based on a code system, such as any one of the spread spectrum code systems including Code Division Multiple Access (CDMA) so as to simplify the fingerprint image detection. Any of the CDMA and hybrid CDMA techniques can be used. For example, Direct Sequence Spread Spectrum (DSSS) and Frequency Hopping Spread Spectrum (FHSS) including adaptive FHSS can be used. Using any of the spread spectrum techniques, the light emitted from the light source elements can be modulated using distinct orthogonal pseudorandom spreading codes, different frequencies, amplitudes, phases, or any combination of them.

In addition, the detector array position is flexible. Any locations where the total reflection can be received may be used to place the detector array.

In some applications, such as in smartphone, tablet etc., the fingerprint distortion can be eliminated with the help of the touching sensor that can identify the touch finger locations.

Figure 15A:
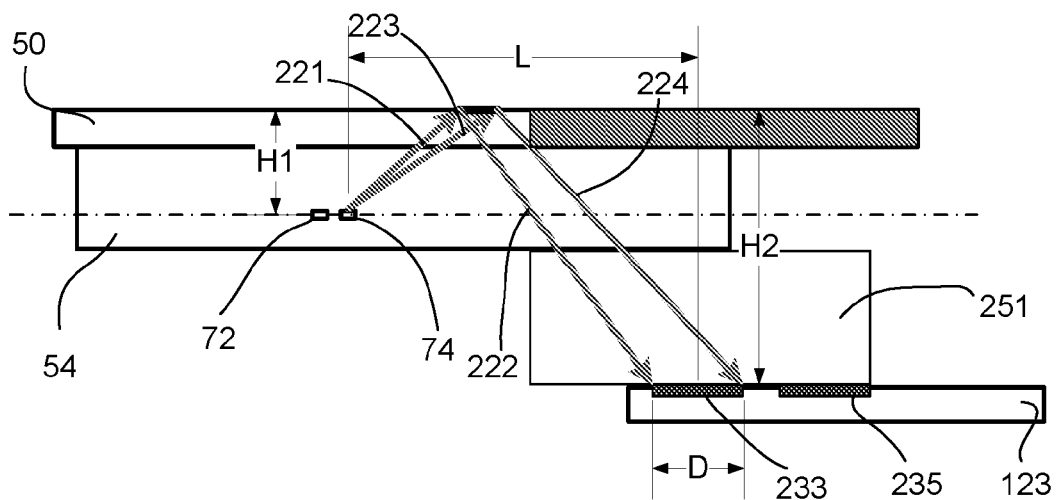
FIGS. 15A and 15B represent another exemplary fingerprint sensor module installed in a mobile device and implementing total reflection fingerprint sensing.
Figure 15B:
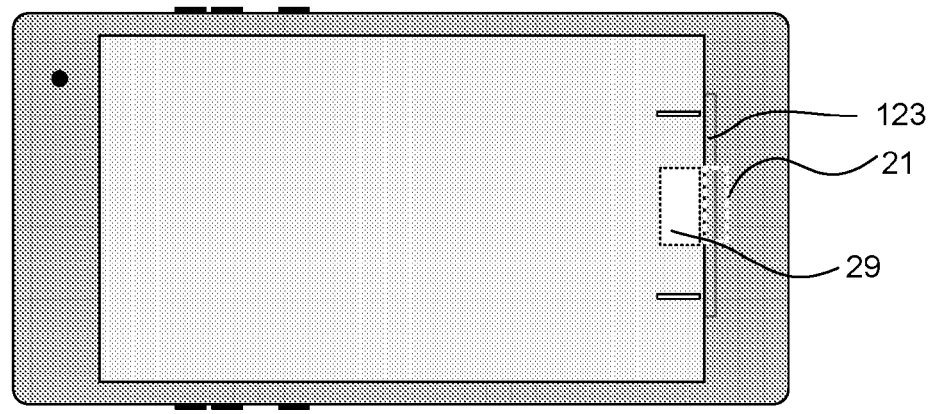

FIGS. 15A and 15B represent another exemplary fingerprint sensor module installed in a mobile device and implementing total reflection fingerprint sensing. The underlying optical detector module is partially under the display screen structure 54 as being "invisible" while a part of the optical detector module is outside the footprint of the display screen structure 54 as being "visible" so that this package is a partially visible and partially invisible package. The finger print sensor of FIGS. 15A and 15B includes detector array(s) 123 disposed near the fingerprint sensing zone 21 and a specified display zone 29 for fingerprint detection. A cover glass 50 and other display layers 54 are glued together to enable total reflection at the cover glass surface. Display elements 72, 74 are embedded in the other display layers 54 and can emit light beams 221, 223 used for fingerprint detection. The emitted light beams 221 and 223 are nearly 100% reflected as cover glass total reflected lights 222 and 224, which are captured or detected by photodiodes 233 and 235. A connection block 251 is glued to the display layers so that the dimension H2 (distance between the cover glass 50 surface and the display elements) is increased. As a result, the minimum L (distance between the light source and the detector) is also increased. Therefore the processing photo diodes can be shifted to out of the display zone. Because the photo diodes only detect the total reflection light, no window is required on the cover glass color layers. Thus, this design is also considered as an invisible package.

In some implementations, the connection block 251 can be of a wedge shape or be a prism. With the help of the connection block, the detector array may be tilted at a proper angle so as to reduce the fingerprint image distortion.

Figure 16:
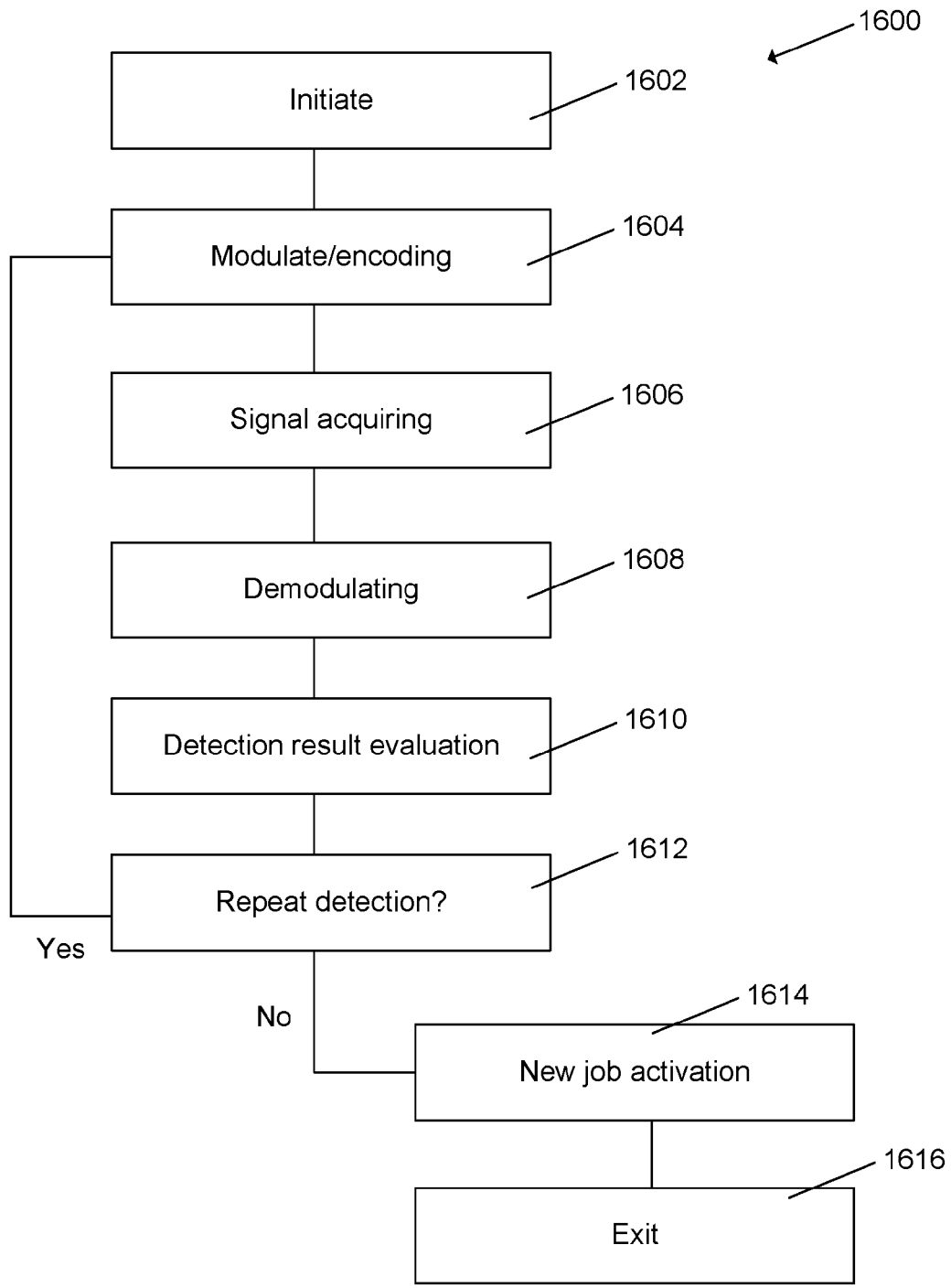
FIG. 16 is a process flow diagram showing an exemplary process 1600 for fingerprint detection.

FIG. 16 is a process flow diagram showing an exemplary process 1600 for fingerprint detection. Sensor detection can be initiated (1602) to activate the related function modules, including the light sources, detector array, modulators, processing circuit, memory, touching sensors etc. A modulating or encoding operation (1604) can be performed to control the light sources to emit light beams that carry the modulation signal information including amplitude, phase shift, frequency change, or a combination. A signal acquisition (1606) can be performed by having the detector array receive the optical signals. Demodulation (1608) is performed to have the processing circuits amplify the signals and check the electric effects. Detection result evaluation (1610) is performed to achieve the fingerprint image, signal strength time dependence (heartbeat, blood flow speed), and compare the signals with the criterion.

To determine whether the detection should be repeated (1612), the following operations are performed. Once the initial detection result is evaluated, the processor makes decisions on following tasks: For example, the processor sends the fingerprint image to memory for switch control or security control, to determine the user blood flow speed etc. According to the application of the detection results, the processor determines whether to continue the detection. When the processor determines that the detection will not be repeated or continued, a new job activation (1616) can be performed according to the detection result, to activate various operations.

Total Reflection Touch Sensing-Refractive Index Matching

Cover glass total reflection effect can be used to acquire the fingerprint and touch signals. The detector array can be integrated directly under the display in some situations such as OLED display, or fixed at the display edge positions. In case of the situation that the light sources are too far away so that the local incident angle is too big, the refractive index matching can guarantee the performance of this concept.

FIG. 17 shows a cross section of another device design where an optical sensing module is provided total reflection touch sensing-refractive index matching technique FIGS. 18A and 18B show an example of a device implementing the design in FIG. 17 based on the total reflection touch sensing-refractive index matching technique. As shown in FIGS. 17, 18A and 18B, cover glass 50 and other display layers 54 are glued together so that total reflection can happen at the cover glass surface. The glue to connect the cover glass 50 and the display layers 54 has refractive index n1, cover glass 50 has a refractive index of n, and the touching material 60a (finger etc.) has a refractive index of n2. If the local incident angle θ is greater than the total reflection angle decided by n and n2, no light can be coupled out by the touching material. When n1 is not greater than n2, any local incident angle θ is acceptable. Thus, a proper glue material can be used to match the refractive index helps improving the performance. Each light beam from the emitting elements 241 is reflected to a proper direction. For example, light beams 301 and 303 are reflected to photo diodes 235. If a linear detector array 271 is used to detect the total reflected light, the fingerprint in the corresponding detection line 273 can be detected. When the light sources 241 are scanned along directions 275, the detection line 273 is also scanned to cover a 2 dimensional (2D) detection zone. When the detector array 271 is 2D, the corresponding detection zone 273 is also 2D. When the light source 241 is scanned, the detection zone 273 is also scanned.

Figure 19A:
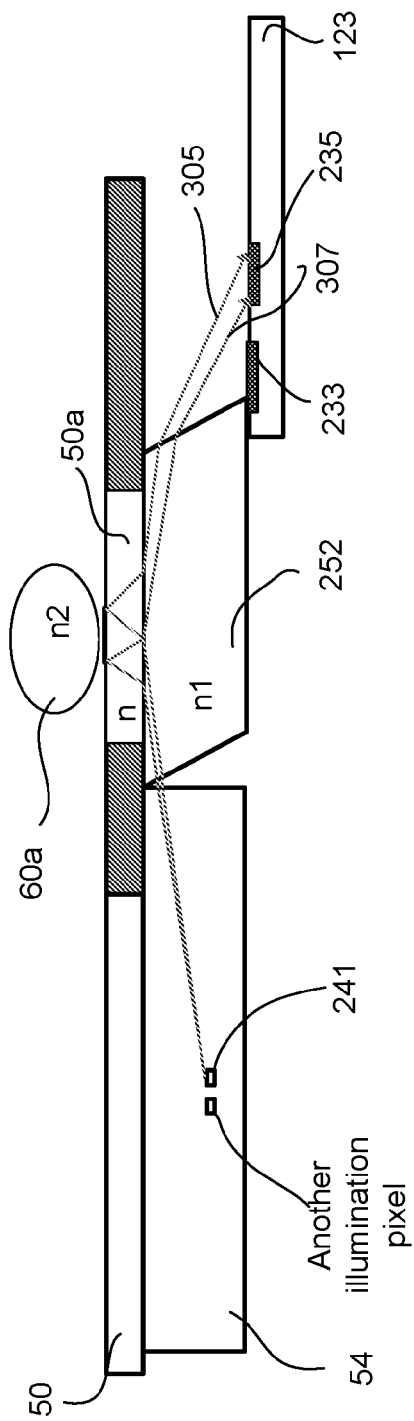
FIGS. 19A, 19B, and 19C are diagrams showing an example of a total reflection touch sensing-refractive index matching technique.
Figure 19C:
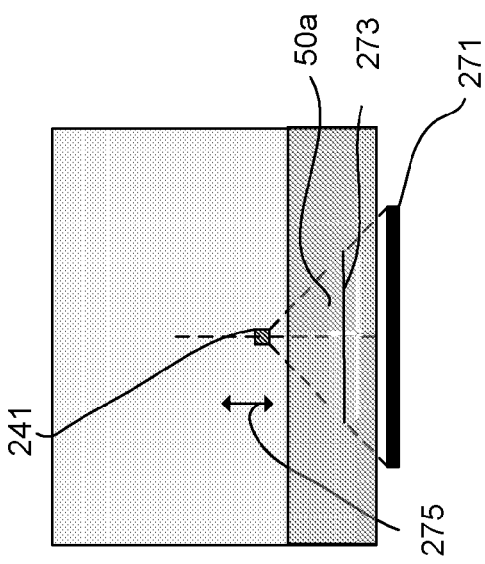
Figure 19B:
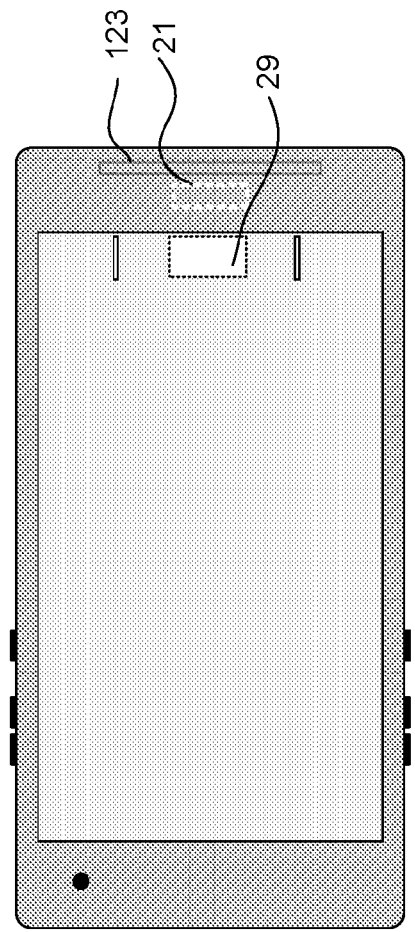

FIGS. 19A, 19B, and 19C are diagrams showing an example of a total reflection touch sensing-refractive index matching technique. As shown in the FIGS. 19A, 19B, and 19C, cover glass 50 and other display layers 54 are assembled together. A connection block 252 is glued to the cover 50 under the sensing window 50a so that total reflection can occur at the sensing window. The connection block 252 has a refractive index of n1, cover glass 50 has a refractive index of n, and the touching material 60a (finger etc.) has a refractive index of n2. When n1 is not greater than n2, any local incident angle is acceptable. Using a proper connection block material to match the refractive index can improve the performance. Each light beam from the emitting elements 241 is reflected to a proper direction. For example, light beams 305 and 307 are reflected to photo diodes 235. When a linear detector array 271 is used to detect the total reflected light, the fingerprint in the corresponding detection line 273 can be detected. When the light sources 241 are scanned along directions 275, the detection line 273 is also scanned to cover a 2D detection zone. Also, when the detector array 271 is 2D, the corresponding detection zone 273 is also 2D. When the light source 241 is scanned, the detection zone 273 is also scanned.

Fingerprint Sensor Technologies

In the above examples for detecting fingerprints and other biometric parameters, the fingerprint sensor is based on optical sensing. Optical fingerprint sensing may be substituted in some implementations by other fingerprint sensors such as capacitive fingerprint sensors or a hybrid fingerprint sensor with both optical sensing and capacitive sensing for sensing fingerprints. Accordingly, fingerprint sensor modules as disclosed in this patent document can be implemented using one or a combination of various sensing technologies including self-capacitive sensing, mutual capacitive sensing, and optical sensing among others. The disclosed technology for detecting a live finger is not dependent on a particular type of sensing technology, and one or a combination of the various sensing technologies can be incorporated.

Figure 20A:
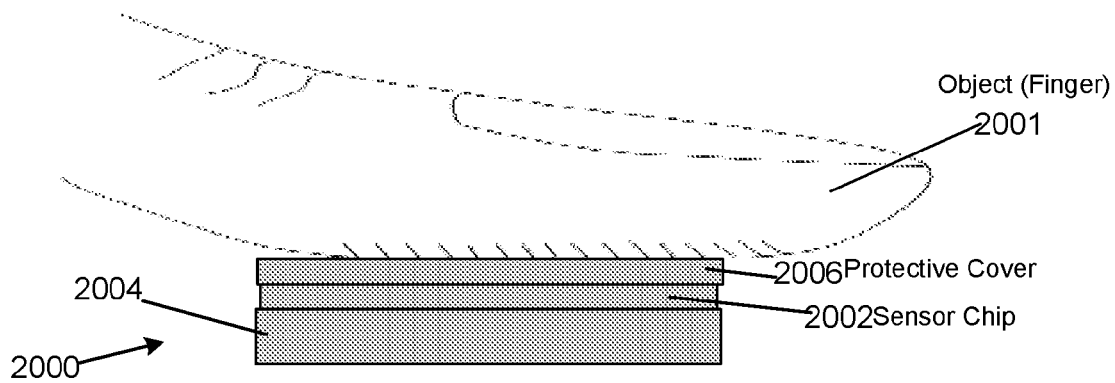
FIG. 20A is a block diagram of an exemplary fingerprint sensor device implementing self-capacitive sensing with active sensor pixel and amplification.

For example, FIG. 20A is a block diagram of an exemplary fingerprint sensor device 2000 implementing self-capacitive sensing with active sensor pixel and amplification. The fingerprint sensor device 2000 is one example of a fingerprint sensor that implements self-capacitive sensing and can be used to replace an optical fingerprint sensor shown in FIGS. 1 through 19C. For example, the capacitive sensing fingerprint sensor in FIG. 20A may be used in combination with the optical sensors 41 and 43 by placing it at one end of the display screen structure 54 underneath a thin top cover glass layer 50 in the visible fingerprint sensor package as shown in FIG. 1. For another example, the capacitive sensing fingerprint sensor in FIG. 20A may be used in combination with the optical sensors 41 and 43 by placing it in a separate sensor structure as such as a button like fingerprint sensor structure in an opening of the top glass cover 50 in some mobile phone designs. The self-capacitive fingerprint sensor device 2000 includes a sensor chip 2002 disposed over a substrate carrier 2004 and a protective film or cover layer 2006 disposed over the sensor chip 2002. The protective film or cover layer 2006 can include an insulator or dielectric material such as glass, silicon dioxide ($SiO_2$), sapphire, plastic, polymer, other substantially similar materials. The protective film or cover layer 2006 can be present to protect the sensor chip 2002 and to function as a part of a dielectric layer between a surface of a finger 2001 and conductive sensing electrodes of individual sensor pixels in the sensor chip 2002. The protective film or cover layer 2006 is an optional layer depending on the application of the fingerprint sensor device 2000.

In some implementations, the fingerprint sensor device 2000 can be disposed through an opening of a top cover glass of an electronic device such as a mobile phone or under a top cover glass of the electronic device. When used in the under-the-glass application, the protective film or cover 2006 is not needed because the top cover glass of the electronic device will function to protect the sensor chip 2002 and act as the dielectric layer.

Figure 20B:
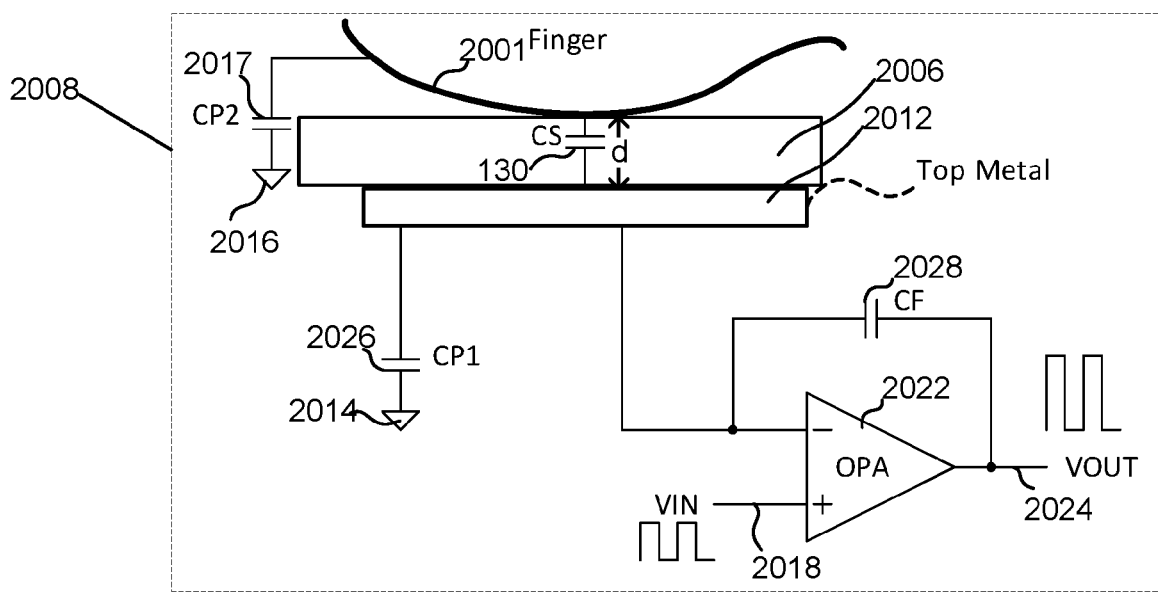
FIG. 20B shows an exemplary sensor pixel.

The sensor chip 2002 includes an array of sensor pixels that in combination senses or captures fingerprint data from the finger 2001 in contact with the protective film or cover layer 2006. An exemplary sensor pixel 2008 is shown in FIG. 20B. Each sensor pixel 2008 of the sensor chip 2002 generates an output signal (e.g., a voltage) based on a capacitance of a capacitor associated with a ridge or valley of the finger 2001. The output signals when combined together can represent a fingerprint image of the finger 2001. Higher the number of pixel sensors, greater the resolution of the fingerprint image.

Figure 20C:
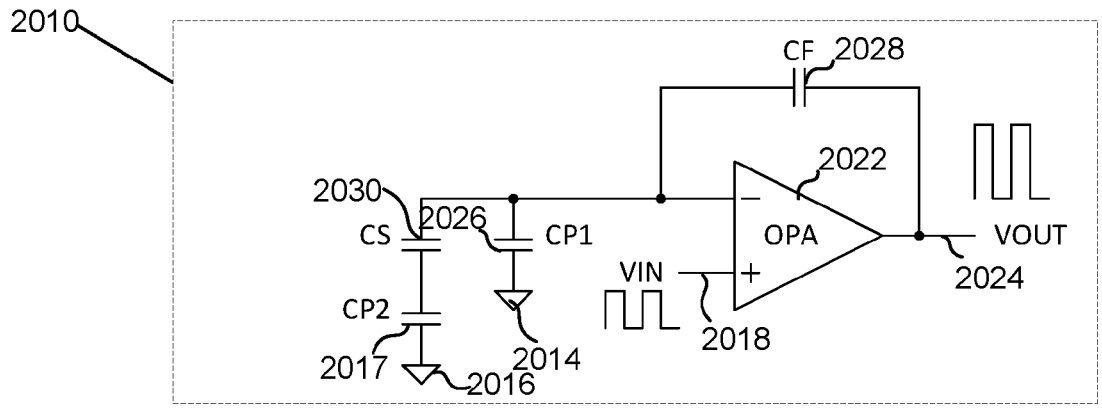
FIG. 20C shows the circuit equivalent of the sensor pixel.

FIG. 20C shows the circuit equivalent of the sensor pixel. Each sensor pixel in the array of sensor pixels of the sensor chip 2002 can be substantially similar to the exemplary sensor pixel 2008. The exemplary sensor pixel 108 includes an operational amplifier 2022 to amplify a capacitance related signal (e.g., voltage signal) detected by the exemplary sensor pixel 2008. A sensor electrode 2012 that includes a conductive material, such as one of a variety of metals is electrically connected to a negative or inverting terminal of the amplifier 2022. The amplifier configuration shown and described with respect to FIG. 20B (and other figures of this patent document) is just one example and other amplifier configurations are possible including a positive feedback configuration. The sensor electrode 2012 and a local surface of the finger 2001 function as opposing plates of a capacitor CS 2030. The capacitance of the capacitor CS 2030 varies based on a distance 'd' between the local surface of the finger 2001 and the sensor electrode 2012, the distance between the two plates of the capacitor CS 2030. The capacitance is inversely proportional to the distance 'd' between the two plates of the capacitor CS 2030. The capacitance is larger when the sensor electrode 2012 is opposite a ridge of the finger 2001 than when opposite a valley of the finger 2001.

In addition, various parasitic capacitors can be formed between different conductive elements in the exemplary sensor pixel 2008. For example, a parasitic capacitor CP1 2026 can form between the sensor electrode 2012 and a device ground terminal 2014. Another parasitic capacitor CP2 2017 can form between the local surface of the finger 2001 and an earth ground 2016. Device ground is coupled to earth ground closely. Yet another capacitor CF 128 can form between an output conductor of the amplifier 2022 and the negative or inverting terminal of the amplifier 2022 and functions as a feedback capacitor to the amplifier 2022.

The positive terminal of the amplifier 2022 is electrically connected to an excitation signal Vin 2018. The excitation signal Vin 2018 can be directly provided to the positive terminal of a dedicated amplifier in each sensor pixel. By providing the excitation signal Vin 2018 directly to the positive terminal of the amplifier 2022, the exemplary sensor pixel 2008 becomes an active sensor pixel. In addition, providing the excitation signal Vin 2018 directly to the positive terminal of the amplifier 2022 eliminates the need to include an excitation electrode, common to all sensor pixels, which reduces a conductive (e.g., metal) layer from the semiconductor structure of the sensor chip 2002. In addition, by providing the excitation signal Vin 2018 directly to the amplifier 2022, the excitation signal Vin 2018 is not applied directly to the finger to avoid potentially irritating or injuring the finger 2001. Moreover, because the excitation electrode for applying the excitation signal directly to the finger is not used, all components of the fingerprint sensor device 2000 can be integrated into a single packaged device, and the entire fingerprint sensor device 2000 can be disposed under the protective cover glass. With the entire fingerprint sensor device 2000 disposed under the protective cover glass, the fingerprint sensor device 2000 is protected from the finger and other external elements that can potentially damage the fingerprint sensor.

The amplifier 2022 can generate an output signal based at least on the variable capacitance of the variable capacitor CS 2030, and the output signal can contributes to the overall fingerprint data. The amplifier 2022 can generate the output signal based at least on the variable capacitance and feedback capacitance of the feedback capacitor CF with no additional non-parasitic capacitances contributing to the output signal. This is partly because, as described above, an additional electrode such as an external drive electrode is not uses in the sensor pixel 2008.

Fingerprint Sensor Technologies: Optical Sensors Integrated with Pixels

In another aspect of the disclosed technology, each sensing pixel of a sensing pixel array of a fingerprint sensor device can be a hybrid sensing pixel having a capacitive sensor for capturing fingerprint information and an optical sensor for capturing fingerprint information including live finger detection as disclosed in this patent document.

Figure 21A:
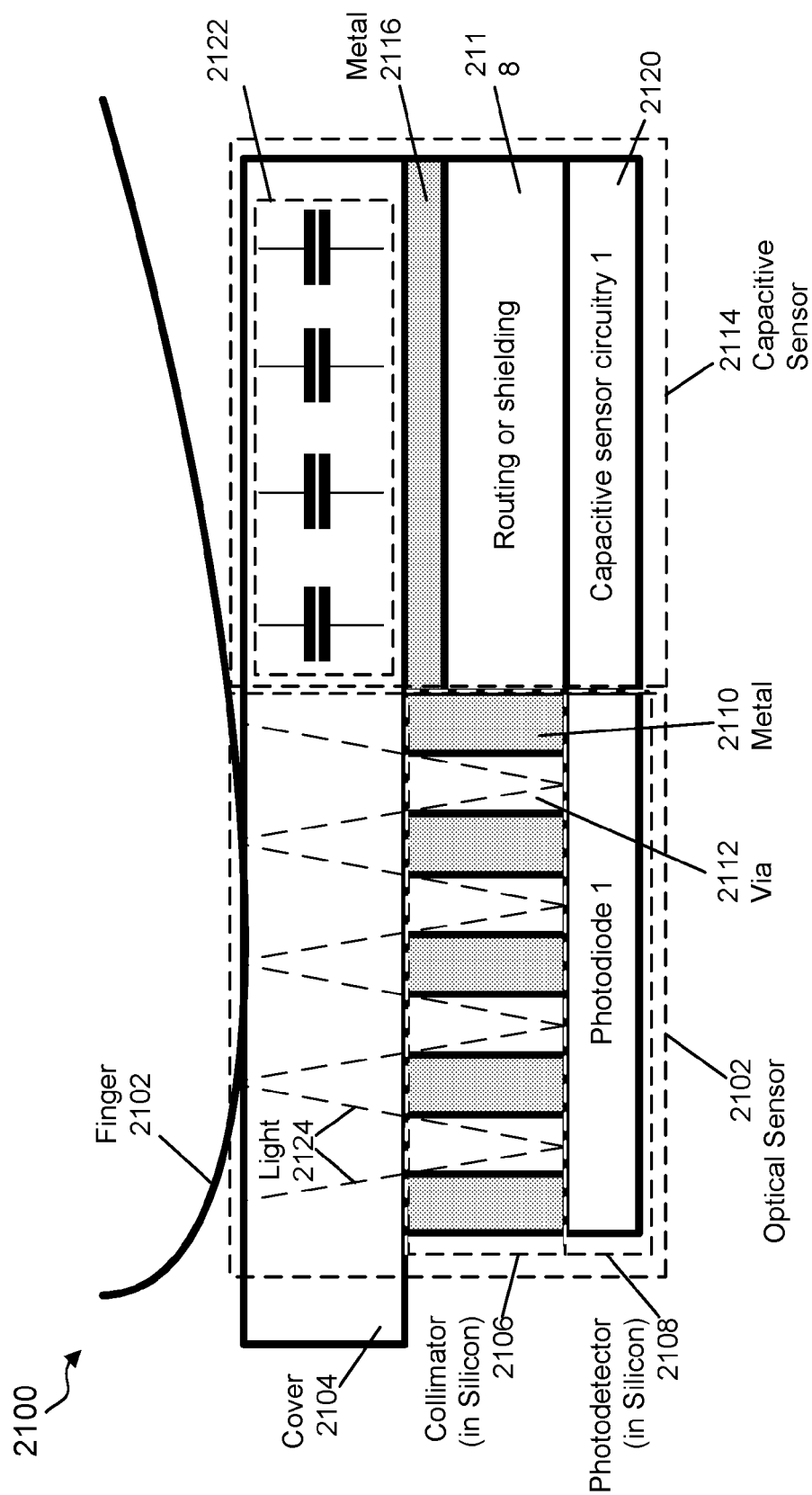
FIG. 21A shows an example of a fingerprint sensor device that incorporates a capacitive sensor in addition to an optical sensor for each sensor pixel in capturing fingerprint information.
Figure 21B:
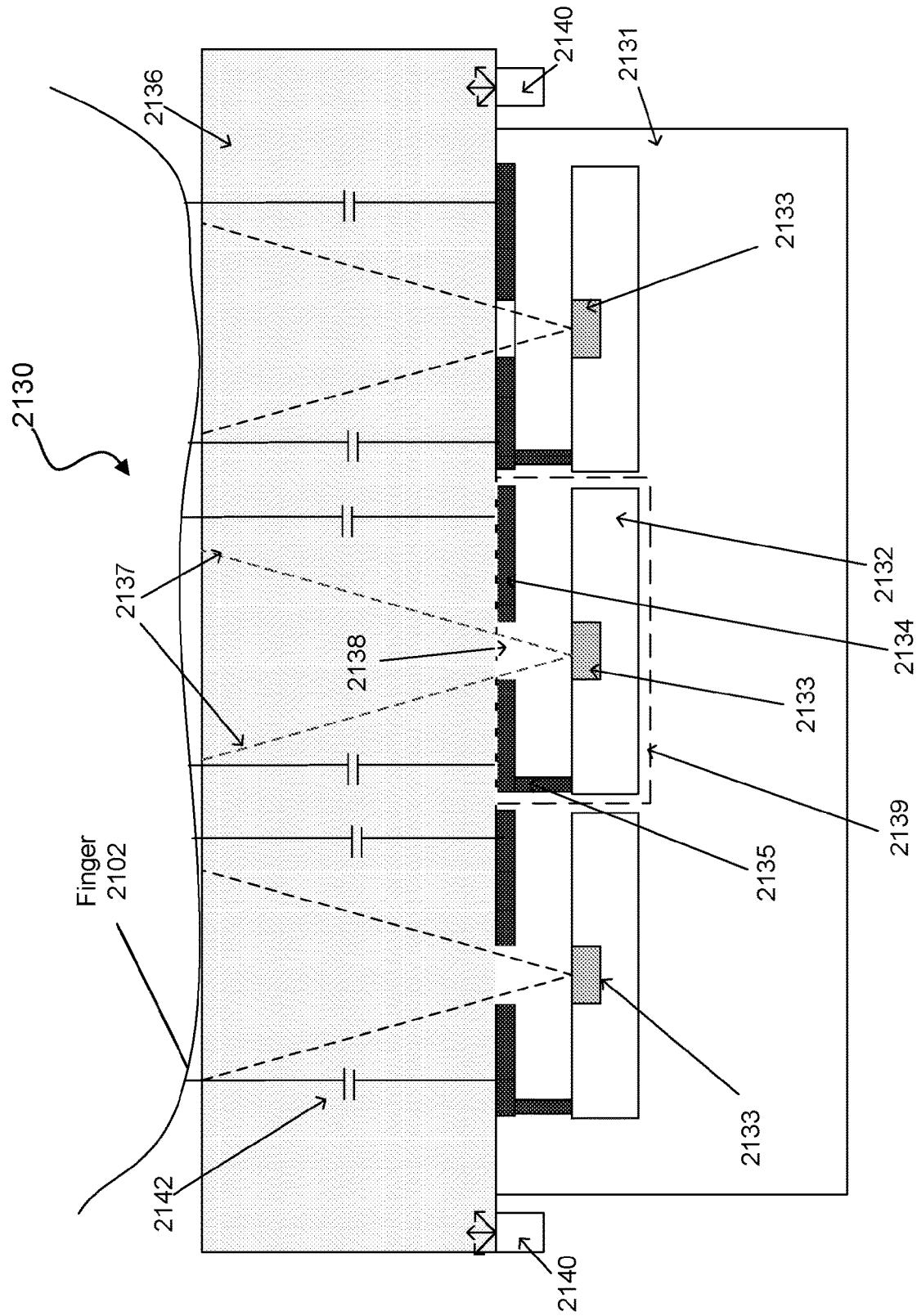
FIG. 21B illustrates another example of a fingerprint sensor device that structurally integrates an optical sensor and a capacitive sensor in each hybrid sensor pixel in a spatially overlap configuration in an array of sensor pixels to reduce the footprint of each hybrid sensing pixel.

FIGS. 21A and 21B show two examples of hybrid sensing pixel designs that combine capacitive sensing and optical sensing within the same sensing pixel.

FIG. 21A shows an example of a fingerprint sensor device 2100 that incorporates a capacitive sensor in addition to an optical sensor for each sensor pixel of an array of sensor pixels in capturing fingerprint information. By combining both capacitive sensors and optical sensors, fingerprint images obtained with the optical sensors can be used to better resolve the 3D fingerprint structure obtained with the capacitive sensors. For illustrative purposes, the structure shown in FIG. 21A represents one sensor pixel in an array of sensor pixels and each sensor pixel includes an optical sensor 2102 and a capacitive sensor 2114 that are disposed next to each other within the same pixel.

The optical sensor 2102 includes a photodetector 2108 and a collimator 2106 disposed over the photodetector 2108 to narrow or focus reflected light 2124 from finger 2102 toward the photodetector 2108. One or more light sources, such as LEDs (not shown) can be disposed around the collimator 2106 to emit light, which is reflected off the finger as reflected light 2124 and is directed or focused toward the corresponding photodetector 2108 to capture a part of the fingerprint image of the finger 2102. The collimator 2106 can be implemented using an optical fiber bundle or one or more metal layer(s) with holes or openings. This use of multiple optical collimators above the optical detector array may be used as a lensless optical design for capturing the fingerprint image with a desired spatial resolution for reliable optical fingerprints sensing. FIG. 21A shows the collimator 2106 implemented using one or more metal layers 2110 with holes or openings 2112. The collimator 2106 in the layer between the top structure or layer 2104 and the photodetectors 2108 in FIG. 21A includes multiple individual optical collimators formed by optical fibers or by holes or openings in one or more layers (e.g., silicon or metal) and each of such individual optical collimators receives light ray 2124 in a direction along the longitudinal direction of each optical collimator or within a small angle range that can be captured by the top opening of each opening or hole and by the tubular structure as shown so that light rays incident in large angles from the longitudinal direction of each optical collimator are rejected by each collimator from reaching the optical photodiode on the other end of the optical collimator.

In the capacitive sensing part of each sensing pixel, the capacitive sensor 2114 includes a capacitive sensor plate 2116 that is electromagnetically coupled to a portion of a finger that is either nearby or in contact with the sensing pixel to perform the capacitive sensing. More specifically, the capacitive sensor plate 2116 and the finger 2102 interact as two plates of one or more capacitive elements 2122 when the finger 2102 is in contact with or substantially near the optional cover 2104 or a cover on a mobile device that implements the fingerprint sensor device 2100. The number of capacitive sensor plates 2116 can vary based on the design of the capacitive sensor 2114. The capacitive sensor plate 2116 can be implemented using one or more metal layers. The capacitive sensor plate 2116 is communicatively coupled to capacitive sensor circuitry 2120 so that the capacitive sensor circuitry 2120 can process the signals from the capacitive sensor plate 2116 to obtain data representing the 3D fingerprint structure. A routing or shielding material can be disposed between the capacitive sensor plate 2116 and the capacitive sensor circuitry to electrically shield the metal plate 2116. The capacitive sensor circuitry 2120 can be communicatively coupled to both the capacitive sensor plate 2116 and the photodetector 2108 to process both the signal from the capacitive sensor plate 2116 and the signal from the photodetector 2108. In FIG. 21A, the capacitive sensor and the optical sensor within each hybrid sensing pixel are adjacent to and displaced from each other without being spatially overlapped.

In implementations, the features in the hybrid sensor design in FIG. 21A can be used in both visible fingerprint sensor package at one end of the display screen structure underneath a top cover glass as shown by the example in FIG. 1 and invisible fingerprint sensor package under the display screen structure as shown by the example in FIG. 6. For example, the optical fingerprint sensor design in FIG. 6 where the optical fingerprint sensor underneath the top glass over 50 and the display screen structure 54 as illustrated in FIG. 6B may construct each optical detector element by an optical collimator element in the detector array 123. Therefore, the optical sensing with the optical collimator feature in FIG. 21A may be implemented in a mobile device or an electronic device is capable of detecting a fingerprint by optical sensing to include a display screen structure; a top transparent layer formed over the display screen structure as an interface for being touched by a user and for transmitting the light from the display screen structure to display images to a user; and an optical sensor module located below the display screen structure to receive light that is returned from the top transparent layer to detect a fingerprint. The optical sensor module includes an optical sensor array of photodetectors that receive the returned light and an array of optical collimators to collect the returned light from the top transparent layer via the display screen structure and to separate light from different locations in the top transparent layer while directing the collected returned light through the optical collimators to the photodetectors of the optical sensor array.

FIG. 21B illustrates another example of a fingerprint sensor device 2130 that structurally integrates an optical sensor and a capacitive sensor in each hybrid sensor pixel in a spatially overlap configuration in an array of sensor pixels to reduce the footprint of each hybrid sensing pixel. In some implementations, the hybrid optical-capacitive sensing fingerprint sensor in FIG. 21B may be used in combination with the optical sensors 41 and 43 by placing it at one end of the display screen structure 54 underneath a thin top cover glass layer 50 in the visible fingerprint sensor package as shown in FIG. 1. In other implementations, the optical-capacitive sensing fingerprint sensor in FIG. 21B may be used in combination with the optical sensors 41 and 43 by placing it in a separate sensor structure as such as a button like fingerprint sensor structure in an opening of the top glass cover 50 in some mobile phone designs. The fingerprint sensor device 2130 includes a semiconductor substrate 2131, such as silicon. Over the substrate 2131, multiple sensing elements or sensing pixels 2139 are disposed. Each sensing element or sensing pixel 2139 includes active electronics circuitry area 2132 including CMOS switches, amplifier, resistors and capacitors for processing sensor signals. Each sensing pixel or sensing element 2139 includes a photodetector 2133 disposed or embedded in the active electronics circuitry area 2132. A capacitive sensor plate or a top electrode 2134 of the capacitive sensor for capacitive sensing is disposed over a photodetector 2133 and includes a hole or opening 2138 on the sensor plate 2134 to function also as a collimator of light for directing light onto the photodetector 2133. A via 2135 filled with conductive material is disposed to electrically connect the top electrode 2134 to the active circuit elements 2132. By adjusting the opening or the hole and the distance of the top electrode 2134 with the photodetector 2133, the light collecting angle 2137 of the photodetector (e.g., photodiode) 2133 can be adjusted. The fingerprint sensor device 2130 is covered by a protective cover 2136, which includes hard materials, such as sapphire, glass etc. Photodetector 2133 light collection angle 2137 can be designed to preserve the spatial resolution of the image collected by the photodiode arrays. A light source 2140, such as an LED, is placed under the cover, on the side of fingerprint sensor device 2130 to emit light, which is reflected off the finger and directed toward the photodetector 2133 to capture the fingerprint image. When a finger touches or comes substantially near the protective cover, the finger and the sensing top electrode 2134 in combination form a capacitive coupling (e.g., capacitor 2142) between the human body and sensing top electrode 2134. The fingerprint sensor device 2130 that includes both optical and capacitive sensors can acquire images of both a light reflection image of fingerprint and also a capacitive coupling image. The sensing top electrode 2134 serves dual purpose: 1) for capacitive sensing, and 2) as a collimator (by fabricating one or more holes on the sensing top electrode 2134) to direct, narrow or focus reflected light from the finger toward the photodetector 2133. Reusing the sensing top electrode 2134 eliminates the need for additional metal layer or optical fiber bundle, and thus reduces each pixel size and accordingly the overall size of the fingerprint sensor device 2130.

In FIG. 21B, the optical sensing design uses the holes or openings 2138 formed between the top layer 2136 and the bottom array of photodetectors 2133 as an optical collimators to select only light rays within certain angles 2137 to preserve the spatial resolution of the image collected by the photodetectors 2133 in the photodetector array as illustrated. Similar to the fiber or other tubular shaped optical collimators in FIG. 21A, the holes or openings 2138 formed between the top layer 2136 and the bottom array of photodetectors 2133 constitute optical collimators to collect the returned light from the top transparent layer via the display screen structure and to separate light from different locations in the top transparent layer while directing the collected returned light through the optical collimators to the photodetectors 2133.

Figure 22:
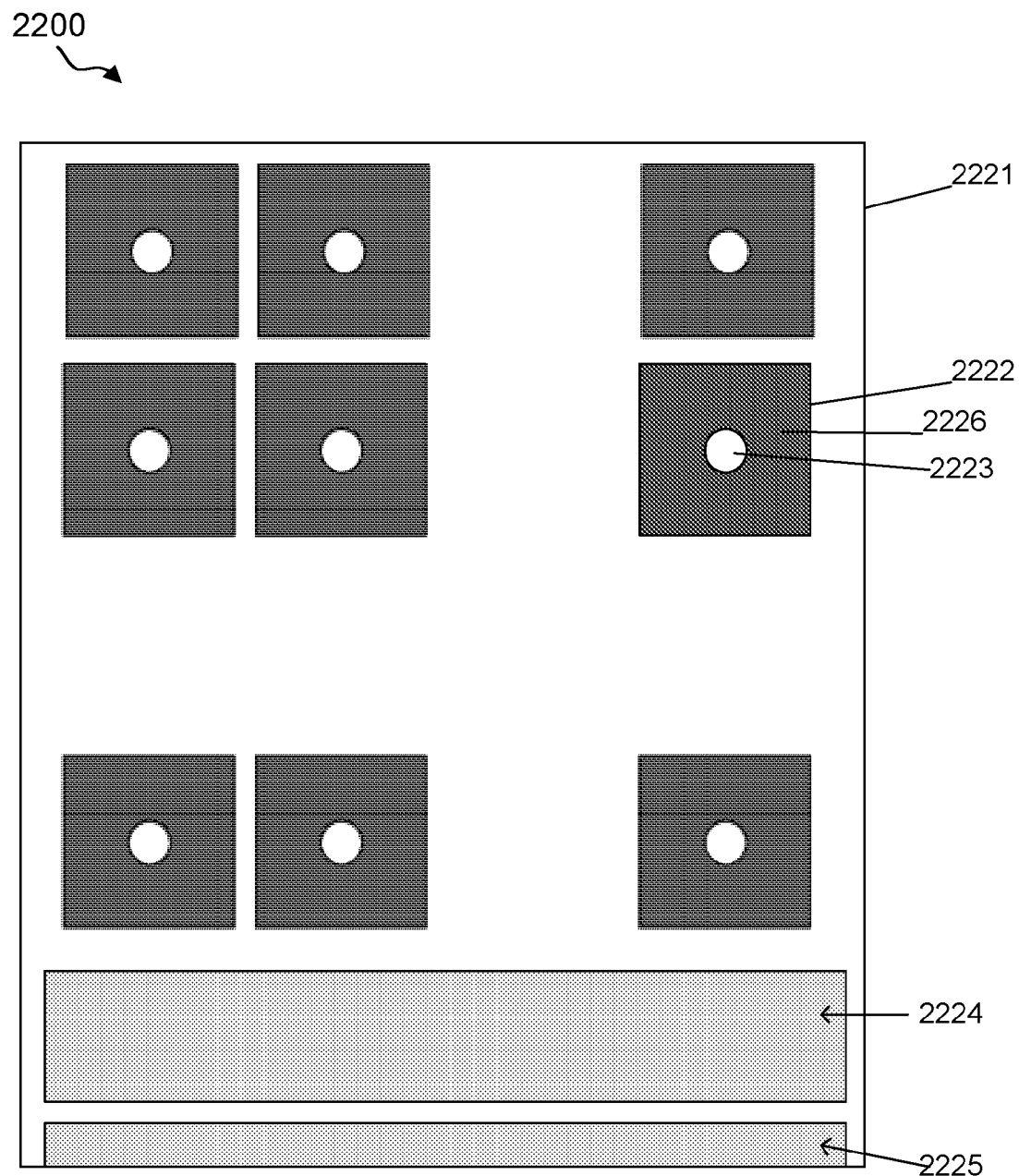
FIG. 22 is a top-down view of an exemplary hybrid fingerprint sensor device incorporating both an optical sensor and a capacitive sensor in each hybrid sensing pixel.

FIG. 22 is a top-down view of an exemplary hybrid fingerprint sensor device 2200 incorporating both an optical sensor and a capacitive sensor in each hybrid sensing pixel. The fingerprint sensor device 2200 is implemented as a CMOS silicon chip 2221 that includes an array of hybrid (incorporating both an optical sensor and a capacitive sensor) sensing elements or pixels 2222. Alternatively, the layout in FIG. 22 can also be for all optical sensing designs disclosed in this document where the openings or holes 2223 represent the optical collimators in FIG. 21A or 21B. The size or dimension of the sensing elements can be in the range of 25 μm to 250 μm, for example. The hybrid sensor device 2200 can include an array of support circuitry including amplifiers, ADCs, and buffer memory in a side region 2224. In addition, the hybrid sensor device 2200 can include an area for wire bonding or bump bonding 2225. A top layer 2226 of the hybrid sensor element 2222 can include a metal electrode for capacitive sensing. One or more openings or holes 2223 can be fabricated on each top metal electrode 23 to structurally serve as a collimator for directing light in a vertical direction to shine on a photodetector under the top electrode. Thus, the top layer 2226 structure can serve dual purposes of optical and capacitive sensing. A sensor device processor can be provided to process the pixel output signals from hybrid sensing pixels to extract the fingerprint information.

In addition to sharing the same structure for capacitive sensing and for focusing light in the vertical direction as a collimator, one instance of sensor signal detection circuitry can be shared between the optical and capacitive sensors to detect the sensor signals from both a photodetector and a capacitive sensor plate.

Figure 23A:
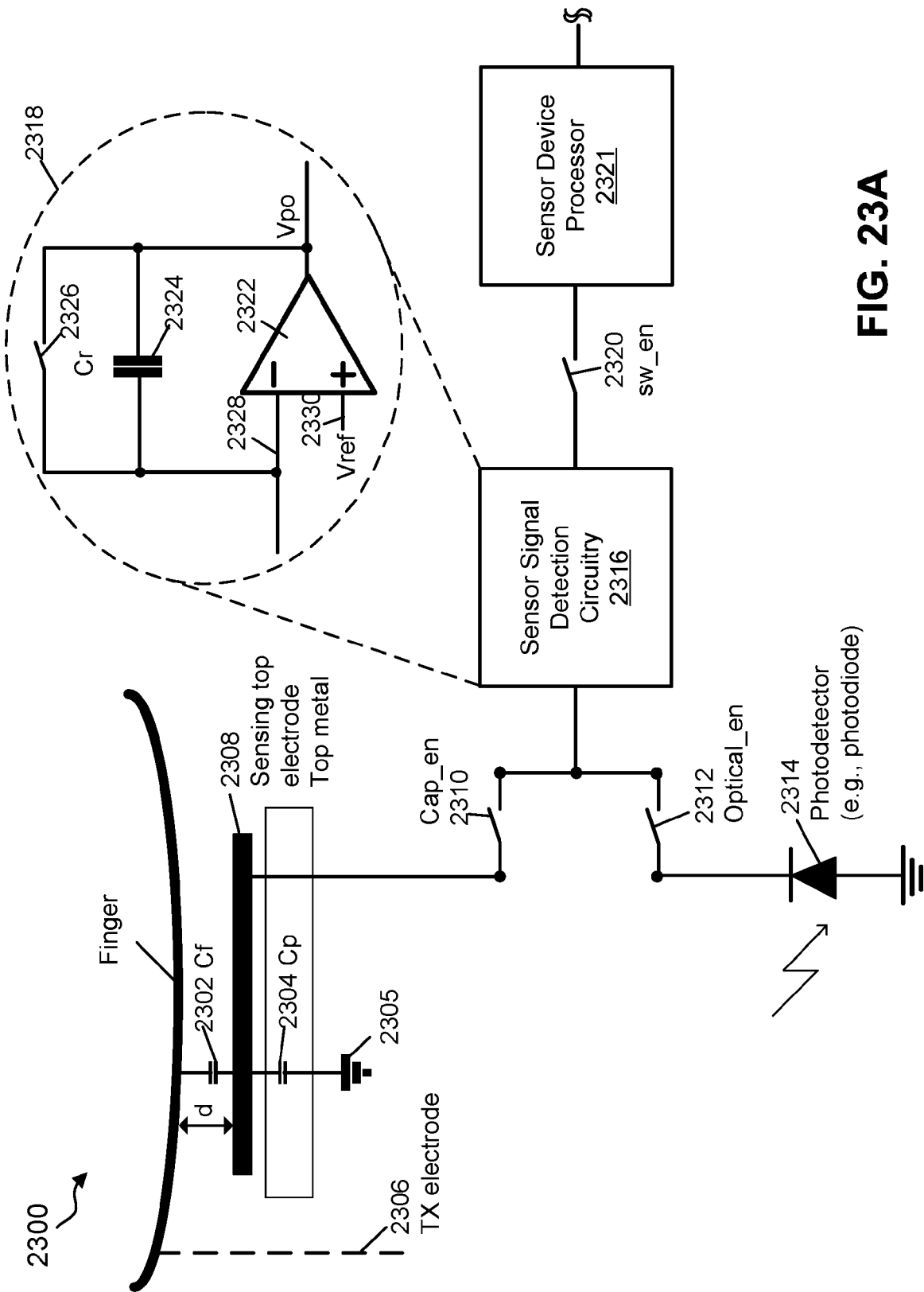
FIG. 23A illustrates a circuit diagram for an exemplary hybrid fingerprint sensing element or pixel having both capacitive sensing and optical sensing functions for fingerprints.

FIG. 23A illustrates a circuit diagram for an exemplary hybrid fingerprint sensing element or pixel 2300 having both capacitive sensing and optical sensing functions for fingerprints. The exemplary sensor pixel 2300 includes sensor signal detection circuitry 2316 to selectively switch between detecting or acquiring sensor signals from a sensing top electrode (e.g., a top metal layer) 2308 based on capacitive sensing and a photodetector (e.g., a photodiode) 2314 based on optical sensing to acquire both a reflective optical image from the photodetector 2314 and a capacitive coupled image from the capacitive sensor electrode 2308 from a finger. In some implementations, the two images from the two sensing mechanisms in each hybrid sensing pixel can be serially processed by the sensor signal detection circuitry. In the illustrated example, switches 2310 and 2312 have first terminals that are electrically coupled to the sensing top electrode 2308 and the photodetector 2314, respectively, and second terminals that are coupled to a common input terminal of the sensor signal detection circuitry 2316 to provide corresponding optical detector signal from the photodetector 2314 and the corresponding capacitive sensing signal from the sensing top electrode 2308 to the sensor signal detection circuitry 2316. When the switch 2310 is turned off (CAP_EN=0) and the switch 2312 is turned on (Optical_en=1), the sensor signal detection circuitry 2316 acquires the optical detector signal representing the optical image of the scanned fingerprint received at the particular hybrid sensing pixel. The sensor signal detection circuitry 2316 can acquire the capacitive sensing signal representing the capacitive image of the scanned fingerprint when switch 2310 CAP_EN=1 and Optical_en=0. After both the optical and capacitive images are acquired, both images can be processed in downstream circuitry separately and in combination to identify the fingerprint characteristics.

With the two modality of imaging by the above hybrid sensing pixels, the performance of the fingerprint identification can be enhanced by making use of the two types of the images in different ways. This enhanced fingerprint identification can be achieved by the sensor device processor, such as sensor device processor 2321, for processing the pixel output signals from the hybrid sensing pixels to extract the fingerprint information. For example, the capacitive image can provide a 3D image on the depth of the ridges and valleys of the fingerprint features. Complementing the 3D capacitive image, the optical image can provide a high resolution 2D information on the fingerprint characteristics. The optical 2D image having a higher spatial resolution can be used to recover the capacitive sensing image resolution because both images information on the same ridges of the fingerprint. In some implementations where the capacitive sensing method may be more sensitive and accurate on identifying the valleys of the fingerprint than the optical sensing method, the spatial resolution of images acquired using the capacitive sensing method can degrade based on the thickness of the cover. This aspect of the capacitive sensing can be supplemented by the optical sensing. In operation, the sensor response may be fixed and the point spread function of the capacitive sensor may be fixed for all sensor positions. The higher resolution optical sensing can be used as a resolution recovery method and can be applied on the capacitive sensing image to enhance the 3D image. A partial high resolution image from optical sensing can be available to help with the recovering method. Thus, the 3D capacitive image can be enhanced to provide more information on the valleys and ridges by interpolating or recovering based on the high resolution 2D image.

The enhanced 3D image can provide an improved fingerprint recognition and matching. In another example, the optical and capacitive images can be stored together to provide two comparisons each time a fingerprint recognition or matching is performed. The use of two types of images for comparison enhances the accuracy and security of the fingerprint sensing system.

The sensor signal detection circuitry 2316 can be implemented in various ways using a number different circuitry designs. In one example, integrator sensing circuitry 2318 can be implemented to store the electric charges caused by ridges and valleys touching or being substantially near the cover of the fingerprint sensor device of the cover of the mobile device. The inclusion of the integrator circuitry 2318 enhances the signal-to-noise ratio (SNR). The integrator sensing circuitry includes an operational amplifier 2322 to amplify a sensor signal, such as a capacitance related or optical related signal (e.g., voltage signal), detected by the sensing top electrode 2308 or the photodetector 2314 of the exemplary sensor pixel 2300. The sensing top electrode 2308 that include a conductive material, such as one of a variety of metals is electrically connected to a negative or inverting terminal 2328 of the amplifier 2322 through the switch 2310. The sensing top electrode 2108 and a local surface of the finger 2302 function as opposing plates of a capacitor Cf 2302. The capacitance of the capacitor Cf 2302 varies based on a distance 'd' between the local surface of the finger and the sensing top electrode 2308, the distance between the two plates of the capacitor Cf 2302. The capacitance of capacitor Cf 2302 is inversely proportional to the distance 'd' between the two plates of the capacitor Cf

2302. The capacitance of capacitor Cf 2302 is larger when the sensing top electrode 2308 is opposite a ridge of the finger than when opposite a valley of the finger.

In addition, various parasitic or other capacitors can be formed between different conductive elements in the exemplary sensor pixel 2300. For example, a parasitic capacitor CP 2304 can form between the sensing top electrode 2308 and a device ground terminal 2305. Device ground is coupled to earth ground closely. Another capacitor Cr 2324 can form between an output conductor of the amplifier 2322 and the negative or inverting terminal 2328 of the amplifier 2322 and functions as a feedback capacitor to the amplifier 2322. Also, a switch 2326 can be coupled between the output of the amplifier 2322 and the negative or inverting terminal 2328 of the amplifier 2322 to reset the integrator circuitry 2318.

The positive terminal of the amplifier 2322 is electrically connected to an excitation signal Vref. The excitation signal Vref can be directly provided to the positive terminal of a dedicated amplifier in each sensor pixel. By providing the excitation signal Vref directly to the positive terminal of the amplifier 2322, the exemplary sensor pixel 2100 becomes an active sensor pixel. In addition, providing the excitation signal Vref directly to the positive terminal of the amplifier 2322 eliminates the need to include an excitation electrode, common to all sensor pixels, which reduces a conductive (e.g., metal) layer from the semiconductor structure of the sensor chip. In some implementations, an optional excitation electrode 2306 can be implemented to enhance the SNR based on the design of the sensor pixel. In addition, by providing the excitation signal Vref 2330 directly to the amplifier 2322, the excitation signal Vref 2322 is not applied directly to the finger to avoid potentially irritating or injuring the finger. Moreover, when the excitation electrode for applying the excitation signal directly to the finger is not used, all components of the fingerprint sensor device can be integrated into a single packaged device, and the entire fingerprint sensor device can be disposed under the protective cover glass. With the entire fingerprint sensor device disposed under the protective cover glass, the fingerprint sensor device is protected from the finger and other external elements that can potentially damage the fingerprint sensor.

In FIG. 23A, the output signal (optical and capacitive) of the sensor signal detection circuitry 2316 (e.g., Vpo of the amplifiers 2322) in the sensor pixels 2300 is electrically coupled to a switch 2320 to selectively output the output signal Vpo from the sensor pixel 2300 to a signal processing circuity including a filter. The switch 2320 can be implemented using a transistor or other switching mechanisms and electrically coupled to a controller to control the switching of the switch 2320. By controlling the switches 2320, 2310 and 2312, the sensor pixels in an array of sensor pixels can be selectively switched between acquiring the optical signals and the capacitive signals. In one implementation, the optical or capacitive signal can be acquired for each line, row or column of sensor pixels in the array and then switched to acquire the other type of signal for the line, row or column. The switching between the optical and capacitive signal acquisition can be performed line-by-line. In another implementation, one type of signal (capacitive or optical) can be acquired for all sensor pixels or elements in the array and then switched to acquire the other type of signal for all of the sensor pixels or elements. Thus, the switching between acquisition of different signal types can occur for the entire array. Other variations of switching between acquisition of the two types of sensor signals can be implemented.

Figure 23B:
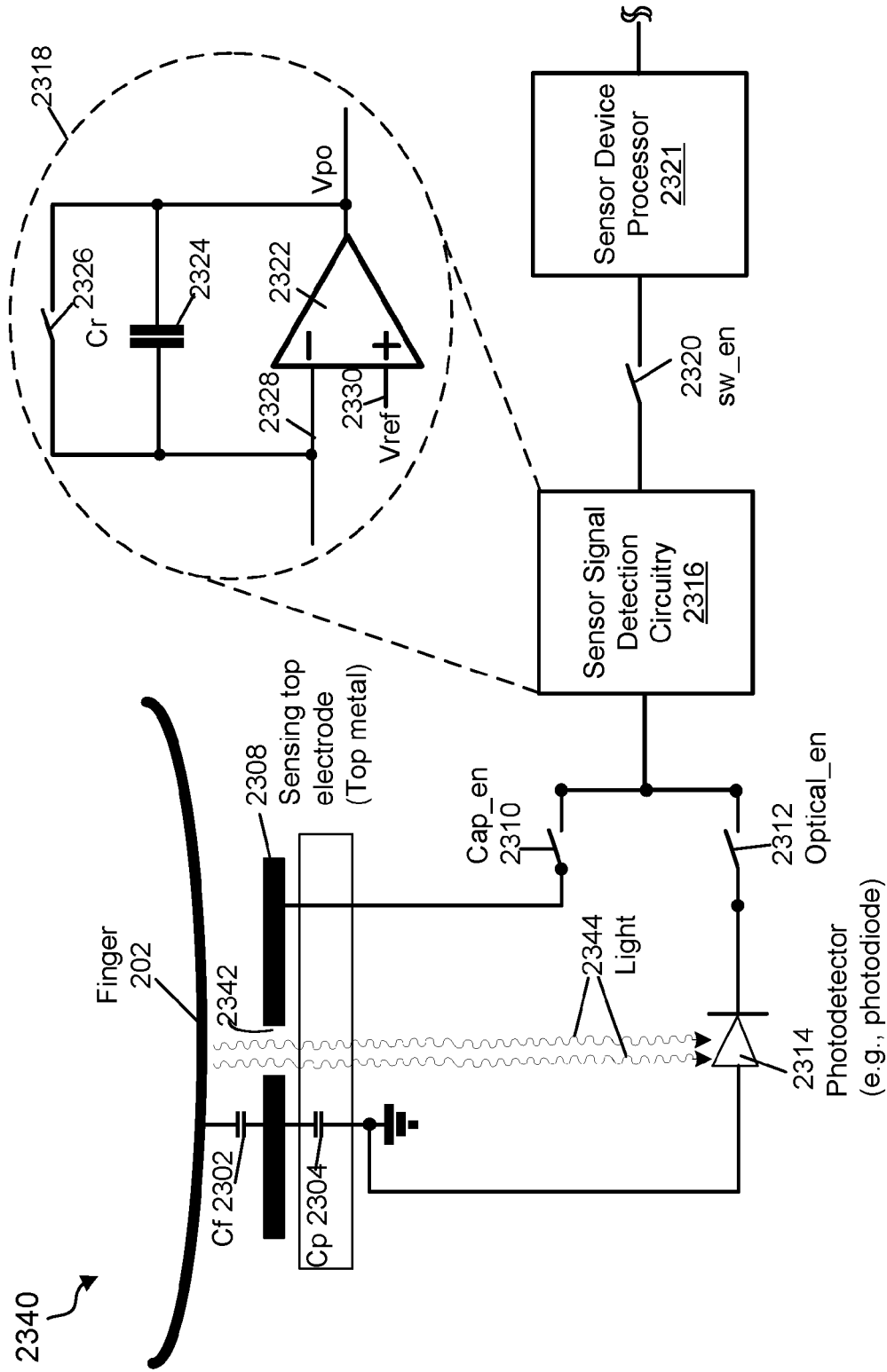
FIG. 23B illustrates a circuit diagram for another exemplary hybrid fingerprint sensing element or pixel.

FIG. 23B illustrates a circuit diagram for another exemplary hybrid fingerprint sensing element or pixel 2340. The hybrid fingerprint sensing element or pixel 2340 is substantially the same as the hybrid fingerprint sensing element or pixel 2300 with respect to the components having the same reference number. For descriptions of the common components having the same reference number, refer to the description of FIG. 23A.

The hybrid fingerprint sensing element or pixel 2340 implements the sensing top electrode 2308 to include a hole or opening 2342 that functions as a collimator to focus or narrow the reflected light 2344 toward the photodetector 2314 (e.g., photodiode). The photodetector 2314 can be positioned or disposed below the collimator implemented using the sensing top electrode 2308 to capture the reflected light 2344 focused by the collimator 2308.

In some implementations, separate instances of sensor signal detection circuitry can be included for the optical and capacitive sensors to detect in parallel the sensor signals from both a photodetector and a capacitive sensor plate.

Figure 23C:
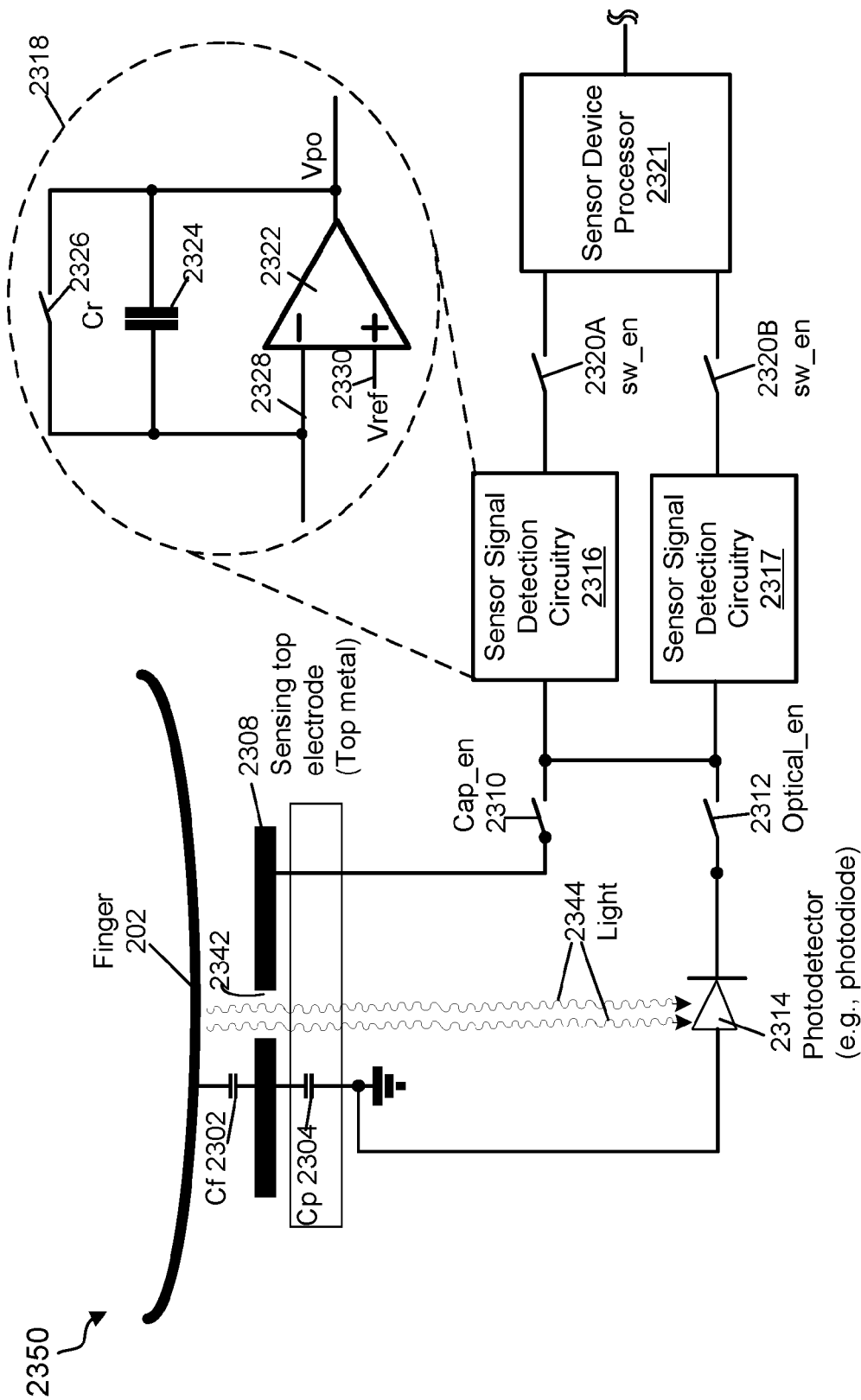
FIG. 23C illustrates a circuit diagram of an exemplary hybrid fingerprint sensing element or pixel for performing parallel detection of sensor signals from the photodetector and the capacitive sensor plate.
Figure 24B:
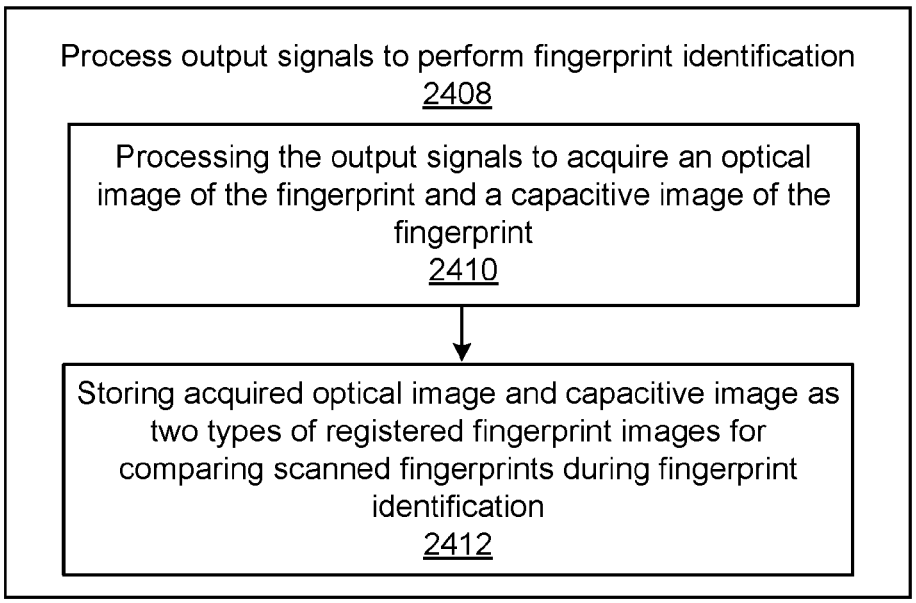
Figure 24C:
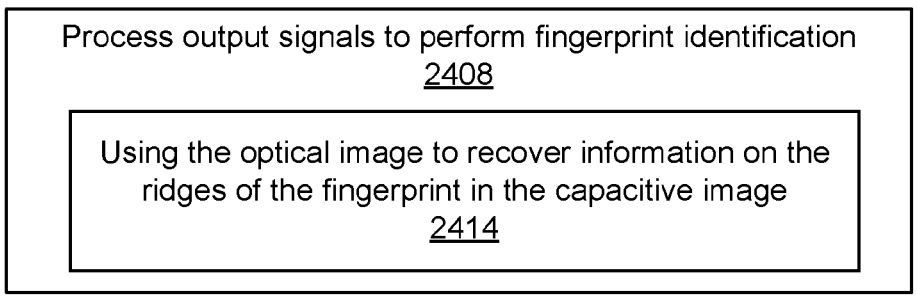
Figure 24D:
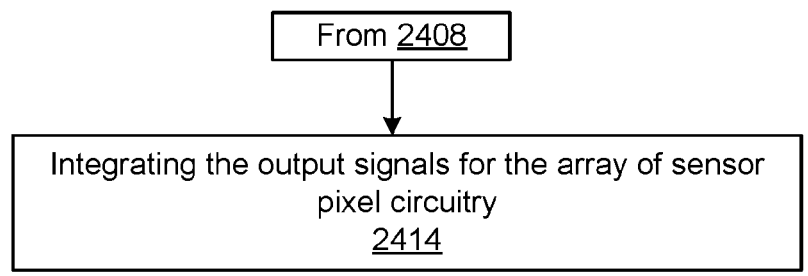

FIG. 23C illustrates a circuit diagram of an exemplary hybrid fingerprint sensing element or pixel 2350 for performing parallel detection of sensor signals from the photodetector and the capacitive sensor plate. The hybrid fingerprint sensing element or pixel 2350 is substantially the same as the hybrid fingerprint sensing element or pixel 2340 with respect to the components having the same reference number. For descriptions of the common components having the same reference number, refer to the description of FIG. 23A.

To perform sensor signal detection from both the capacitive plate and the photodetector in parallel, the hybrid fingerprint sensing element or pixel 2350 includes separate sensor signal detection circuitry 2316 and 2317 communicatively coupled to the sensing top electrode 2308 and the photodetector 2324 respectively. Sensor signal detection circuitry 2317 can be implemented to be substantially similar to sensor signal detection circuitry 2316. In some implementations, switches 2310 and 2312 can be disposed to have first terminals that are electrically coupled to the sensing top electrode 2308 and the photodetector 2314, respectively, and second terminals that are coupled to respective sensor signal detection circuitry 2316 and 2317 to provide the optical detector signal from the photodetector 2314 and the capacitive sensing signal from the sensing top electrode 2308 to the sensor signal detection circuitry 2316 and 2317 respectively When the switches 2310 and 2312 are turned on and off together, the sensor signal detection circuitry 2316 and 2317 can perform sensor signal detection from the capacitive plate 2308 and the photodetector 2314 in parallel. When the switches 2310 and 2312 are turned on and off out of phase with each other, the sensor signal detection circuitry 2316 and 2317 can perform sensor signal detection from the capacitive plate 2308 and the photodetector 2314 in series. In addition, the sensor device processor 2321 can be communicatively coupled to the sensor signal detection circuitry 2316 and 2317 either directly or indirectly through switches 2320A and 2320B to process the detected sensor signals from the capacitive plate 2308 and the photodetector 2314 in parallel or in series.

In another aspect of the disclosed technology, the optical sensor described with respect to FIGS. 21A, 21B, 22, 23A and 23B can be used to measure human heart beat by measuring the reflected light intensity change with time caused by blood flow variations in fingers due to the heart beat and pumping actions of the heart. This information is contained in the received light that is reflected, scattered or diffused by the finger and is carried by the optical detector signal. Thus, the optical sensor can serve multiple functions including acquiring an optical image of the fingerprint and to measure human heart beat. In implementations, a sensor device processor is used to process one or more optical detector signals to extract the heart beat information. This sensor device processor may be the same sensor device processor that processes the pixel output signals from optical sensing pixels or hybrid sensing pixels to extract the fingerprint information.

FIGS. 24A, 24B, 24C and 24D show process flow diagrams of an exemplary process 2400, for performing fingerprint sensing by a hybrid fingerprint sensor that incorporates optical and capacitive sensors. A method 2400 formed by a fingerprint sensor device includes detecting, by an array of sensor pixel circuitry in the fingerprint sensor device, capacitance associated with a touch from a finger indicative of a fingerprint scan (2402). The method includes detecting, by the array of sensor pixel circuitry in the fingerprint sensor device, an optical signal associated with light reflected from the finger (2404). The method includes outputting, by the array of sensor pixel circuitry, output signals responsive to the detected capacitance and optical signal (2406). The output signals can be processed to perform fingerprint identification (2408). Processing the output signals (2408) can include processing the output signals to acquire an optical image of the fingerprint and a capacitive image of the fingerprint (2410). The acquired optical image and capacitive image can be stored as two types of registered fingerprint images for comparing scanned fingerprints during fingerprint identification (2412). Processing the output signals (2408) can include using the optical image to recover information on the ridges of the fingerprint in the capacitive image (2414). The output signals can be integrated for the array of sensor pixel circuitry (2416). Integrating can include integrating by all of the sensor pixel circuitry in the array the output signals in parallel.

Figure 25A:
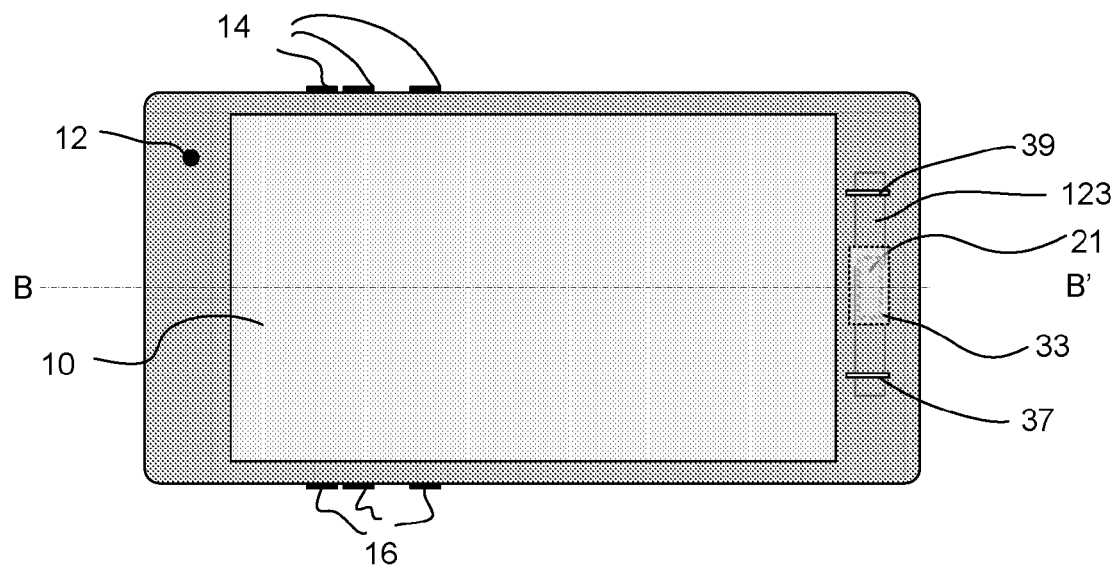
FIGS. 25A and 25B illustrate an example of such a design for a mobile phone, a tablet or other devices where the optical sensor module is outside the display screen assembly 10 as a separate structure.
Figure 25B:
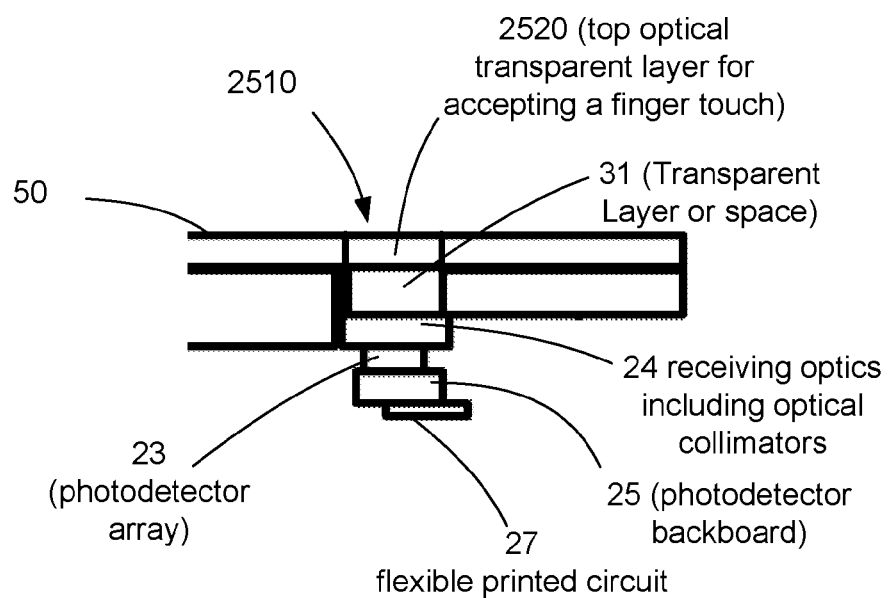

As mentioned above, in some implementations of the optical sensing of fingerprints and other sensing operations, the optical sensor module may be packaged in a discrete device configuration in which the optical sensor module is a distinct structure from the display screen and has a structural border or demarcation with the display screen, e.g., a button like fingerprint sensor structure in an opening of the top glass cover in some mobile phone designs. FIGS. 25A and 25B illustrate an example of such a design for a mobile phone, a tablet or other devices where the optical sensor module is outside the display screen assembly 10 as a separate structure. The top cover glass layer 50 is fabricated to include an opening or through hole 2510 to accommodate for at least the top structure of the optical sensor module. This opening or through hole 2510 can be in a desirable shape such as a circular shape like a button, a rectangular shape such as the elongated rectangular shape shown in FIG. 25A, or other suitable shapes.

The optical sensor module is shown in a cross sectional view along line BB' in FIG. 25A in FIG. 25B. Disposed above the optical detector array 23 are receiving optics 24 (e.g., optical lenses or optical collimators), an optical transparent layer or space 31 above the optics 24 and the top optical transparent layer 2520 that forms an optical input interface for fingerprint sensing and other optical sensing. A back board 25 with integrated circuitry is disposed below the detector array 23. In some implementations, the detector array 23 can be integrated into the backboard 25. The backboard 25 can be disposed over a flexible printed circuit (FPC) 27.

Referring to FIG. 25A, the detector array 23 includes multiple detector elements arranged in different detector zones including a fingerprint detector zone 33 located in the central area of the detector array 23 for fingerprint and fingerprint property detection and one or more additional detector zones 41 and 43 for other optical sensing functions, where the additional detector zones 41 and 43, as illustrated in FIG. 1C, may be environment and blood flow detector zones 41 and 43 for environment and blood flow speed detection. In addition, reference numbers 37 and 39 represent optical illumination zones to produce desired illumination for the additional optical sensing, e.g., emitting red light or light of a desired spectral range to illuminate a user's finger for sensing blood flow speed or glucose level.

The disclosed technology can be applied to implement the fingerprint sensor in smartphones, tablets, laptops, portable game machines, portable controllers, and other electronic devices that uses secure access. In a device based on the disclosed technology, a control circuit, which may include a control processor, can be used to provide the control operations disclosed, e.g., the modulation of the illumination light in optical fingerprint sensing and other control functions and operations.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A fingerprint sensor device, comprising:
   a touch panel with an integrated touch sensor module, the integrated touch sensor module including:
   a plurality of display pixels producing visible light comprising red, green, and blue light for illuminating a user's finger and generating user display images for the user;
   sensing circuitry to generate a sensor signal responsive to detecting a contact input associated with a fingerprint, the sensing circuitry including:
   a fingerprint sensor to detect the contact input and generate a signal indicative of an image of the fingerprint, wherein the fingerprint sensor includes an optical sensor module located below the touch panel to receive a portion of the visible light that is returned from the user's finger, the optical sensor module including an optical detector array of photodetectors positioned to receive at least the portion of the visible returned light to detect a fingerprint, wherein the visible light generated at each pixel is returned and received by a plurality of photodetectors in the optical detector array, and wherein the visible light illuminating the user's finger undergoes total optical reflection at a top surface of the touch panel to direct the totally reflected light to the optical detector array for generating a signal indicative the user's fingerprint, and a biometric sensor to generate a signal indicative of a biometric marker different form the fingerprint, wherein the generated sensor signal includes the signal indicative of the image of the fingerprint and the signal indicative of the biometric marker different from the fingerprint; and processing circuitry communicatively coupled to the sensing circuitry to process the generated sensor signal to determine whether the contact input associated with the fingerprint belongs to a live finger.

2. The fingerprint sensor device of claim 1, wherein the fingerprint sensor includes a capacitive sensor.

3. The fingerprint sensor device of claim 1, wherein the fingerprint sensor includes both capacitive and optical sensors.

4. The fingerprint sensor device of claim 1, wherein the touch panel includes multiple layers including a display screen.

5. The fingerprint sensor device of claim 4, wherein the display screen comprises the plurality of display pixels.

6. The fingerprint sensor device of claim 1, wherein the optical sensor module is integrated with an external device using packaging that hides the optical sensor module from view at a top surface of the external device.

7. The fingerprint sensor device of claim 1, wherein the biometric sensor is configured to generate the signal indicative of the biometric marker including one of heartbeat or blood flow speed.

8. The fingerprint sensor device of claim 7, wherein the biometric sensor configured to generate the signal indicative the heartbeat or blood flow speed operates using a red portion of the visible light.

9. The fingerprint sensor device of claim 7, wherein the optical sensor module includes a light source and a light detector, wherein the light source is configured to emit light toward ridges and valleys of a finger, and wherein the light detector is configured to detect reflected lights reflected from the ridges and valleys.

10. The fingerprint sensor device of claim 9, wherein the processing circuitry is configured to determine a difference between the reflected lights from the ridges and valleys to detect an image of the fingerprint.

11. The fingerprint sensor device of claim 7, wherein the optical sensor module includes a light source and a light detector, wherein the light source includes a light emitting diode or a laser diode, and wherein the light detector includes a photodiode.

12. The fingerprint sensor device of claim 11, wherein the light source is configured to emit light toward a source of the fingerprint and wherein the light detector is configured to detect scattered light that is scattered from the source of the fingerprint responsive to the emitted light.

13. The fingerprint sensor device of claim 7, wherein the optical sensor module includes a light detector, and wherein the light detector includes a photodiode array.

14. The fingerprint sensor device of claim 13, wherein the photodiode array includes a single sensitive element or multiple sensitive elements.

15. The fingerprint sensor device of claim 1, wherein the fingerprint sensor device is configured to analyze the signal indicative of the image of the fingerprint to identify dynamic changes in image details over a period of time.

16. An electronic device, comprising:

a central processor;

a touch panel in communication with the central processor, the touch panel comprising a plurality of display pixels producing visible light comprising red, green, and blue light for illuminating a user's finger and generating user display images for the user; and a fingerprint sensor device integrated into the touch panel and in communication with the central processor, wherein the fingerprint sensor device includes:

a sensing circuitry to generate a sensor signal responsive to detecting a contact input associated with a fingerprint, the sensing circuitry including:

a fingerprint sensor to detect the contact input and generate a signal indicative of an image of the fingerprint, wherein the fingerprint sensor includes an optical sensor module located below the touch panel to receive a portion of the visible light that is returned from the user's finger, the optical sensor module including an optical detector array of photodetectors positioned to receive at least the portion of the visible returned light to detect a fingerprint, wherein light generated at each pixel is returned and received by a plurality of photodetectors in the optical detector array, and wherein the visible light illuminating the user's finger undergoes total optical reflection at a top surface of the touch panel to direct the totally reflected light to the optical detector array for generating a signal indicative the user's fingerprint, and a biometric sensor to generate a signal indicative of an identification of a biometric marker different from the fingerprint, wherein the generated sensor signal includes the signal indicative of the image of the fingerprint and the signal indicative of the biometric marker different from the fingerprint; and processing circuitry communicatively coupled to the sensing circuitry to process the generated sensor signal to determine whether the contact input associated with the fingerprint belongs to a live finger.

17. The electronic device of claim 16, wherein the electronic device includes a smartphone, a tablet computer, a laptop computer, a wearable device, or a discrete sensor device.

18. The electronic device of claim 16, wherein the biometric sensor is configured to generate a signal indicative of a heartbeat or blood flow speed using a red portion of the visible light.

19. The electronic device of claim 16, wherein the optical sensor module includes a light source and a light detector, wherein the light source is configured to emit light toward ridges and valleys of a finger, and wherein the light detector is configured to detect reflected lights reflected from the ridges and valleys.

20. The electronic device of claim 19, wherein the processing circuitry is configured to determine a difference between the reflected lights from the ridges and valleys to detect an image of the fingerprint.

21. The electronic device of claim 16, wherein the optical sensor module includes a light source and a light detector, wherein the light source includes a light emitting diode or a laser diode, and wherein the light detector includes a photodiode.

22. The electronic device of claim 21, wherein the light source is configured to emit light toward a source of the fingerprint and wherein the light detector is configured to detect scattered light that is scattered from the source of the fingerprint responsive to the emitted light.

23. The electronic device of claim 16, wherein the optical sensor module includes a light detector, and wherein the light detector includes a photodiode array.

24. The electronic device of claim 23, wherein the photodiode array includes a single sensitive element or multiple sensitive elements.

25. The electronic device of claim 16, wherein the touch panel includes a display screen.

26. The electronic device of claim 25, wherein the sensor module is configured to use a portion of light emitted by the display screen as a light source.

27. The electronic device of claim 16, comprising extra light sources.

28. The electronic device of claim 16, wherein the optical sensor module includes a light detector, and wherein the light detector includes light sensitive elements arranged in a pattern.

29. The electronic device of claim 16, wherein the biometric sensor is configured to monitor glucose or a degree of oxygen saturation.

30. The electronic device of claim 16, wherein the sensor circuitry is configured to detect a palm.

31. The electronic device of claim 16, comprising:
a modulator to modulate light emitted by a light source; and
a demodulator to demodulate a resultant signal detected in response to the modulated light.

32. The electronic device of claim 31, wherein the modulator is configured to modulate the light emitted by the light source using a distinct digital code.

33. The electronic device of claim 32, wherein the distinct digital code is based on a Code Division Multiple Access (CDMA) code.

34. The electronic device of claim 32, wherein the modulator is configured to adaptively adjust modulation of the light to enhance signal to noise ratio.

35. The device as in claim 34, wherein the optical collimators include a layer and an array of holes through the layer.

36. A method of detecting a live finger during a fingerprint scan, the method comprising:
generating by a plurality of display pixels visible light comprising red, green, and blue light for illuminating a user's finger and generating user display images for the user;
detecting, by a fingerprint sensor, a contact input associated with a source of a fingerprint, wherein the fingerprint sensor includes an optical sensor module located below a touch panel to receive a portion of the visible light that is returned from the user's finger, the optical sensor module including an optical detector array of photodetectors positioned to receive at least the portion of the visible returned light to detect a fingerprint, wherein light generated at each pixel is returned and received by a plurality of photodetectors in the optical detector array, and wherein the illumination light undergoes total optical reflection at a top surface of the touch panel to direct the totally reflected light to the optical detector array for generating a signal indicative the user's fingerprint;
generating an image signal from the fingerprint sensor responsive to the detected contact input, wherein the generated image signal from the fingerprint sensor is indicative of one or more images of the fingerprint;
generating, by a biometric sensor, a biometric marker detection signal indicative of a biometric marker different from the fingerprint; and
processing, by processing circuitry, the generated image signal and the biometric marker detection signal to determine whether the detected contact and the associated one or more fingerprint images are from a live finger.

37. The method of claim 36, wherein the biometric sensor is configured to generate a signal indicative of a heartbeat or blood flow speed using a red portion of the visible light.

38. The method of claim 37, wherein processing the biometric marker detection signal includes processing the detected scattered light to monitor a glucose level or a degree of oxygen saturation.

39. An electronic device with touching sensing and fingerprint sensing capabilities, comprising:
a touch screen that provides touch sensing operations, the touch screen comprising a plurality of display pixels producing visible light comprising red, green, and blue light for illuminating a user's finger and generating user display images for the user;
a top transparent layer formed over the touch screen as an interface for being touched by a user for the touch sensing operations;
an optical sensor module located below the touch screen to receive a portion of the visible light that is returned from the top transparent layer and transmits through the touch screen, the optical sensor module including an optical detector array of photodetectors positioned to receive at least the portion of the visible returned light to detect a fingerprint, wherein light generated at each pixel is returned and received by a plurality of photodetectors in the optical detector array for generating a signal indicative the user's fingerprint; and
a biometric sensor to generate a signal indicative of a heartbeat or blood flow speed using a red portion of the visible light.

40. The device as in claim 39, wherein the optical sensor module includes an array of optical collimators located between the touch screen and the optical detector array to direct the portion of the visible returned light to the photodetectors through the optical collimators.

41. The device as in claim 40, wherein the optical collimators include optical fibers.

42. The device as in claim 39, wherein the optical module includes, in addition to the optical detector array for detecting a fingerprint, a second optical detector that detect the portion of the visible returned light to determine whether the returned light is reflected from a finger of a live person.

43. The device as in claim 42, wherein the second optical detector detects a heartbeat of a person.

44. The device as in claim 42, wherein the second optical detector detects a blood flow speed of a person.

45. The device as in claim 42, wherein the second optical detector detects a parameter of the blood of a person.

46. The device as in claim 39, further comprising:
one or more illumination light sources that are separate from the display pixels of the touch screen and produce illumination light for illuminating the user's finger in touch with the top transparent layer to produce the visible returned light.

47. The device as in claim 39, wherein
the touch screen includes a fingerprint sensing zone for the user to touch for fingerprint sensing to generate the portion of the visible returned light received by the optical detector array for detecting the fingerprint including a first optical sensing zone and a second optical sensing zone, wherein
the optical module includes (1) a first additional optical detector located on a first side of the optical detector array to receive a portion of the visible returned light from the first optical sensing zone, and (2) a second additional optical detector located on a second opposite side of the optical detector array to receive a portion of the visible returned light from the second optical sensing zone, wherein the first and second additional optical detectors produce detector signals indicating whether the returned light is reflected from a finger of a live person.

48. The device as in claim 47, wherein the first and second additional optical detectors produce detector signals indicating a heartbeat of a live person.

49. The device as in claim 47, wherein the first and second additional optical detectors produce detector signals indicating a blood flow speed of a live person.

50. The device as in claim 47, wherein the optical sensor module includes an array of optical collimators located between the touch screen and the optical detector array to direct the portion of the visible returned light to the photodetectors through the optical collimators.

51. The device as in claim 39, wherein the touch screen includes a fingerprint sensing zone for the user to touch for fingerprint sensing, and wherein the plurality of display pixels is located to generate illumination light to the fingerprint sensing zone.

52. The device as in claim 39, comprising:
a control that controls illumination light in fingerprint sensing by the optical sensor module.

53. The device as in claim 52, wherein the control modulates the illumination light in the fingerprint sensing.

* * * * *